US010780181B2

(12) United States Patent
Van Berkel et al.

(10) Patent No.: US 10,780,181 B2
(45) Date of Patent: *Sep. 22, 2020

(54) PYRROLOBENZODIAZEPINE-ANTIBODY CONJUGATES

(71) Applicant: MEDIMMUNE LIMITED, Cambridge (GB)

(72) Inventors: Patricius Hendrikus Cornelis Van Berkel, Epalinges (CH); Philip Wilson Howard, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 97 days.

This patent is subject to a terminal disclaimer.

(21) Appl. No.: 15/897,835

(22) Filed: Feb. 15, 2018

(65) Prior Publication Data

US 2018/0250417 A1  Sep. 6, 2018

Related U.S. Application Data

(63) Continuation of application No. 14/434,816, filed as application No. PCT/EP2013/071346 on Oct. 11, 2013, now Pat. No. 9,931,414.

(60) Provisional application No. 61/712,928, filed on Oct. 12, 2012, provisional application No. 61/712,924, filed on Oct. 12, 2012, provisional application No. 61/784,362, filed on Mar. 14, 2013, provisional application No. 61/784,383, filed on Mar. 14, 2013, provisional application No. 61/784,421, filed on Mar. 14, 2013.

(51) Int. Cl.
| | |
|---|---|
| *A61K 39/00* | (2006.01) |
| *A61K 47/68* | (2017.01) |
| *A61K 31/5517* | (2006.01) |
| *A61K 45/06* | (2006.01) |
| *C07K 16/28* | (2006.01) |

(52) U.S. Cl.
CPC ...... *A61K 47/6849* (2017.08); *A61K 31/5517* (2013.01); *A61K 45/06* (2013.01); *A61K 47/6803* (2017.08); *C07K 16/2803* (2013.01); *C07K 2317/56* (2013.01)

(58) Field of Classification Search
CPC .................................................. A61K 47/6849
See application file for complete search history.

(56) References Cited

U.S. PATENT DOCUMENTS

| | | | |
|---|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Susaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |

(Continued)

FOREIGN PATENT DOCUMENTS

| | | |
|---|---|---|
| EP | 0522868 | 1/1993 |
| EP | 0875569 | 11/1998 |

(Continued)

OTHER PUBLICATIONS

U.S. Appl. No. 62/051,387, Flygare et al., filed Sep. 17, 2014.

(Continued)

*Primary Examiner* — Sheela J. Huff
(74) *Attorney, Agent, or Firm* — Casimir Jones, S.C.; Melissa E. Kolom

(57) ABSTRACT

Conjugates of an antibody that binds to CD19 with PBD dimers.

11 Claims, 3 Drawing Sheets

Specification includes a Sequence Listing.

(56) References Cited

U.S. PATENT DOCUMENTS

| | | |
|---|---|---|
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Howard et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,321,774 B2 | 4/2016 | Howard et al. |
| 9,376,440 B2 | 6/2016 | Howard et al. |
| 9,399,641 B2 | 7/2016 | Howard et al. |
| 9,415,117 B2 * | 8/2016 | Howard ............... C07D 487/04 |
| 9,624,227 B2 | 4/2017 | Howard et al. |
| 9,889,207 B2 * | 2/2018 | Howard ............... C07D 487/04 |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | DeVaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/0116422 A1 | 6/2006 | De Groot et al. |
| 2007/0072846 A1 | 3/2007 | Vishnuvajjala et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | Mcdonagh et al. |
| 2009/0149449 A1 | 6/2009 | Liu et al. |
| 2009/0304710 A1 | 12/2009 | Park et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2011/0091372 A1 | 4/2011 | Ghayur et al. |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0266595 A1 | 10/2013 | Flygare et al. |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0275522 A1 | 9/2014 | Howard et al. |
| 2014/0294868 A1 | 10/2014 | Howard et al. |

FOREIGN PATENT DOCUMENTS

| | | |
|---|---|---|
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 53-82792 | 7/1978 |
| JP | 57131791 | 8/1982 |
| JP | 58-180487 | 10/1983 |
| JP | 58180487 | 10/1983 |
| JP | 05003790 | 1/1993 |
| JP | 2004113151 | 4/2004 |
| WO | WO 1991/02536 | 3/1991 |
| WO | WO 1992/07574 | 5/1992 |
| WO | WO 1992/17497 | 10/1992 |
| WO | WO 1992/19620 | 11/1992 |
| WO | WO 1993/18045 | 9/1993 |
| WO | WO 1994/10312 | 5/1994 |
| WO | WO 1994/28931 | 12/1994 |
| WO | WO 1995/04718 | 2/1995 |

(56) References Cited

FOREIGN PATENT DOCUMENTS

| | | |
|---|---|---|
| WO | WO 1996/30514 | 10/1996 |
| WO | WO 1997/07198 | 2/1997 |
| WO | WO 1997/44452 | 11/1997 |
| WO | WO 1998/13059 | 4/1998 |
| WO | WO 1998/37193 | 8/1998 |
| WO | WO 1998/40403 | 9/1998 |
| WO | WO 1998/51805 | 11/1998 |
| WO | WO 1998/51824 | 11/1998 |
| WO | WO 1999/28468 | 6/1999 |
| WO | WO 1999/46284 | 9/1999 |
| WO | WO 1999/58658 | 11/1999 |
| WO | WO 2000/03291 | 1/2000 |
| WO | WO 2000/12130 | 3/2000 |
| WO | WO 2000/12506 | 3/2000 |
| WO | WO 2000/12507 | 3/2000 |
| WO | WO 2000/12508 | 3/2000 |
| WO | WO 2000/12509 | 3/2000 |
| WO | WO 2000/14228 | 3/2000 |
| WO | WO 2000/20579 | 4/2000 |
| WO | WO 2000/22129 | 4/2000 |
| WO | WO 2000/32752 | 6/2000 |
| WO | WO 2000/36107 | 6/2000 |
| WO | WO 2000/40614 | 7/2000 |
| WO | WO 2000/44899 | 8/2000 |
| WO | WO 2000/053216 | 9/2000 |
| WO | WO 2000/55351 | 9/2000 |
| WO | WO 2000/75655 | 12/2000 |
| WO | WO 2001/00244 | 1/2001 |
| WO | WO 2001/16318 | 3/2001 |
| WO | WO 2001/38490 | 5/2001 |
| WO | WO 2001/40269 | 6/2001 |
| WO | WO 2001/40309 | 6/2001 |
| WO | WO 2001/41787 | 6/2001 |
| WO | WO 2001/45746 | 6/2001 |
| WO | WO 2001/46232 | 6/2001 |
| WO | WO 2001/46261 | 6/2001 |
| WO | WO 2001/48204 | 7/2001 |
| WO | WO 2001/53463 | 7/2001 |
| WO | WO 2001/57188 | 8/2001 |
| WO | WO 2001/62794 | 8/2001 |
| WO | WO 2001/66689 | 9/2001 |
| WO | WO 2001/72830 | 10/2001 |
| WO | WO 2001/72962 | 10/2001 |
| WO | WO 2001/75177 | 10/2001 |
| WO | WO 2001/77172 | 10/2001 |
| WO | WO 2001/88133 | 11/2001 |
| WO | WO 2001/90304 | 11/2001 |
| WO | WO 2001/94641 | 12/2001 |
| WO | WO 2001/98351 | 12/2001 |
| WO | WO 2002/02587 | 1/2002 |
| WO | WO 2002/02624 | 1/2002 |
| WO | WO 2002/02634 | 1/2002 |
| WO | WO 2002/06317 | 1/2002 |
| WO | WO 2002/06339 | 1/2002 |
| WO | WO 2002/10187 | 2/2002 |
| WO | WO 2002/10382 | 2/2002 |
| WO | WO 2002/12341 | 2/2002 |
| WO | WO 2002/13847 | 2/2002 |
| WO | WO 2002/14503 | 2/2002 |
| WO | WO 2002/16413 | 2/2002 |
| WO | WO 2002/22153 | 3/2002 |
| WO | WO 2002/22636 | 3/2002 |
| WO | WO 2002/22660 | 3/2002 |
| WO | WO 2002/22808 | 3/2002 |
| WO | WO 2002/24909 | 3/2002 |
| WO | WO 2002/26822 | 4/2002 |
| WO | WO 2002/30268 | 4/2002 |
| WO | WO 2002/38766 | 5/2002 |
| WO | WO 2002/54940 | 7/2002 |
| WO | WO 2002/59377 | 8/2002 |
| WO | WO 2002/60317 | 8/2002 |
| WO | WO 2002/61087 | 8/2002 |
| WO | WO 2002/64798 | 8/2002 |
| WO | WO 2002/71928 | 9/2002 |
| WO | WO 2002/72596 | 9/2002 |
| WO | WO 2002/78524 | 10/2002 |
| WO | WO 2002/81646 | 10/2002 |
| WO | WO 2002/83866 | 10/2002 |
| WO | WO 2002/86443 | 10/2002 |
| WO | WO 2002/88170 | 11/2002 |
| WO | WO 2002/088172 | 11/2002 |
| WO | WO 2002/89747 | 11/2002 |
| WO | WO 2002/92836 | 11/2002 |
| WO | WO 2002/94852 | 11/2002 |
| WO | WO 2002/98358 | 12/2002 |
| WO | WO 2002/99074 | 12/2002 |
| WO | WO 2002/99122 | 12/2002 |
| WO | WO 2002/101075 | 12/2002 |
| WO | WO 2002/102235 | 12/2002 |
| WO | WO 2002/16429 | 1/2003 |
| WO | WO 2003/000842 | 1/2003 |
| WO | WO 2003/002717 | 1/2003 |
| WO | WO 2003/003906 | 1/2003 |
| WO | WO 2003/003984 | 1/2003 |
| WO | WO 2003/004529 | 1/2003 |
| WO | WO 2003/004989 | 1/2003 |
| WO | WO 2003/008537 | 1/2003 |
| WO | WO 2003/009814 | 2/2003 |
| WO | WO 2003/014294 | 2/2003 |
| WO | WO 2003/016475 | 2/2003 |
| WO | WO 2003/016494 | 2/2003 |
| WO | WO 2003/018621 | 3/2003 |
| WO | WO 2003/022995 | 3/2003 |
| WO | WO 2003/023013 | 3/2003 |
| WO | WO 2003/024392 | 3/2003 |
| WO | WO 2003/025138 | 3/2003 |
| WO | WO 2003/025148 | 3/2003 |
| WO | WO 2003/025228 | 3/2003 |
| WO | WO 2003/026493 | 4/2003 |
| WO | WO 2003/026577 | 4/2003 |
| WO | WO 2003/029262 | 4/2003 |
| WO | WO 2003/029277 | 4/2003 |
| WO | WO 2003/029421 | 4/2003 |
| WO | WO 2003/034984 | 5/2003 |
| WO | WO 2003/035846 | 5/2003 |
| WO | WO 2003/042661 | 5/2003 |
| WO | WO 2003/043583 | 5/2003 |
| WO | WO 2003/045422 | 6/2003 |
| WO | WO 2003/048202 | 6/2003 |
| WO | WO 2003/054152 | 7/2003 |
| WO | WO 2003/055439 | 7/2003 |
| WO | WO 2003/055443 | 7/2003 |
| WO | WO 2003/060612 | 7/2003 |
| WO | WO 2003/062401 | 7/2003 |
| WO | WO 2003/072035 | 9/2003 |
| WO | WO 2003/072036 | 9/2003 |
| WO | WO 2003/077836 | 9/2003 |
| WO | WO 2003/081210 | 10/2003 |
| WO | WO 2003/083041 | 10/2003 |
| WO | WO 2003/083047 | 10/2003 |
| WO | WO 2003/083074 | 10/2003 |
| WO | WO 2003/087306 | 10/2003 |
| WO | WO 2003/087768 | 10/2003 |
| WO | WO 2003/088808 | 10/2003 |
| WO | WO 2003/089624 | 10/2003 |
| WO | WO 2003/089904 | 10/2003 |
| WO | WO 2003/093444 | 11/2003 |
| WO | WO 2003/097803 | 11/2003 |
| WO | WO 2003/101283 | 12/2003 |
| WO | WO 2003/101400 | 12/2003 |
| WO | WO 2003/104270 | 12/2003 |
| WO | WO 2003/104275 | 12/2003 |
| WO | WO 2003/104399 | 12/2003 |
| WO | WO 2003/105758 | 12/2003 |
| WO | WO 2004/000221 | 12/2003 |
| WO | WO 2004/000997 | 12/2003 |
| WO | WO 2004/001004 | 12/2003 |
| WO | WO 2004/005598 | 1/2004 |
| WO | WO 2004/009622 | 1/2004 |
| WO | WO 2004/011611 | 2/2004 |
| WO | WO 2004/015426 | 2/2004 |
| WO | WO 2004/016225 | 2/2004 |
| WO | WO 2004/020583 | 3/2004 |
| WO | WO 2004/020595 | 3/2004 |

(56) References Cited

FOREIGN PATENT DOCUMENTS

| | | |
|---|---|---|
| WO | WO 2004/022709 | 3/2004 |
| WO | WO 2004/022778 | 3/2004 |
| WO | WO 2004/027049 | 4/2004 |
| WO | WO 2004/031238 | 4/2004 |
| WO | WO 2004/032828 | 4/2004 |
| WO | WO 2004/032842 | 4/2004 |
| WO | WO 2004/040000 | 5/2004 |
| WO | WO 2004/042346 | 5/2004 |
| WO | WO 2004/043361 | 5/2004 |
| WO | WO 2004/043963 | 5/2004 |
| WO | WO 2004/044178 | 5/2004 |
| WO | WO 2004/045516 | 6/2004 |
| WO | WO 2004/045520 | 6/2004 |
| WO | WO 2004/045553 | 6/2004 |
| WO | WO 2004/046342 | 6/2004 |
| WO | WO 2004/047749 | 6/2004 |
| WO | WO 2004/048938 | 6/2004 |
| WO | WO 2004/053079 | 6/2004 |
| WO | WO 2004/058309 | 7/2004 |
| WO | WO 2004/063355 | 7/2004 |
| WO | WO 2004/063362 | 7/2004 |
| WO | WO 2004/063709 | 7/2004 |
| WO | WO 2004/065576 | 8/2004 |
| WO | WO 2004/065577 | 8/2004 |
| WO | WO 2004/074320 | 9/2004 |
| WO | WO 2005/023814 | 3/2005 |
| WO | WO 2005/040170 | 5/2005 |
| WO | WO 2005/042535 | 5/2005 |
| WO | WO 2005/079479 | 9/2005 |
| WO | WO 2005/082023 | 9/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/044515 | 4/2007 |
| WO | WO 2007/085930 | 8/2007 |
| WO | WO 2008/010101 | 1/2008 |
| WO | WO 2008/022152 | 2/2008 |
| WO | WO 2008/047242 | 4/2008 |
| WO | WO 2008/070593 | 6/2008 |
| WO | WO 2009/016516 | 2/2009 |
| WO | WO 2009/052249 | 4/2009 |
| WO | WO 2009/117531 | 9/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2010/095031 | 8/2010 |
| WO | WO 2011/023883 | 3/2011 |
| WO | WO 2011/038159 | 3/2011 |
| WO | WO 2011/100227 | 8/2011 |
| WO | WO 2011/130598 | 10/2011 |
| WO | WO 2011/130613 | 10/2011 |
| WO | WO 2011/130615 | 10/2011 |
| WO | WO 2011/130616 | 10/2011 |
| WO | WO 2012/112687 | 8/2012 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2014/011518 | 1/2014 |
| WO | WO 2014/011519 | 1/2014 |
| WO | WO 2014/057072 | 4/2014 |
| WO | WO 2014/057073 | 4/2014 |
| WO | WO 2014/057074 | 4/2014 |
| WO | WO 2014/057117 | 4/2014 |
| WO | WO-2014057073 A1 * | 4/2014 ........... C07D 487/04 |
| WO | WO-2014057074 A1 * | 4/2014 ........... C07D 487/04 |
| WO | WO 2014/022679 | 6/2014 |

OTHER PUBLICATIONS

Adair, J.R. et al., "Antibody-drug conjugates—a perfect synergy," Exp. Opin. Biol. Ther. (2012) 16 pages.

Adams et al., "Molecular modelling of a sequence-specific DNA-binding agent based on the pyrrolo [2,1-c][1,4]benzodiazepines," Pharm. Pharmacol. Commun. (1999) 5:555-560.

Aird, R.E. et al., "ABCB1 genetic polymorphism influences the pharmacology of the new pyrrolobenzodiazepine derivative SJG-136," Pharmacogenomics Journal (2008) 8(4):289-296.

Alley, M.C. et al., "SJG-136 (NSC 694501), a novel rationally designed DNA minor groove interstrand crosslinking agent with potent and broad spectrum antitumor activity. Part 2: Efficacy evaluations," Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Antonow, D. et al., "Synthesis of DNA-Interactive Pyrrolo [2,1-c][1,4] benzodiazepines (PBDs)" Chemical Reviews, 2011, 111(4):2815-2864.

Antonow, D. et al., J Med. Chem., 2010, 53, 2927-2941.

Antonow, D. et al.,"Parallel synthesis of a novel C2-aryl pyrrolo [2,1-c] [1,4]benzodiazepine (PBD) library," J. Comb. Chem. (2007) 9:437-445.

Arai H., et al., "Molecular cloning of human endothelin receptors and their expressiOn in vascular endothelial cells and smooth muscle cells," Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chkl and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. (2006) 5(6):1602-1609.

Attie T., et al., "Mutation of the endothelin-receptor B gene in Waardenburg-Hirschsprung disease," Hum. Mol. Genet. 4, 2407-2409, 1995.

Auricchio A., et al., "Endothelin-B receptor mutations in patients with isolated Hirschsprung disease from a non-inbred population," Hum. Mol. Genet. 5:351-354, 1996.

Axup et al., Proc Natl Acad Sci U S A., 2012, 109(40):16101-16106.

Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.

(56) References Cited

OTHER PUBLICATIONS

Banker, G.S. et al., Modern Pharmaceutics, Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. lmmunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo [2,1-c][1,4]benzodiazepines," Tetrahedron Letters (2000) 41:6171-6174.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo [2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.
Brinster et al., "Introits increase transcriptional efficiency in transgenic mice," (1988) Proc. Natl. Acad. Sci. USA 85:836-840.
Buchman and Berg "Comparison of Intron-Dependent and Intron-Independent Gene Expression," (1988) Mol. Cell. Biol. 8:4395.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass. Spectrom. (2008) 43(1):42-52.
Cancer, 2012, http://wiki.answers.com/Q/How-many-different-types of cancer are there.
Cancer 2, 2012, http://en.wikipedia.org/wiki/Management of cancer.
Carl et al., "A Novel Connector Linkage Applicable in Prodrug Design," (1981) J. Med. Chem. 24:479-480.

Carlsson et al., "Protein Thiolation and Reversible Protein-Protein Conjugation," (1978) Biochem. J. 173:723-737.
Carper, P., "Potent antibody therapeutics by design," (2006) Nature Reviews Immunology 6:343-357.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodicola, A., et al., "Molecular characterization of a gene of the 'EGF family' expressed in undifferentiated human NTERA2 teratocarcinoma cells," EMBO J. 8 (7):1987-1991 (1989).
Cipolla, L., "Pyrrolo [2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.
Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo [2,1-c] [1,4]benzodiazepine dimer SJG-136 (NCS694501)," Proceedings of the American Association for Cancer Research Annual Meeting (Jul. 2003) 44:524.
Clingen, P.H., "The XPF-ERCC1 endonuclease and homologous recombination contribute to the repair of minor groove DNA interstrand crosslinks in mammalian cells produced by the pyrrolo [2,1-c][1,4]benzodiazepine dimer SJG-136," Nucl. Acids Res. (2005) 33(10):3283-3291.
Clinical Trial, 2011, http://www.nature.com/news/2011/110928/full/477526a.html.
Collins, "Generation and initial analysis of more than 15,000 full-length human and mouse eDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey E. Quinn JE, Buhler KR, et al., "LuCap35: a new model of prostate cancer progression to androgen independence." The Prostate 2003;55:239-46.
Courtney, S. M. et al., "A new convenient procedure for the synthesis of pyrrolo [2,1-c] [1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.

(56) References Cited

OTHER PUBLICATIONS

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use• of ATP bioluminescence as a measure of cell proliferation and cytotoxicity," (1993) J. Immunol. Meth. 160:81-88.

Dall'Acqua, W. F. et al., "Antibody humanization by framework shuffling" Methods, 36, 43-60 (2005).

Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

Davis et al., "Identification of a family of Fc receptor homo logs with preferential B cell expression," (2001) Proc. Natl. Acad. Sci. USA 98(17):9772-9777.

De Groot et al., ""Cascade-Release Dendrimers" Liberate All End Groups upon a Single Triggering Event in the Dendritic Core," (2003) Angew. Chem. Int. Ed. 42:4490-4494.

De Groot et al., "Elongated Multiple Electronic Cascade and Cyclization Spacer Systems in Activatible Anticancer Prodrug for Enhanced Drug Release," (2001) J. Org. Chern. 66:8815-8830.

Dennis et al., (2002) "Albumin Binding as a General Strategy for Improving the Pharmacokinetics of Proteins" J Biol Chem. 277:35035-35043.

Dijke, P., et al., "Characterization of Type I Receptors for Transforming Growth Factor-beta and Activin," Science 264 (5155):101-104 (1994).

Dobner et al., "Differentiation-specific expression of a novel G protein-coupled receptor from Burkitt's lymphoma," (1992) Eur. J. Immunol. 22:2795-2799.

Dong, Q. et al., "Reductive cleavage of TROC groups under neutral conditions with cadmium-lead couple," Tetrahedron Lett. (1995) 36(32):5681-5682.

Dono et al., "Isolation and Characterization of the CRI PTO Autosomal Gene and Its X-linked Related Sequence," Am. J. Hum. Genet. 49:555-565, 1991.

Dornan et al., "Therapeutic potential of an anti -CD79b antibody-drug conjugate, anti-CD79b-vc-MMAE, for the treatment of non-Hodgkin lymphoma," (2009) Blood 114(13):2721-2729.

Doronina et al., "Enhanced Activity of Monomethylauristatin F through Monoclonal Antibody Delivery: Effects of Linker Technology on Efficacy and Toxicity," (2006) Bioconj. Chem. 17:114-124.

Doronina, S.O. et al., "Development of potent monoclonal antibody auristatin conjugates for cancer therapy," Nature Biotech (2003) 21:778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.

Dubowchik et al, Bioorganic & Medicinal Chemistry Letters, 8:3341-3346, (1998).

Dubowchik et al, Bioorganic & Medicinal Chemistry Letters, 8:3347-3352, (1998).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.

Dubowchik, et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.

Dumoutier L., et al., "Cutting Edge: STAT Activation by IL-19, IL-20 and mda-7 Through IL-20 Receptor Complexes of Two Types," J. Immunol. 167, 3545-3549, 2001.

Dupont, C. et al., "Synthesis of rhazinilam analogue acting as an inhibitor of tubulin assembly," Tetrahedron Lett. (2000) 41:5853-5856.

Ehsani A., et al., "Characterization of a New Allele of the Human ERBB2 Gene by Allele-Specific Competition Hybridization," (1993) Genomics 15, 426-429.

Elshourbagy N.A., et al., "Molecular Characterization and Regulation of the Human Endothelin Receptors," J. Biol. Chem. 268, 3873-3879, 1993.

Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.

Farmer, J.D. et al., "Synthesis and DNA crosslinking ability of a dimeric anthramycin analog," Tetrahedron Letters (1988) 29(40):5105-5108, Abstract only.

Farmer, J.D. et al., "DNA binding properties of a new class of linked anthramycin analogs,", Chemical Abstracts, Abstract No. 239940r, vol. 114, No. 25, 25 899-903 (1991).

Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.

Fey, T. et al., "Silica-supported TEMPO catalyst: synthesis and application in the anelli oxidation of alcohols," J. Org. Chem. (2001) 66:8154-8159.

Fields, G. and Noble, R. (1990) "Solid phase peptide synthesis utilizing 9-fluoroenylmethoxycarbonyl amino acids", Int. J. Peptide Protein Res. 35:161-214.

Firsching, A. et al., "Antiproliferative and angiostatic activity of suramin analogues," Cancer Res. (1995) 55:4957-4961.

Flanagan et al., "The Ephrins and EPH Receptors in Neural Development," Annu. Rev. Neurosci. 21:309-345 (1998).

Foloppe, M.P. et al., "DNA-binding properties of pyrrolo[2,1-c][1,4]benzodiazephine N10-C11 amidines," Eur. J. Med. Chem., 31, 407-410 (1996).

Fox et al., "cDNA cloning and tissue distribution of five human EPH-like receptor protein-tyrosine kinases," Oncogene 10 (5):897-905 (1995).

Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.

Fujisaku et al., "Genomic Organization and Polymorphisms of the Human C3d/Epstein-Barr Virus Receptor," (1989) J. Biol. Chem. 264 (4):2118-2125.

Fujisawa Pharmaceutical Co. Ltd., "Benzodiazepine derivatives," SciFinder Scholar, 2-3 (2002).

Fujisawa Pharmaceutical Co., Ltd., Abstract No. 139983k, " Benzodiazepine derivatives", Chemical Abstracts, vol. 99, No. 17, 603 (1983).

Fujisawa Pharmaceutical Co., Ltd., Abstract No. 72145x, "Benzodiazepine derivatives", Chemical Abstracts, vol. 98, No. 9, 638 (1983).

Fukuyama, T. et al., "Total Synthesis of (+)-Porothramycin B," Tetrahedron Letters, vol. 34, 16, 2577-2580 (1993).

Gallmeier, E., "Targeted disruption of FANCC and FANCG in human cancer provides a preclinical model for specific therapeutic options," Gastroenterology (2006) 130(7):2145-2154.

Gary S.C., et al., "cDNA cloning chromosomal localization, and expression analysis of human BEHAB/brevican, a brain specific proteoglycan regulated during cortical development and in glioma," Gene 256, 139-147, 2000.

Gaugitsch, H.W., et al., "A Novel Transiently Expressed, Integral Membrane Protein Linked to Cell Activation. Molecular Cloning Via the Rapid Degradation Signal AUUUA," (1992) J. Biol. Chem. 267 (16):11267-11273.

Gavezzotti, A., "Are crystal structures predictable?" Acc. Chem. Res. (1994) 27:309-314.

Geiser et al "Automation of solid-phase peptide synthesis" in Macromolecular Sequencing and Synthesis, Alan R. Liss, Inc., 1988, pp. 199-218.

Genbank accession No. 11038674 (2013).

(56) References Cited

OTHER PUBLICATIONS

Genbank accession No. 20 NM_006424 (2013).
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP_001194 (2013).
Genbank accession No. NP_001774.10 (2013).
Genbank accession No. NP_003203 (2013).
Genbank accession No. NP 002111.1 (2013).
Genbank accession No. NP_001171569.1 (1992).
Genbank accession No. NP_001707.1 (2013).
Genbank accession No. NP_001773.1 (2013).
Genbank accession No. NP_002552.2 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, A Proteogl YCAN Identified in Prostate Cancer That Is Associated With Disease Progression and Androgen Independence," (2001) Int J Cancer. Oct 15; 94(2): 178-184.
Gordon et al., "Somatic hypermutation of the B cell receptor genes 829 (1g13, CD79b) and mbl (lga, CD79a)," PNAS, Apr. 1, 2003, vol. 100, No. 7, 4126-4131.

Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 23-200, 503-549, 633-647.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo [2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo [2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "Molecular Cloning and Expression Pattern of a Human Gene Homologous to the Murine mb-1 Gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Hamaguchi, A., "DNA cross-linking and in vivo antitumour activity of the extended pyrrolo [2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Hara et al., "DC 102, a new glycosidic pyrrolo(1,4)benzodiazepine antibiotic produced by *Streptomyces* sp.", J. Antibiotics, 41, 702-704 (1988).

(56) References Cited

OTHER PUBLICATIONS

Hartley J A: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand crosslinking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4 ):287-295.
Hay et al., "A 2-Nitroimidazole Carbamate Prodrug of 5-Amin0-1-(Chloromethyl)-3-[(5,6,7-Trimethoxyindol-2-Yl)Carbonyl]-1,2-Dihydr0-3H-Benz[E]Indole (Amino-Seco-CBI-TMI) for Use With Adept and Gdept," (1999) Bioorg. Med. Chern. Lett. 9:2237-2242.
Herdwijn et al., "Synthesis of trans(+ )6-phenoxyacetamido-1-methylene-3,3-dicarboxymethyl-1-calbapenam," Canadian Journal of Chemistry. 1982, 60, 2903-2907.
Hermanson, G.T., "Heterobifunctional Cross-linkers," (1996) Bioconjugate Techniques; Academic Press: New York, p. 234-242.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)," Eur. J. Hum. Genet. 5, 180-185, 1997.
Hofstra R.M.W., et al., "Mutations in Hirschsprung Disease: When Does a Mutation Contribute to the Phenotype," Nat. Genet. 12, 445-447, 1996.
Horie et al., "Identification and Characterization of TMEFF2, a Novel Surviv Factor for Hippocampal and Mesencephalic Neurons," (2000) Genornics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo [2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo [2,1-c][1,4]benzodiazepine dimers," EJC Supplements (2006) 4(12):95—Poster Abstract 301.
Howard, P.W., "Design, synthesis and biological evaluation of novel C2-aryl-substituted pyrrolo [2,1-c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Ide et al., "Cloning of human bone morphogenetic protein type IB receptor (BMPRIB) and its expression in prostate cancer in comparison with other BMPRs," Oncogene (1997) 14, 1377-1382.
Itoh et al., "Sibanomicin, a new pyrrolo(1,4)benzodiazepine antitumor antibiotic produced by a *micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey et al., Bioconjugate Chemistry, 5, 2006, 17, 831-840.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1,2-unsaturated pyrrolobenzodiazepine," Chem. Commun. (2003) 1688-1689.

(56) References Cited

OTHER PUBLICATIONS

Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chern. 27:1447-1451.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kunimoto et al., "Mazethramycin, a new member of anthramycin group antibiotics," J. Antibiotics, 33, 665-667 (1980).
Kurebayashi et al., "Isolation and characterization of a new human breast cancer cell line, KPL-4, expressing the Erb B family receptors and interleukin.6," (1999) Brit. Jour. Cancer 79(5-6):707-717.
Lambert J., "Drug-conjugated monoclonal antibodies for the treatment of cancer," (2005) Current Opin. in Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+-Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leber, J.D. et al., "A revised structure for sibiromycin," J. Am. Chem. Soc., 110, 2992-2993 (1988).
Leimgruber, W. et al., "Isolation and characterization of anthmmycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Levenson et al., "MCF-7: The First Hormone-responsive Breast Cancer Cell Line," (1997) Cancer Res. 57(15):3071-3078.

Liang et al., "The Gene for a Novel Transmembrane Protein Containing Epidermal Growth Factor and Follistatin Domains is Frequently Hypermethylated in Human Tumor Cells," (2000) Cancer Res. 60:4907-4912.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo [2,1-c][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Mastroberardino et al., "Amino-acid transport by heterodimers of 4F2hc/CD98 and members of a permease family," Nature 395 (6699):288-291 (1998).
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "RP1OS Is Associated With MD-1 and Transmits an Activation Signal in Human B Cells," (1996) Genomics 38(3):299-304.
Miura et al., "RP1OS Is Associated With MD-1 and Transmits an Activation Signal in Human B Cells," (1998) Blood 92:2815-2822.
Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. lmmunol. 22 (6): 1621-1625.
Mungall A.J., et al., "The DNA sequence and analysis of human chromosome 6," Nature 425, 805-811, 2003.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).

(56) References Cited

OTHER PUBLICATIONS

Nagase T., et al., "Prediction of the Coding Sequences of Unidentified Human Genes. XVII. The Complete Sequences of 100 New cDNA Clones from Brain Which Code for Large Proteins in vitro," (2000) DNA Res. 7(2):143-150.
Nakamuta M., et al., "Cloning and Sequence Analysis of a cDNA Encoding Human Non-Selective Type of Endothelin Receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastmnd cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin 01: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human EndothelinB," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Parrish-Novak J., et al., "lnterleukins 19, 20, and 24 Signal through Two Distinct Receptor Complexes," J. Biol. Chem. 277, 47517-47523, 2002.
Payne, G. "Progress in immunoconjugate cancer therapeutics," (2003) Cancer Cell 3:207-212.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.

Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudoobstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Sagnou, M.J. et al., "Design and Synthesis of Novel Pyrrolobenzodiazepine (PBD) Prodrugs for ADEPT and GDEPT," Bioorganic & Medicinal Chemistry Letters, 10, 2083-2086 (2000).

(56) References Cited

OTHER PUBLICATIONS

Sakaguchi et al., "8 lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene Is a Divergent Member of the Class II P Gene Family," (1987) J. Biol. Chem. 262:8759-8766.
Shamis et al., "Bioactivation of Self-lmmolative Dendritic Prodrugs by Catalytic Antibody 38C2," (2004) J . Am. Chem. Soc. 126:1726-1731.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu et al., "Prothracarcin, a novel antitumor antibiotic," The Journal of Antibiotics (1982) 29, 2492-2503.
Shimizu, K et al., "Prothracarcin, a Novel Antitumor Antibiotic," J Antibiotics, 35, 972-978 (1982).
Sinha S.K., et al., "Characterization of the EBV /C3d Receptor on the Human Jurkat T Cell Line: Evidence for a Novel Transcript," (1993) J.Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., Anal. Biochem., 1985, 150(1): 76-85.
Souillac, P. et al., "Chracterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.

Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Tawaragi Y., et al., "Primary Structure of Nonspecific Crossreacting Antigen (Nca), a Member of Carcinoembryonic Antigen (CEA) Gene Family, Deduced From cDNA Sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson, J.S., et al., "BAFF-R, a Newly Identified TNF Receptor That Specifically Interacts with BAFF," Science 293 (5537), 2108-2111 (2001 ).
Thurston, D. E., "Advances in the study of Pyrrolo [2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo [2,1-c] [1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo [2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DOBeta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol Immunother. 52:328-337.

(56) References Cited

OTHER PUBLICATIONS

Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a Human Protein Homologous to the Mouse Lyb-2 B Cell Differentiation Antigen and Sequence of the Corresponding cDNA," (1990) J. Immunol 144(12):4870-4877.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the Human B Lymphocyte Receptor for C3d and the Epstein-Barr Virus and Relatedness to Other Members of the Family of C3/C4 Binding Proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wilkinson, "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking-agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,-c][1,4]benzodiazepine System", J. Med. Chem. 42-4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.
Xie et al., "In vivo behaviour of antibody-drug conjugates for the targeted treatment of cancer," (2006) Expert. Opin Biol. Ther. 6(3):281-291.
Xie, G. et al., "Bisindolylmaleimides linked to DNA minor groove binding lexitropsins: synthesis, inhibitory activity against topoisomeraseI, and biological evaluation," J. Med. Chem. (1996) 39:1049-1055.
Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).
Xu, M.J., et al., "Molecular Cloning and Characterization of SPAP1, an Inhibitory Receptor," (2001) Biochem. Biophys. Res. Commun. 280 (3):768-775.
Xu, X.Z., et al., "Regulation of melastatin, a TRP-related protein, through interaction with a cytoplasmic isoform," Proc. Natl. Acad. Sci. U.S.A. 98 (19):10692-10697 (2001).
Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).
Yamamoto T., et al., "Similarity of protein encoded by the human c-elb-B-2 gene to epidermal growth factor receptor," Nature 319, 230-234, 1986.
Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.
Yin & Lloyd, "Molecular Cloning of the CA125 Ovarian Cancer Antigen," J. Biol. Chem. 276 (29):27371-27375 (2001).
Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.
Yu et al., "Human mb-1 Gene: Complete eDNA Sequence and Its Expression in B Cells Bearing Membrane Ig of Various Isotypes," (1992) J. Immunol. 148(2) 633-637.
International Search Report and Written Opinion for Application No. PCT/EP2012/070233 dated Jan. 28, 2013 (8 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/EP2013/071346 dated Feb. 5, 2014 (13 pages).
Zammarchi et al., "Pre-Clinical Development of Adct-402, a Novel Pyrrolobenzodiazepine (PBD)-Based Antibody Drug Conjugate (ADC) Targeting CD19-Expressing B-Cell Malignancies," Blood, 2015, 126:1564, Abstract.
Brand et al., Prospect for anti-HER2 receptor therapy in breast cancer. Anticancer Res. Jan.-Feb. 2006;26(1B):463-70.
Johnson & Goldin, "The clinical impact of screening and other experimental tumor studies." Cancer Treat Rev. Mar. 1975;2(1):1-31.
Paul, Fundamental Immunology, 3$^{rd}$ Edition, pp. 292-295, (1993).
Rudikoff et al., Single amino acid substitution altering antigen-binding specificity. Proc Natl Acad Sci U S A. Mar. 1982; 79(6):1979-83.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Casset et al., "A peptide mimetic of an anti-CD4 monoclonal antibody by rational design." Biochem Biophys Res Commun. Jul. 18, 2003; 307(1):198-205.

\* cited by examiner

PYRROLOBENZODIAZEPINE-ANTIBODY CONJUGATES

CROSS-REFERENCE TO RELATED APPLICATIONS

This application is a Continuation of U.S. patent application Ser. No. 14/434,816 filed Apr. 10, 2015, which is a 35 U.S.C. § 371 National Stage Entry of International Application No. PCT/EP2013/071346 having an international filing date of Oct. 11, 2013, which claims the benefit of U.S. Provisional Patent Application Nos. 61/784,362, 61/784,421, and 61/784,383 all filed Mar. 14, 2013, and U.S. Provisional Patent Application Nos. 61/712,924 and 61/712,928 both filed Oct. 12, 2012, the contents of which are incorporated herein by reference in their entirety.

The present invention relates to pyrrolobenzodiazepines (PBDs) having a labile C2 or N10 protecting group in the form of a linker to an antibody.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

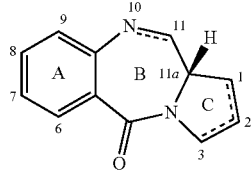

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

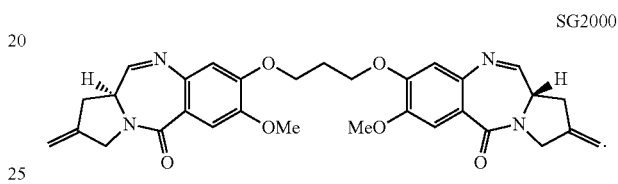

WO 2007/085930 describes the preparation of dimer PBD compounds having linker groups for connection to a cell binding agent, such as an antibody. The linker is present in the bridge linking the monomer PBD units of the dimer.

The present inventors have described dimer PBD compounds having linker groups for connection to a cell binding agent, such as an antibody, in WO 2011/130613 and WO 2011/130616. The linker in these compounds is attached to the PBD core via the C2 position, and are generally cleaved by action of an enzyme on the linker group. In WO 2011/130598, the linker in these compounds is attached to one of the available N10 positions on the PBD core, and are generally cleaved by action of an enzyme on the linker group.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6):3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) *Blood* 114(13):2721-2729; U.S. Pat. Nos. 7,521,541; 7,723, 485; WO2009/052249; McDonagh (2006) *Protein Eng. Design & Sel.* 19(7): 299-307; Doronina et al (2006) *Bioconj. Chem.* 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

The present inventors have developed particular PBD dimer antibody conjugates.

DISCLOSURE OF THE INVENTION

Figure 1:
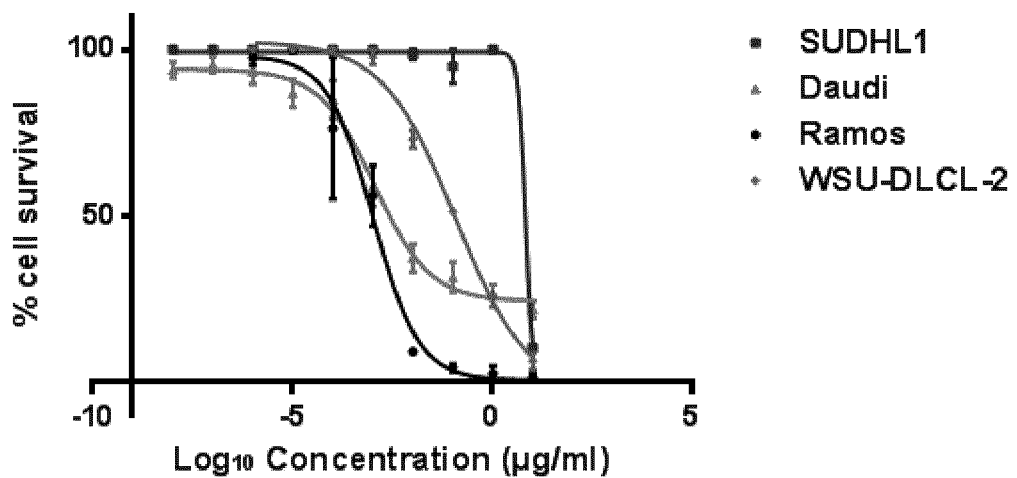
FIG. 1 shows the in vitro efficacy of a conjugate of the invention against Daudi, Ramos and WSU-DLCL2 cells.

A first aspect of the present invention comprises a conjugate of formula L-(D$^L$)$_p$, where D$^L$ is of formula I or II:

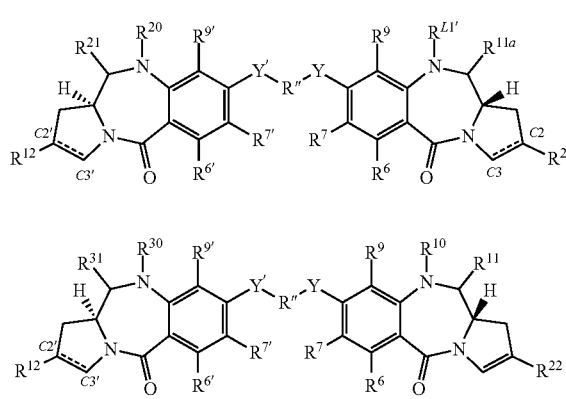

wherein:

L is an antibody (Ab) as defined below;

when there is a double bond present between C2' and C3', $R^{12}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

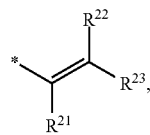

(id)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

wherein one of $R^{25a}$ and $R^{25b}$ is H and the other is selected from: phenyl, which phenyl is optionally substituted by a group selected from halo, methyl, methoxy; pyridyl; and thiophenyl; and

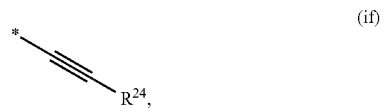

(if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

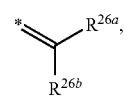

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, NH$_2$, NHR, NRR', nitro, Me$_3$Sn and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, NH$_2$, NHR, NHRR', nitro, Me$_3$Sn and halo;

R" is a $C_{3-12}$ alkylene group, which chain may be interrupted by one or more heteroatoms, e.g. O, S, NR$^{N2}$ (where R$^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

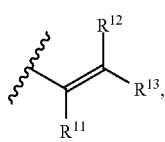

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

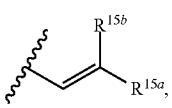

wherein one of $R^{15a}$ and $R^{15b}$ is H and the other is selected from: phenyl, which phenyl is optionally substituted by a group selected from halo, methyl, methoxy; pyridyl; and thiophenyl; and (if)

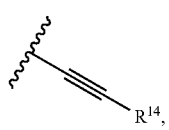

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

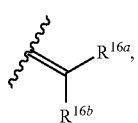

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

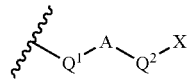

where A is a $C_{5-7}$ aryl group, and either (i) $Q^1$ is a single bond, and $Q^2$ is selected from a single bond and —Z—$(CH_2)_n$—, where Z is selected from a single bond, O, S and NH and n is from 1 to 3; or (ii) $Q^1$ is —CH=CH—, and $Q^2$ is a single bond;

(b)

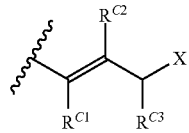

where;

$R^{C1}$, $R^{C2}$ and $R^{C3}$ are independently selected from H and unsubstituted $C_{1-2}$ alkyl;

(c)

where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

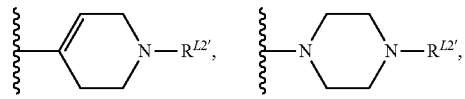

$NR^NR^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_zM$;

$R^{30}$ and $R^{31}$ either together form a double bond between the nitrogen and carbon atoms to which they are bound or;

$R^{30}$ is H and $R^{31}$ is selected from OH, $OR^A$ and $SO_zM$.

In some embodiments, the conjugate is not:
ConjA
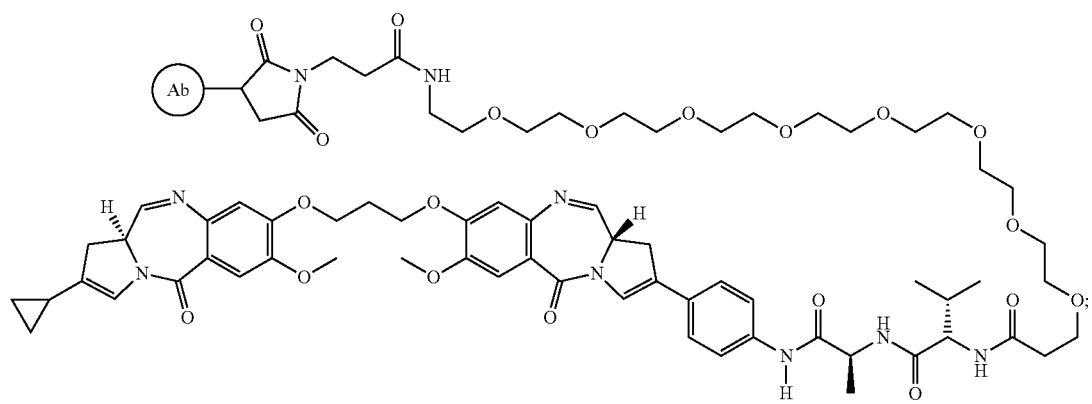
ConjB
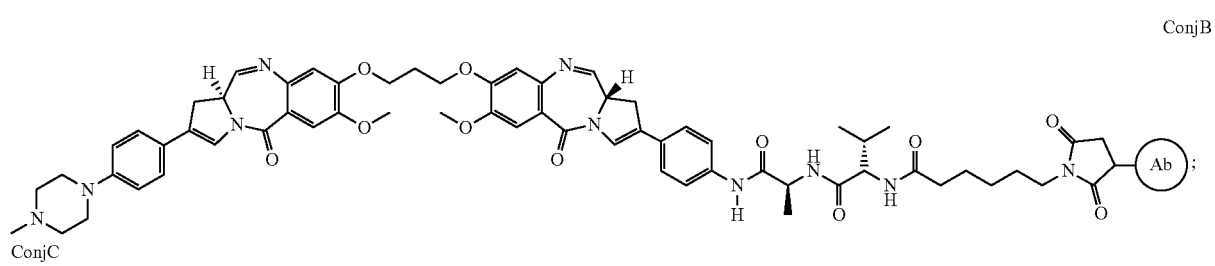
ConjC
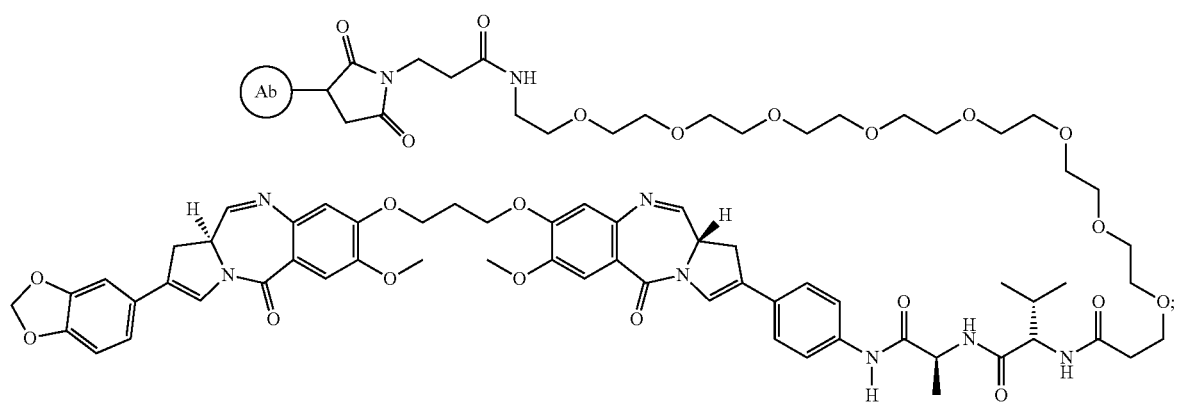
ConjD
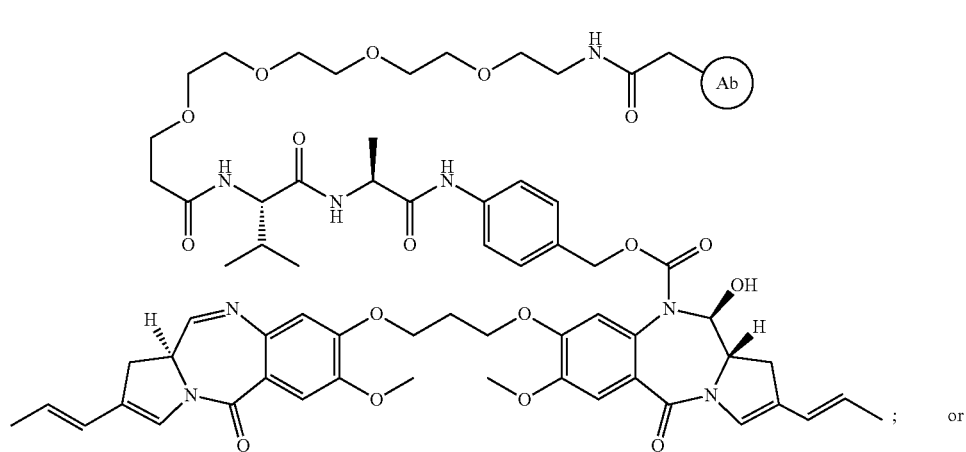
; or -continued ConjE

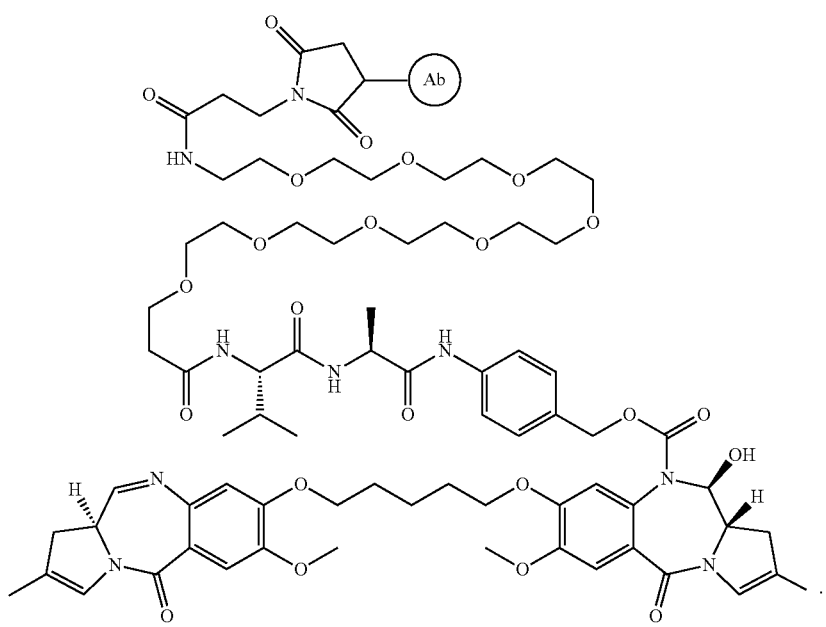

ConjE

In other embodiments, it may be preferred that the conjugate is selected from a conjugate of formula ConjA, ConjB, ConjC, ConjD and ConjE.

The subscript p in the formula I is an integer of from 1 to 20. Accordingly, the Conjugates comprise an antibody (Ab) as defined below covalently linked to at least one Drug unit by a Linker unit. The Ligand unit, described more fully below, is a targeting agent that binds to a target moiety. Accordingly, the present invention also provides methods for the treatment of, for example, various cancers and autoimmune disease. The drug loading is represented by p, the number of drug molecules per antibody. Drug loading may range from 1 to 20 Drug units ($D^L$) per antibody. For compositions, p represents the average drug loading of the Conjugates in the composition, and p ranges from 1 to 20.

A second aspect of the invention provides a method of making a conjugate according to the first aspect of the invention comprising conjugating a compound of formula $I^L$ or $II^L$:

$I^L$
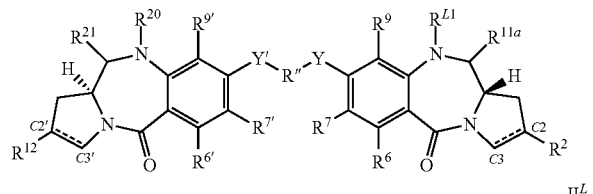

$II^L$
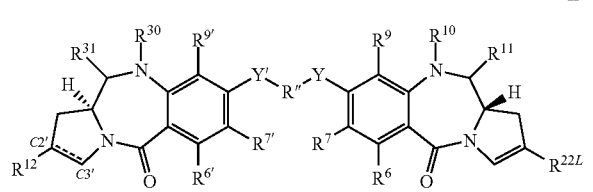

to the antibody (Ab) as defined below, wherein:
$R^{L1}$ is a linker suitable for conjugation to the antibody (Ab);
$R^{22L}$ is of formula $IIIa^L$, formula $IIIb^L$ or formula $IIIc^L$:

(a)

IIIa

(b)

IIIb

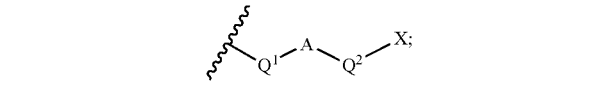

(c)

IIIc

where $Q^L$ is selected from $O-R^{L2}$, $S-R^{L2}$ and $NR^N-R^{L2}$, and $R^N$ is selected from H, methyl and ethyl
$X^L$ is selected from the group comprising: $O-R^{L2}$, $S-R^{L2}$, $CO_2-R^2$, $CO-R^{L2}$, $N=C=O-R^{L2}$, $NHNH-R^L$, $CONHNH-R^{L2}$, $NR^N R^L$, herein $R^N$ is selected from the group comprising H and $C_{1-4}$ alkyl;
$R^{L2}$ is a linker suitable for conjugation to the antibody (Ab); and all the remaining groups are as defined in the first aspect.

Thus it may be preferred in the second aspect, that the invention provides a method of making a conjugate selected from the group consisting of ConjA, ConjB, ConjC, ConjD and ConjE comprising conjugating a compound which is selected respectively from A:
A
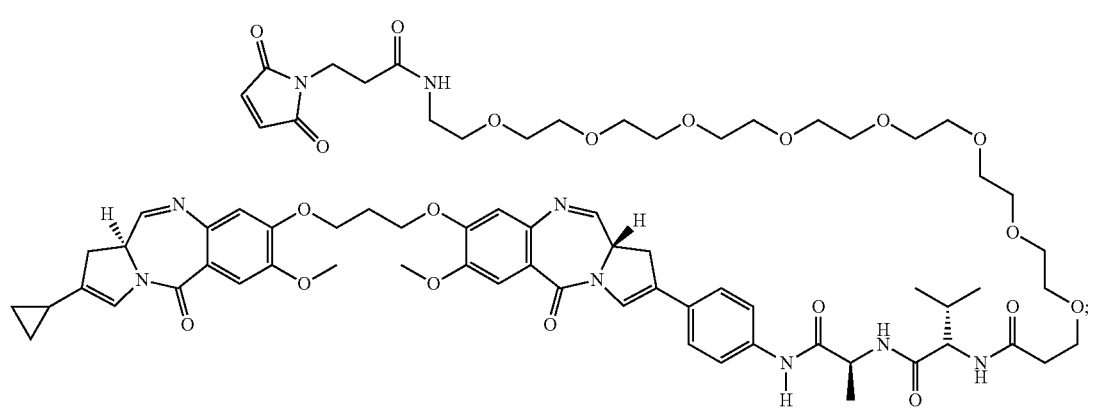
B
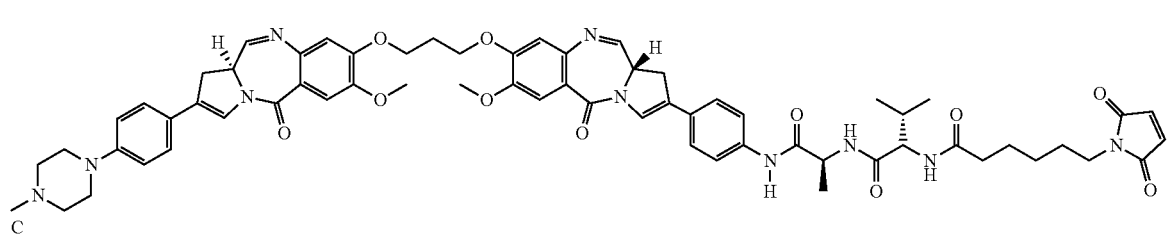
C
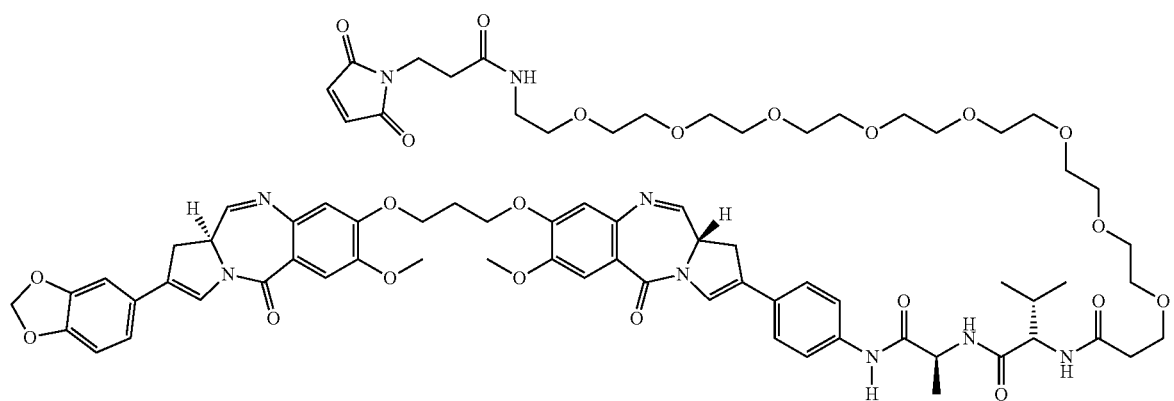
D
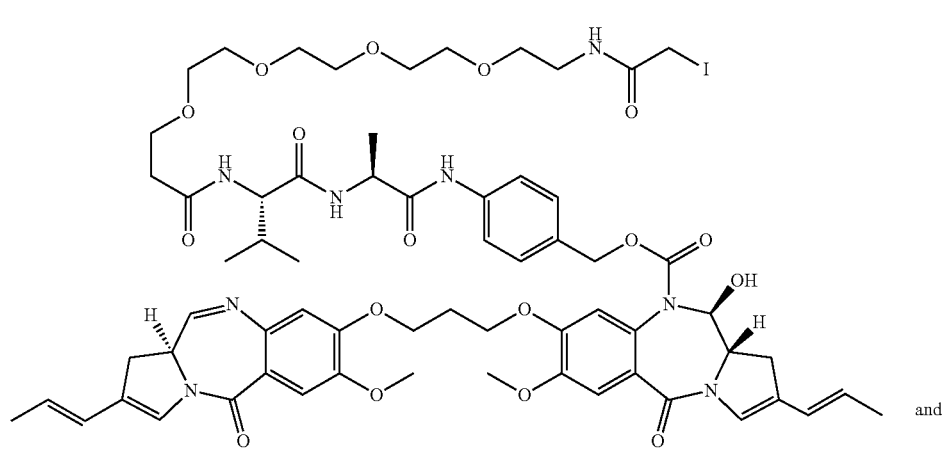
and E
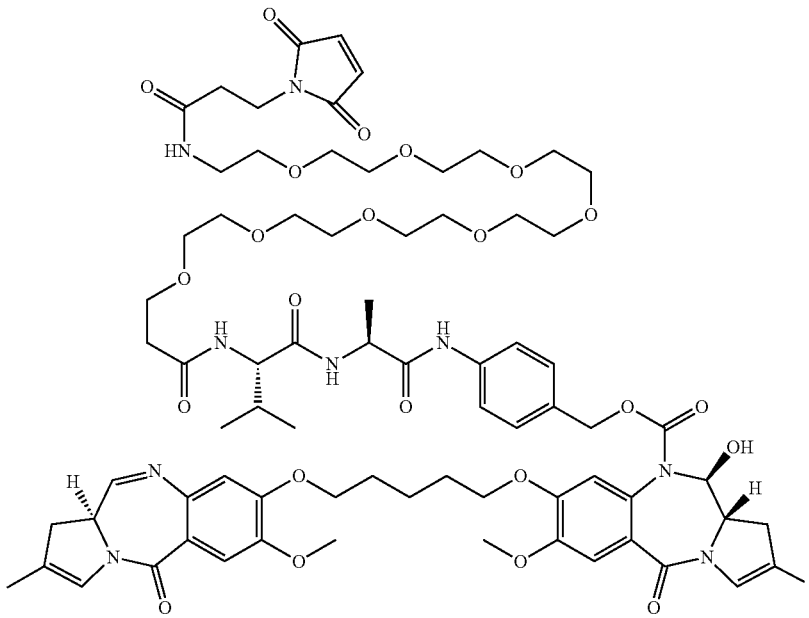
with an antibody as defined below.
WO 2011/130615 discloses compound 26:
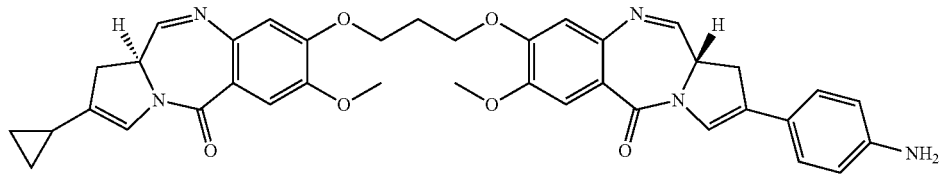
which is the parent compound of A. Compound A comprises this PBD with a linker for attachment to a cell binding agent. The cell binding agent provides a number of ethylene glycol moieties to provide solubility which is useful in the synthesis of conjugates.
WO 2010/043380 and WO 2011/130613 disclose compound 30:
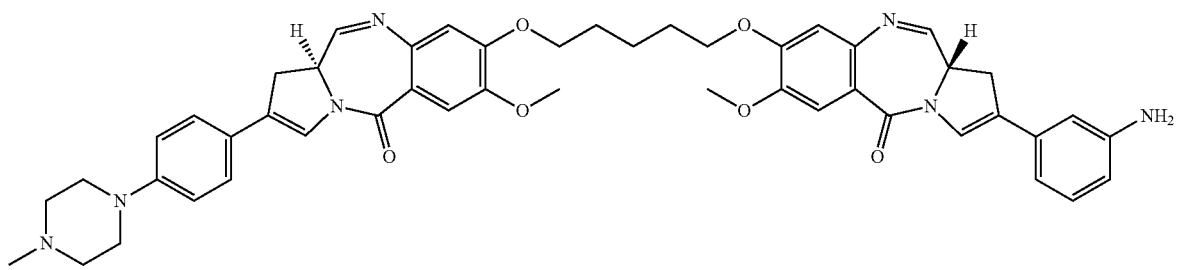

WO 2011/130613 also discloses compound 51:

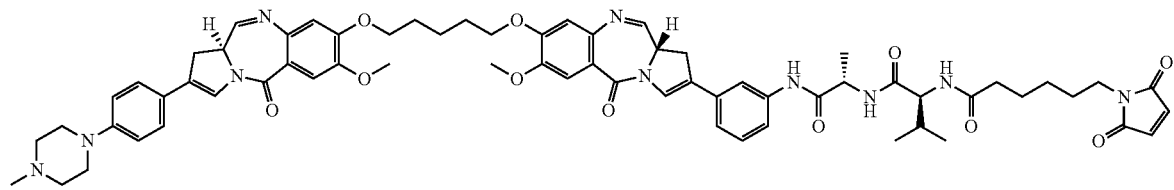

30

Compound B differs from compound 30 by only having a (CH$_2$)$_3$ tether between the PBD moieties, instead of a (CH$_2$)$_5$ tether, which reduces the lipophilicity of the released PBD dimer. The linking group is attached to the C2-phenyl group in the para rather than meta position.

WO 2011/130613 discloses compound 93:

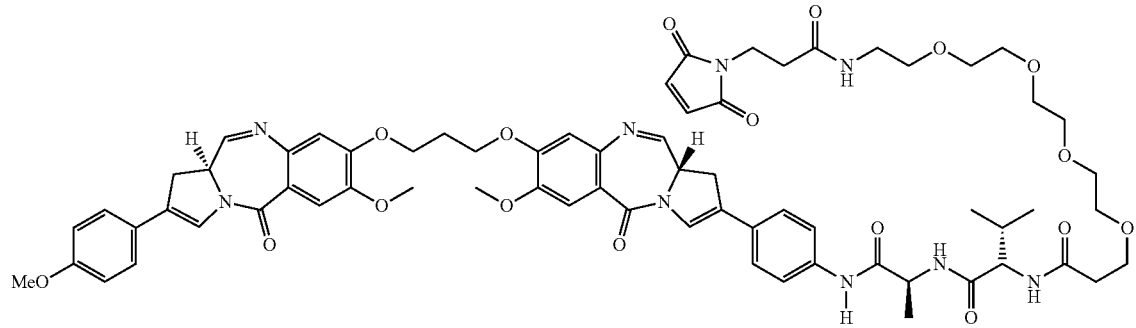

93

Compound C differs from this in two respects. The cell binding agent provides an increased number of ethylene glycol moieties to provide solubility which is useful in the synthesis of conjugates, and the phenyl substituent provide two rather than one oxygen atom, which also aids solubility. Compound C's structure may also mean it binds more strongly in the minor groove.

Compounds A, B and C have two sp$^2$ centres in each C-ring, which may allow for stronger binding in the minor groove of DNA, than for compounds with only one sp$^2$ centre in each C-ring.

WO 2011/130598 discloses compound 80:

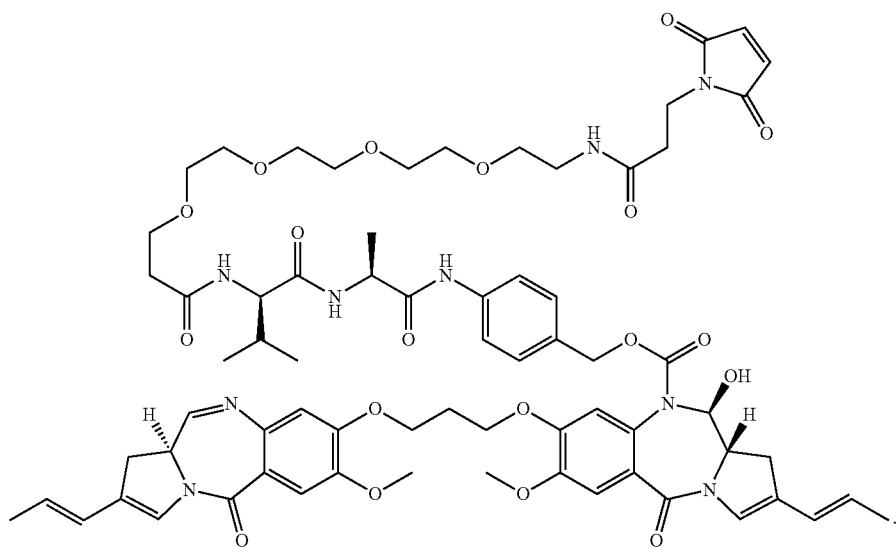

80

Compound D differs from this by comprising an iodoacetamide group for linking to the cell binding agent. This group may offer advantages over compound 80 with regards to its stability when bound to a cell binding agent (see below). The malemide group in compound 80 can undergo a retro-Michael reaction, becoming unconjugated from the cell binding agent, and thus vunerable to scavenging by other thiol containing biological molecules, such as albumin and glutathione. Such unconjugation cannot occur with compound A. Also, the iodoacetamide group may avoid other unwanted side reactions.

Compound E differs from previously disclosed PBD dimers with a drug linker having a C2-3 endo-double bond, by having a smaller, less lipophilic C2 substituent, e.g. 4F-phenyl, propylene. As such, the conjugates of compound B (see below) are less likely to aggregate once synthesised. Such aggregation of conjugates can be measured by Size exclusion chromatography (SEC).

Both compound D and E have two $sp^2$ centres in each C-ring, which may allow for stronger binding in the minor groove of DNA, than for compounds with only one $sp^2$ centre in each C-ring.

The drug linkers disclosed in WO 2010/043880, WO 2011/130613, WO 2011/130598 and WO 2011/130616 may be used in the present invention, and are incorporated herein by reference. The drug linkers described herein may be synthesised as described in these disclosures.

DETAILED DESCRIPTION OF THE INVENTION

The present invention is suitable for use in providing a PBD compound to a preferred site in a subject. The conjugate allows the release of an active PBD compound that does not retain any part of the linker. There is no stub present that could affect the reactivity of the PBD compound. Thus ConjA would release the compound RelA:

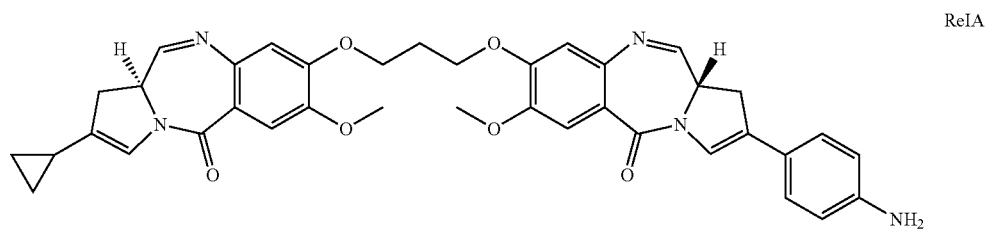 [SMILES: COc1cc2c(cc1OCCCOc1cc3c(cc1OC)C(=O)N1C=C(C4CC4)C[C@H]1C=N3)N=C[C@@H]1CC(c3ccc(N)cc3)=CN1C2=O]

RelA

ConjB would release the compound RelB:

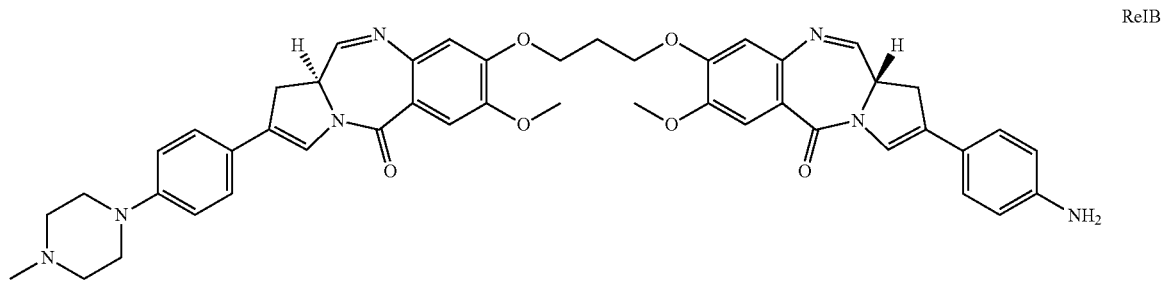 [SMILES: COc1cc2c(cc1OCCCOc1cc3c(cc1OC)C(=O)N1C=C(c4ccc(N5CCN(C)CC5)cc4)C[C@H]1C=N3)N=C[C@@H]1CC(c3ccc(N)cc3)=CN1C2=O]

RelB

ConjC would release the compound RelC:

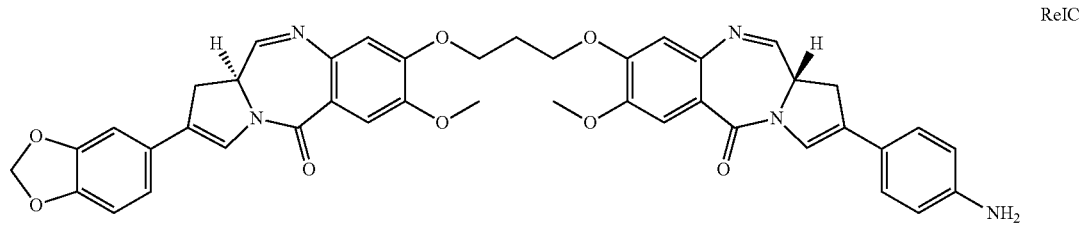 [SMILES: COc1cc2c(cc1OCCCOc1cc3c(cc1OC)C(=O)N1C=C(c4ccc5c(c4)OCO5)C[C@H]1C=N3)N=C[C@@H]1CC(c3ccc(N)cc3)=CN1C2=O]

RelC

ConjD would release the compound RelD:

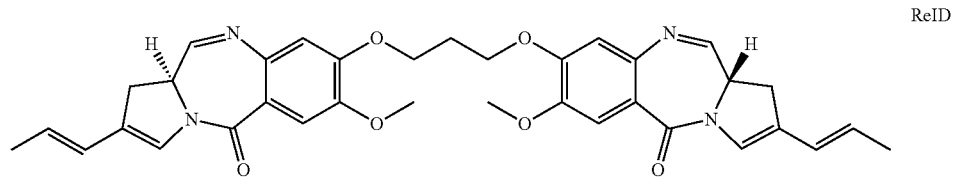 [SMILES: C/C=C/C1=CN2C(=O)c3cc(OC)c(OCCCOc4cc5c(cc4OC)C(=O)N4C=C(/C=C/C)C[C@H]4C=N5)cc3N=C[C@@H]2C1]

RelD and ConjE would release the compound RelE:

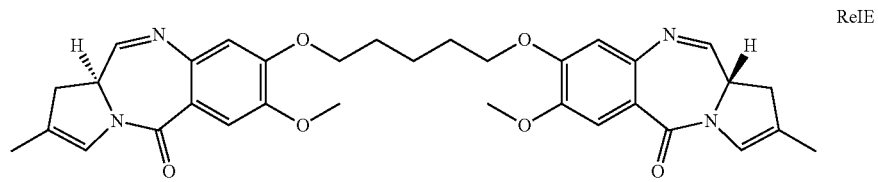

RelE

The specified link between the PBD dimer and the antibody, in the present invention is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA, RelB, RelC, RelD or RelE is achieved at the desired activation site of the conjugates of formulae ConjA, ConjB, ConjC, ConjD or ConjE by the action of an enzyme, such as cathepsin, on the linking group, and in particular on the valine-alanine dipeptide moiety.

Antibody in one aspect the antibody is an antibody that binds to CD19, the antibody comprising a VH domain having the sequence according to any one of SEQ ID NOs. 1, 2, 3, 4, 5 or 6.

The antibody may further comprise a VL domain. In some embodiments the antibody further comprises a VL domain having the sequence according to any one of SEQ ID NOs. 7, 8, 9, 10, 11 or 12.

In some embodiments the antibody comprises a VH domain paired with a VL domain, the VH and VL domains having sequences selected from the group consisting of:
SEQ ID NO. 1 paired with any one of SEQ ID NOs. 7, 8, 9, 10, 11 or 12;
SEQ ID NO. 2 paired with any one of SEQ ID NOs. 7, 8, 9, 10, 11 or 12;
SEQ ID NO. 3 paired with any one of SEQ ID NOs. 7, 8, 9, 10, 11 or 12;
SEQ ID NO. 4 paired with any one of SEQ ID NOs. 7, 8, 9, 10, 11 or 12;
SEQ ID NO. 5 paired with any one of SEQ ID NOs. 7, 8, 9, 10, 11 or 12; and
SEQ ID NO. 6 paired with any one of SEQ ID NOs. 7, 8, 9, 10, 11 or 12. For example SEQ ID NO. 1 paired with SEQ ID NO. 7, SEQ ID NO. 2 paired with SEQ ID NO. 8, SEQ ID NO. 3 paired with SEQ ID NO. 9, SEQ ID NO. 4 paired with SEQ ID NO. 10, SEQ ID NO. 5 paired with SEQ ID NO. 11 or SEQ ID NO. 6 paired with SEQ ID NO. 12.

The VH and VL domain(s) may pair so as to form an antibody antigen binding site that binds CD19.

In some embodiments the antibody is an intact antibody comprising a VH domain paired with a VL domain, the VH and VL domains having sequences selected from the group consisting of:
SEQ ID NO. 1 paired with any one of SEQ ID NOs. 7, 8, 9, 10, 11 or 12;
SEQ ID NO. 2 paired with any one of SEQ ID NOs. 7, 8, 9, 10, 11 or 12;
SEQ ID NO. 3 paired with any one of SEQ ID NOs. 7, 8, 9, 10, 11 or 12;
SEQ ID NO. 4 paired with any one of SEQ ID NOs. 7, 8, 9, 10, 11 or 12;
SEQ ID NO. 5 paired with any one of SEQ ID NOs. 7, 8, 9, 10, 11 or 12; and
SEQ ID NO. 6 paired with any one of SEQ ID NOs. 7, 8, 9, 10, 11 or 12. For example SEQ ID NO. 1 paired with SEQ ID NO. 7, SEQ ID NO. 2 paired with SEQ ID NO. 8, SEQ ID NO. 3 paired with SEQ ID NO. 9, SEQ ID NO. 4 paired with SEQ ID NO. 10, SEQ ID NO. 5 paired with SEQ ID NO. 11 or SEQ ID NO. 6 paired with SEQ ID NO. 12.

In some embodiments, the antibody competes with the antibody secreted by hybridoma ATCC accession No. HB-305 for binding to CD19. In one embodiment the antibody binds CD19 with an association constant ($K_a$) no less than 2, 5 or 10-fold less than the antibody secreted by the hybridoma.

In aspect the antibody is an antibody as described herein which has been modified (or further modified) as described below. In some embodiments the antibody is a humanised, deimmunised or resurfaced version of an antibody disclosed herein.

Terminology

The term "antibody" herein is used in the broadest sense and specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind CD19 (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2 ml, A2m2, Km1, Km2 and Km3) of immunoglobulin molecule. The immunoglobulins can be derived from any species, including human, murine, or rabbit origin.

As used herein, "binds CD19" is used to mean the antibody binds CD19 with a higher affinity than a non-specific partner such as Bovine Serum Albumin (BSA, Genbank accession no. CAA76847, version no. CAA76847.1 GI:3336842, record update date: Jan. 7, 2011 02:30 PM). In-some embodiments the antibody binds CD19 with an association constant ($K_a$) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions. The antibodies of the invention can bind CD19 with a high affinity. For example, in some embodiments the antibody can bind CD19 with a $K_D$ equal to or less than about $10^{-6}$ M, such as $1 \times 10^{-6}$, $10^{-7}$, $10^{-8}$, $10^{-9}$, $10^{-10}$, $10^{-11}$, $10^{-12}$, $10^{-13}$ or $10^{-14}$.

In some embodiments, CD19 polypeptide corresponds to Genbank accession no. NP_001171569, version no. NP_001171569.1 GI:296010921, record update date: Sep. 10, 2012 12:43 AM. In one embodiment, the nucleic acid encoding CD19 polypeptide corresponds to Genbank accession no NM_001178098, version no. NM_001178098.1 GI:296010920, record update date: Sep. 10, 2012 12:43 AM.

"Antibody fragments" comprise a portion of a full length antibody, generally the antigen binding or variable region thereof. Examples of antibody fragments include Fab, Fab', $F(ab')_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Modification of Antibodies

The antibodies disclosed herein may be modified. For example, tomake them less immunogenic to a human subject. This may be achieved using any of a number of techniques familiar to the person skilled in the art. Some of these techniques are described in more detail below.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database available on the website of the Walter+Eliza Hall Institute of Medical Research). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;
(c) defining for the non-human antibody to be humanized, a set of heavy and light chain surface exposed amino acid residues using the set of framework positions generated in step (b);
(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;
(e) substituting, in the amino acid sequence of the non-human antibody to be humanized, the set of heavy and light chain surface exposed amino acid residues defined in step (c) with the set of heavy and light chain surface exposed amino acid residues identified in step (d);

(f) constructing a three-dimensional model of the variable region of the non-human antibody resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and (h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in Methods 36, 43-60 (2005).

Definitions

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds: norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_5$), azepine ($C_7$);

$O_1$: oxirane ($C_3$), oxetane ($C_4$), oxolane (tetrahydrofuran) ($C_5$), oxole (dihydrofuran) (05), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_5$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole (C5), dihydroisoxazole ($C_5$), morpholine ($C_6$), tetrahydrooxazine ($C_5$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{1-4}$), phenanthrene ($C_{1-4}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_5$);

$N_2O_1$: oxadiazole (furazan) (C5);

$N_3O_1$: oxatriazole ($C_5$);

$N_1S_1$: thiazole (C5), isothiazole ($C_5$);

$N_2$: imidazole (1,3-diazole) (C5), pyrazole (1,2-diazole) ($C_5$), pyridazine (1,2-diazine) ($C_6$), pyrimidine (1,3-diazine) ($C_5$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{1-4}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a C5.20 aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group.

Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group.

Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

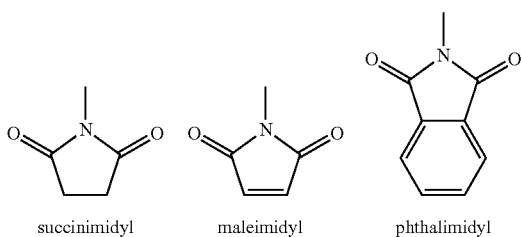

succinimidyl  maleimidyl  phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R')CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

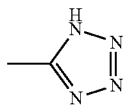

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group.

Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group.

Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR; wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Carbamate nitrogen protecting group: the term "carbamate nitrogen protecting group" pertains to a moiety which masks the nitrogen in the imine bond, and these are well known in the art. These groups have the following structure:

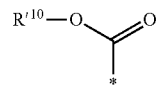

wherein R'$^{10}$ is R as defined above. A large number of suitable groups are described on pages 503 to 549 of Greene, T. W. and Wuts, G. M., Protective Groups in Organic Synthesis, 3' Edition, John Wiley & Sons, Inc., 1999, which is incorporated herein by reference.

Hemi-aminal nitrogen protecting group: the term "hemi-aminal nitrogen protecting group" pertains to a group having the following structure:

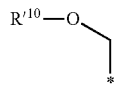

wherein $R'^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

The groups Carbamate nitrogen protecting group and Hemi-aminal nitrogen protecting group may be jointly termed a "nitrogen protecting group for synthesis".

Conjugates

The present invention provides a conjugate comprising a PBD compound connected to the antibody via a Linker Unit.

Figure 5:
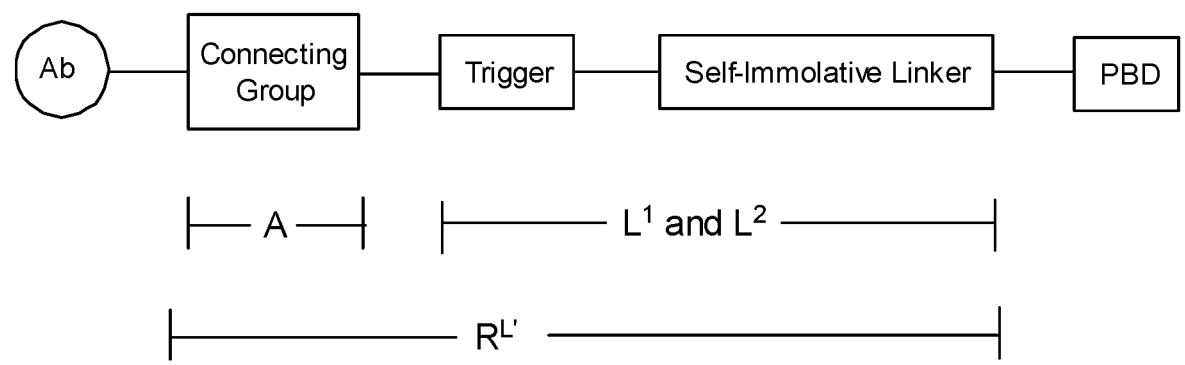
FIG. 5 is a schematic diagram of a conjugate comprising an antibody connected to a spacer connecting group, the spacer connected to a trigger, the trigger connected to a self-immolative linker, and the self-immolative linker connected to the N10 position of a PBD compound.

In one embodiment, the conjugate comprises the antibody connected to a spacer connecting group, the spacer connected to a trigger, the trigger connected to a self-immolative linker, and the self-immolative linker connected to the N10 position of the PBD compound. Such a conjugate is illustrated in FIG. 5 where Ab is the antibody as defined above and PBD is a pyrrolobenzodiazepine compound (D), as described herein. FIG. 5 shows the portions that correspond to $R^{L'}$, A, $L^1$ and $L^2$ in certain embodiments of the invention. $R^{L'}$ may be either $R^{L1'}$ or $R^{L2'}$. D is $D^L$ with $R^{L1'}$ or $R^{L2'}$ removed.

The present invention is suitable for use in providing a PBD compound to a preferred site in a subject. In the preferred embodiments, the conjugate allows the release of an active PBD compound that does not retain any part of the linker. There is no stub present that could affect the reactivity of the PBD compound.

The linker attaches the antibody to the PBD drug moiety D through covalent bond(s). The linker is a bifunctional or multifunctional moiety which can be used to link one or more drug moiety (D) and an antibody unit (Ab) to form antibody-drug conjugates (ADC). The linker ($R^{L'}$) may be stable outside of a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, PBD drug moiety (D) or drug-linker reagent ($D^L$, D-$R^L$), where $R^L$ can be $R^{L1}$ or $R^{L2}$.

The linkers of the ADC preferably prevent aggregation of ADC molecules and keep the ADC freely soluble in aqueous media and in a monomeric state.

The linkers of the ADC are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermansori, G. T. (1996) Bioconjugate Techniques; Academic Press: New York, p 234-242).

In another embodiment, the linker may be substituted with groups which modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with $D^L$, or $D^L$-L with Ab, depending on the synthetic route employed to prepare the ADC.

In one embodiment, L-$R^{L'}$ is a group:

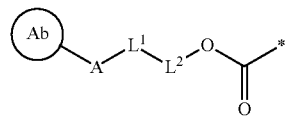

where the asterisk indicates the point of attachment to the Drug Unit (D), Ab is the antibody (L), $L^1$ is a linker, A is a connecting group connecting $L^1$ to the antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of L-$R^{L'}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker.

In one embodiment, $L^2$ is a substrate for enzymatic activity, thereby allowing release of L-$R^{L'}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:
—C(=O)NH—,
—C(=O)O—, —NHC(=O)—,
—OC(=O)—,
—OC(=O)O—,
—NHC(=O)O—,
—OC(=O)NH—, and
—NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

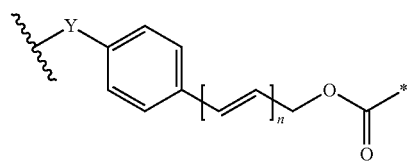

where the asterisk indicates the point of attachment to the N10 position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, NO$_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

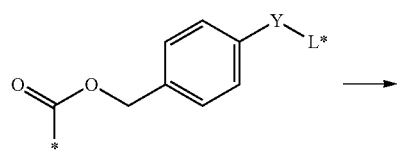

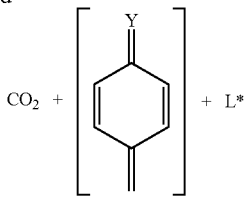

where L* is the activated form of the remaining portion of the linker. These groups have the advantage of separating the site of activation from the compound being protected.

As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

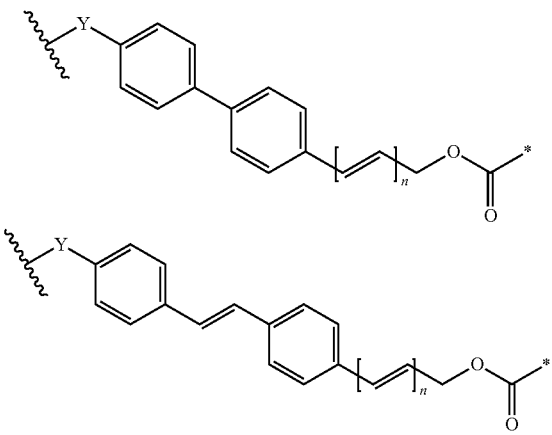

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

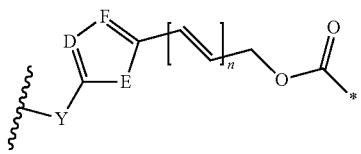

where the asterisk, the wavy line, Y, and n are as defined above, E is O, S or NR, D is N, CH, or CR, and F is N, CH, or CR.

In one embodiment, D is N.
In one embodiment, D is OH.
In one embodiment, E is O or S.

In one embodiment, F is CH.

In a preferred embodiment, the linker is a cathepsin labile linker.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
Phe-Lys-,
Val-Ala-,
Val-Lys-,
Ala-Lys-,
Val-Cit-,
Phe-Cit-,
Leu-Cit-,
-Ile-Cit-,
Phe-Arg-,
Trp-Cit-
where Cit is citrulline.

Preferably, the group —$X_1$—$X_2$— in dipeptide, —NH—$X_1$—$X_2$—CO—, is selected from:
Phe-Lys-,
Val-Ala-,
Val-Lys-,
Ala-Lys-,
Val-Cit-.

Most preferably, the group —$X_1$—$X_2$— in dipeptide, —NH—$X_1$—$X_2$—CO—, is -Phe-Lys- or -Val-Ala-.

Other dipeptide combinations may be used, including those described by Dubowchik et al., *Bioconjugate Chemistry*, 2002, 13,855-869, which is incorporated herein by reference.

In one embodiment, the amino acid side chain is derivatised, where appropriate. For example, an amino group or carboxy group of an amino acid side chain may be derivatised.

In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z-Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, lie, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO-PABC-. The PABC group is connected directly to the N10 position.

Preferably, the self-immolative linker and the dipeptide together form the group —NH-Phe-Lys-CO—NH-PABC-, which is illustrated below:

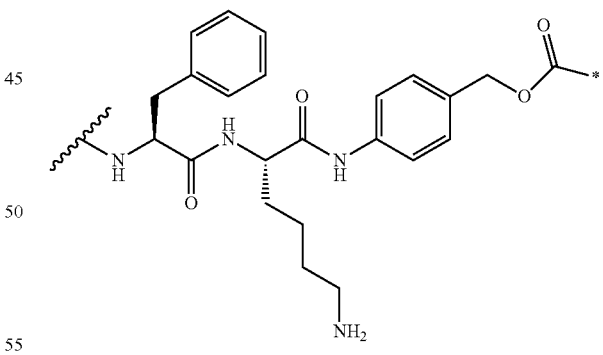

where the asterisk indicates the point of attachment to the N10 position; and the wavy line indicates the point of attachment to the remaining portion of the linker $L^1$ or the point of attachment to A. Preferably, the wavy line indicates the point of attachment to A.

The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

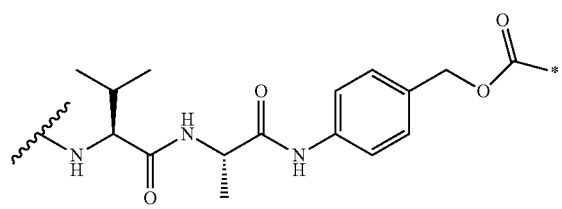 [SMILES: *N[C@H](C(=O)N[C@@H](C)C(=O)Nc1ccc(COC(*)=O)cc1)C(C)C]

where the asterisk and the wavy line are as defined above.

Alternatively, the self-immolative linker and the dipeptide together form the group —NH-Val-Cit-CO—NH-PABC-, which is illustrated below:

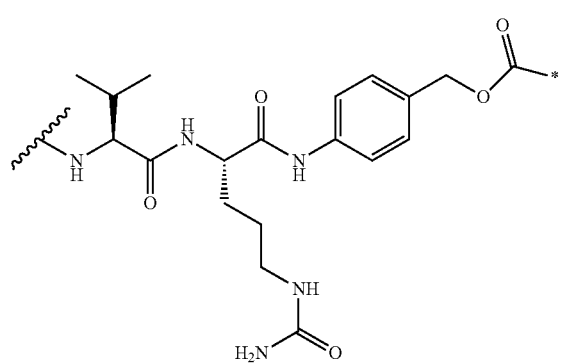 [SMILES: *N[C@H](C(=O)N[C@@H](CCCNC(N)=O)C(=O)Nc1ccc(COC(*)=O)cc1)C(C)C]

where the asterisk and the wavy line are as defined above.

In one embodiment, A is a covalent bond. Thus, $L^1$ and the antibody are directly connected.

For example, where $L^1$ comprises a contiguous amino acid sequence, the N-terminus of the sequence may connect directly to the antibody.

Thus, where A is a covalent bond, the connection between the antibody and $L^1$ may be selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—C(=O)NHC(=O)—,
—S—,
—S—S—,
—CH$_2$C(=O)—, and
=N—NH—.

An amino group of $L^1$ that connects to the antibody may be the N-terminus of an amino acid or may be derived from an amino group of an amino acid side chain, for example a lysine amino acid side chain.

An carboxyl group of $L^1$ that connects to the antibody may be the C-terminus of an amino acid or may be derived from a carboxyl group of an amino acid side chain, for example a glutamic acid amino acid side chain.

A hydroxyl group of $L^1$ that connects to the antibody may be derived from a hydroxyl group of an amino acid side chain, for example a serine amino acid side chain.

A thiol group of $L^1$ that connects to the antibody may be derived from a thiol group of an amino acid side chain, for example a serine amino acid side chain.

The comments above in relation to the amino, carboxyl, hydroxyl and thiol groups of $L^1$ also apply to the antibody.

In one embodiment, $L^2$ together with —OC(=O)— represents:

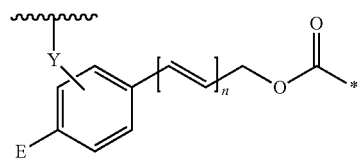

where the asterisk indicates the point of attachment to the N10 position, the wavy line indicates the point of attachment to $L^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, $NO_2$, R or OR. Preferably n is 0 or 1, most preferably 0.

E is selected such that the group is susceptible to activation, e.g. by light or by the action of an enzyme. E may be —$NO_2$ or glucuronic acid. The former may be susceptible to the action of a nitroreductase, the latter to the action of a β-glucuronidase.

In this embodiment, the self-immolative linker will allow for release of the protected compound when E is activated, proceeding along the lines shown below (for n=0):

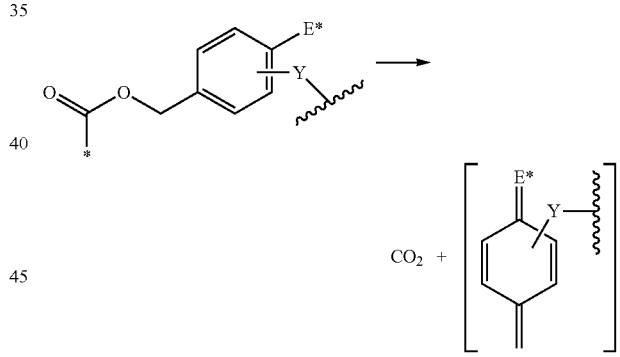

where the asterisk indicates the point of attachment to the N10 position, E' is the activated form of E, and Y is as described above. These groups have the advantage of separating the site of activation from the compound being protected. As described above, the phenylene group may be optionally further substituted.

The group Y may be a covalent bond to $L^1$.

The group Y may be a functional group selected from:
—C(=O)—
—NH—
O—
C(=O)NH—,
—C(=O)O—,
—NHC(=O)—,
—OC(=O)—,
—OC(=O)O—,
—NHC(=O)O—,
—OC(=O)NH—, —NHC(=O)NH—,
—NHC(=O)NH,
—C(=O)NHC(=O)—, and
S—.

Where $L^1$ is a dipeptide, it is preferred that Y is —NH— or —C(=O)—, thereby to form an amide bond between $L^1$ and Y. In this embodiment, the dipeptide sequence need not be a substrate for an enzymatic activity.

In another embodiment, A is a spacer group. Thus, $L^1$ and the antibody are indirectly connected.

$L^1$ and A may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

In one embodiment, the group A is:

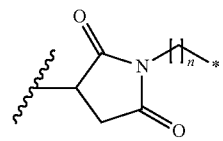

where the asterisk indicates the point of attachment to $L^1$, the wavy line indicates the point of attachment to the antibody, and n is 0 to 6. In one embodiment, n is 5.

In one embodiment, the group A is:

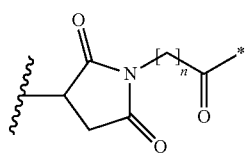

where the asterisk indicates the point of attachment to $L^1$, the wavy line indicates the point of attachment to the antibody, and n is 0 to 6. In one embodiment, n is 5.

In one embodiment, the group A is:

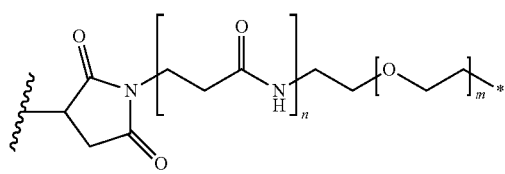

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

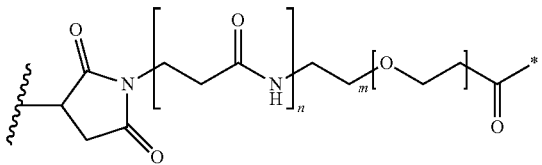

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the connection between the antibody and A is through a thiol residue of the antibody and a maleimide group of A.

In one embodiment, the connection between the antibody and A is:

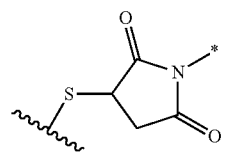 [SMILES: *SC1CC(=O)N(*)C1=O]

where the asterisk indicates the point of attachment to the remaining portion of A and the wavy line indicates the point of attachment to the remaining portion of the antibody. In this embodiment, the S atom is typically derived from the antibody.

In each of the embodiments above, an alternative functionality may be used in place of the maleimide-derived group shown below:

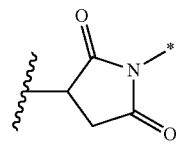 [SMILES: *C1CC(=O)N(*)C1=O]

where the wavy line indicates the point of attachment to the antibody as before, and the asterisk indicates the bond to the remaining portion of the A group.

In one embodiment, the maleimide-derived group is replaced with the group:

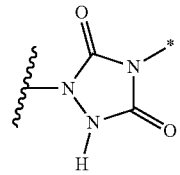 [SMILES: *n1[nH]c(=O)n(*)c1=O]

where the wavy line indicates point of attachment to the antibody, and the asterisk indicates the bond to the remaining portion of the A group.

In one embodiment, the maleimide-derived group is replaced with a group, which optionally together with the antibody, is selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH$_2$C(=O)—
C(=O)CH$_2$—,
=N—NH—, and
—NH—N=.

In one embodiment, the maleimide-derived group is replaced with a group, which optionally together with the antibody, is selected from:

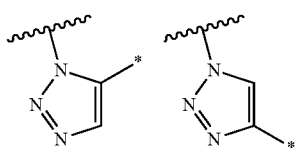 [SMILES: *c1cnnn1* ; *c1cn(*)nn1]

where the wavy line indicates either the point of attachment to the antibody or the bond to the remaining portion of the A group, and the asterisk indicates the other of the point of attachment to the antibody or the bond to the remaining portion of the A group.

Other groups suitable for connecting $L^1$ to the antibody are described in WO 2005/082023.

In one embodiment, the Connecting Group A is present, the Trigger $L^1$ is present and Self-Immolative Linker $L^2$ is absent. Thus, $L^1$ and the Drug unit are directly connected via a bond.

Equivalently in this embodiment, $L^2$ is a bond. This may be particularly relevant when $D^L$ is of Formula II.

$L^1$ and D may be connected by a bond selected from:
—C(=O)N<,
C(=O)O—,
—NHC(=O)—,
—OC(=O)—,
—OC(=O)O—,
—NHC(=O)O—,
—OC(=O)N<, and
—NHC(=O)N<,
where N< or O— are part of D.

In one embodiment, $L^1$ and D are preferably connected by a bond selected from:
—C(=O)N<, and
—NHC(=O)—.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —X$_1$—X$_2$— in dipeptide, —NH—X$_1$—X$_2$—CO—, is selected from:
Phe-Lys-,
Val-Ala-,
Val-Lys-,
Ala-Lys-,
Val-Cit-,
Phe-Cit-,
Leu-Cit-,
—Ile-Cit-,
Phe-Arg-, and
Trp-Cit-;

where Cit is citrulline. In such a dipeptide, —NH— is the amino group of X$_1$, and CO is the carbonyl group of X$_2$.

Preferably, the group —X$_1$—X$_2$— in dipeptide, —NH—X$_1$—X$_2$—CO—, is selected from:
Phe-Lys-,
Val-Ala-,
Val-Lys-,
Ala-Lys-, and
Val-Cit-.

Most preferably, the group —X$_1$—X$_2$— in dipeptide, —NH—X$_1$—X$_2$—CO—, is -Phe-Lys- or -Val-Ala-.

Other dipeptide combinations of interest include:
Gly-Gly-,
Pro-Pro-, and
Val-Glu-.

Other dipeptide combinations may be used, including those described above.

In one embodiment, $L^1$-D is:

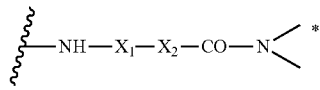

where —NH—X$_1$—X$_2$—CO is the dipeptide, —N< is part of the Drug unit, the asterisk indicates the points of attachment to the remainder of the Drug unit, and the wavy line indicates the point of attachment to the remaining portion of $L^1$ or the point of attachment to A. Preferably, the wavy line indicates the point of attachment to A.

In one embodiment, the dipeptide is valine-alanine and $L^1$-D is:

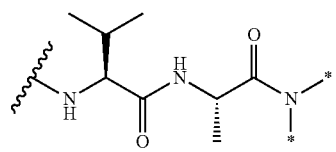 [SMILES: *N[C@H](C(=O)N[C@@H](C)C(=O)N(*)*)C(C)C]

where the asterisks, —N< and the wavy line are as defined above.

In one embodiment, the dipeptide is phenylalanine-lysine and $L^1$-D is:

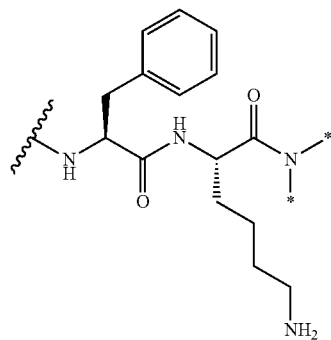 [SMILES: *N[C@@H](Cc1ccccc1)C(=O)N[C@@H](CCCCN)C(=O)N(*)*]

where the asterisks, —N< and the wavy line are as defined above.

In one embodiment, the dipeptide is valine-citrulline.

In one embodiment, the groups A-$L^1$ are:

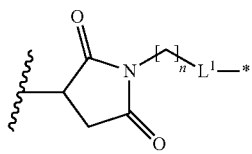

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

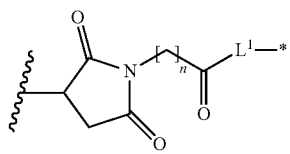

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

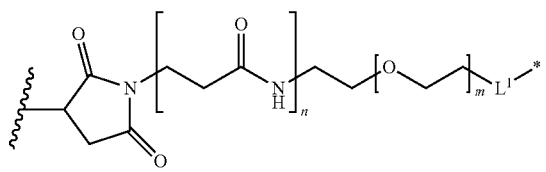

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-$L^1$ are:

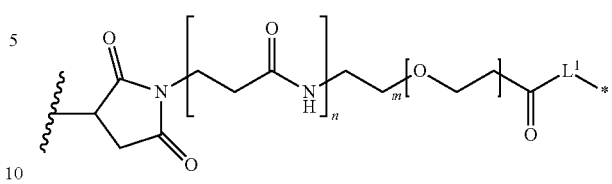

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups A-$L^1$ are:

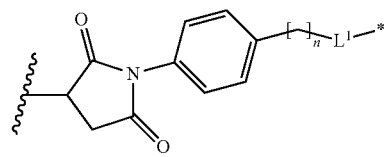

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

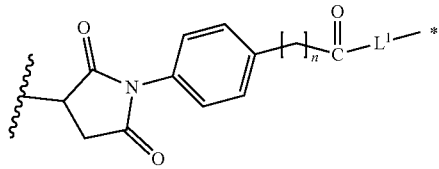

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

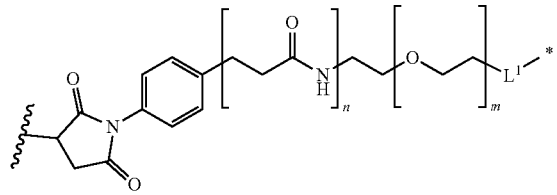

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L$^1$ is:

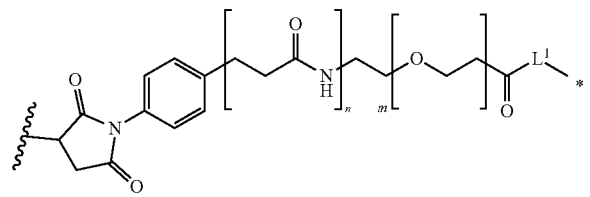

where the asterisk indicates the point of attachment to L$^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L$^1$ are:

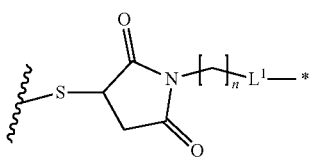

where the asterisk indicates the point of attachment to L$^2$ or D, S is a sulfur group of the Ligand unit, the wavy line indicates the point of attachment to the rest of the Ligand unit, and n is 0 to 6. In one embodiment, n is 5.

In one embodiment, the group A-L$^1$ are:

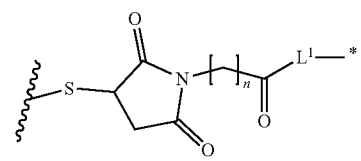

where the asterisk indicates the point of attachment to L$^2$ or D, S is a sulfur group of the Ligand unit, the wavy line indicates the point of attachment to the remainder of the Ligand unit, and n is 0 to 6. In one embodiment, n is 5.

In one embodiment, the groups A$^1$-L$^1$ are:

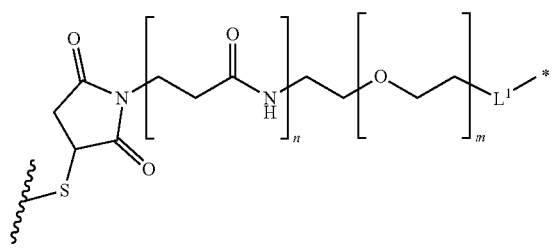

where the asterisk indicates the point of attachment to L$^2$ or D, S is a sulfur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A$^1$-L$^1$ are:

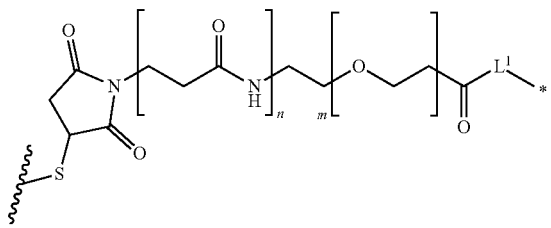

where the asterisk indicates the point of attachment to L$^2$ or D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8.

In one embodiment, the groups A$^1$-L$^1$ are:

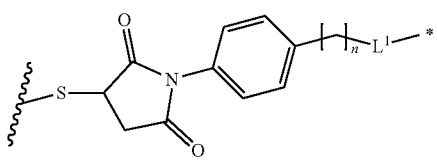

where the asterisk indicates the point of attachment to L$^2$ or D, the wavy line indicates the point of attachment to the remainder of the Ligand unit, and n is 0 to 6. In one embodiment, n is 5.

In one embodiment, the groups A$^1$-L$^1$ are:

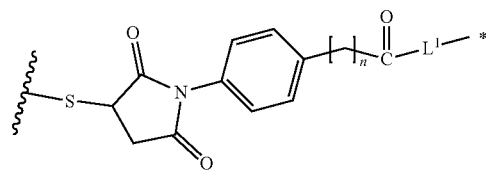

where the asterisk indicates the point of attachment to L$^2$ or D, the wavy line indicates the point of attachment to the remainder of the Ligand unit, and n is 0 to 6. In one embodiment, n is 5.

In one embodiment, the groups A$^1$-L$^1$ are:

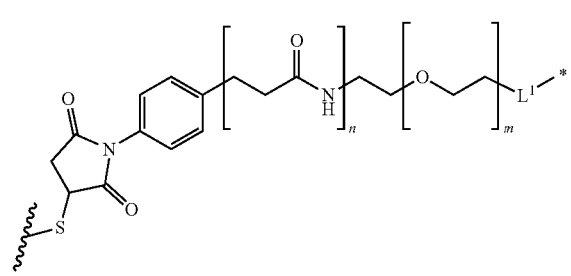

where the asterisk indicates the point of attachment to L$^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

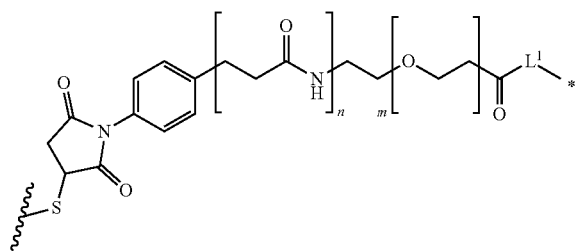

where the asterisk indicates the point of attachment to $L^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

The group $R^{L'}$ is derivable from the group $R^L$. The group $R^L$ may be converted to a group $R^{L'}$ by connection of an antibody to a functional group of $R^L$. Other steps may be taken to convert $R^L$ to $R^{L'}$. These steps may include the removal of protecting groups, where present, or the installation of an appropriate functional group.

$R^L$

Linkers can include protease-cleavable peptidic moieties comprising one or more amino acid units. Peptide linker reagents may be prepared by solid phase or liquid phase synthesis methods (E. Schröder and K. Lübke, *The Peptides*, volume 1, pp 76-136 (1965) Academic Press) that are well known in the field of peptide chemistry, including t-BOC chemistry (Geiser et al "Automation of solid-phase peptide synthesis" in *Macromolecular Sequencing and Synthesis*, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

Exemplary amino acid linkers include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Amino acid side chains include those occurring naturally, as well as minor amino acids and non-naturally occurring amino acid analogs, such as citrulline. Amino acid side chains include hydrogen, methyl, isopropyl, isobutyl, sec-butyl, benzyl, p-hydroxybenzyl, —$CH_2OH$, —$CH(OH)$ $CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC$ (=NH)$NH_2$, —$(CH_2)_3NH_2$, —$(CH_2)_3NHCOCH_3$, —$(CH_2)_3NHCHO$, —$(CH_2)_4NHC$(=NH)$NH_2$, —$(CH_2)_4$ $NH_2$, —$(CH_2)_4NHCOCH_3$, —$(CH_2)_4NHCHO$, —$(CH_2)_3$ $NHCONH_2$, —$(CH_2)_4NHCONH_2$, —$CH_2CH_2CH(OH)$ $CH_2NH_2$, 2-pyridylmethyl-, 3-pyridylmethyl-, 4-pyridylmethyl-, phenyl, cyclohexyl, as well as the following structures:

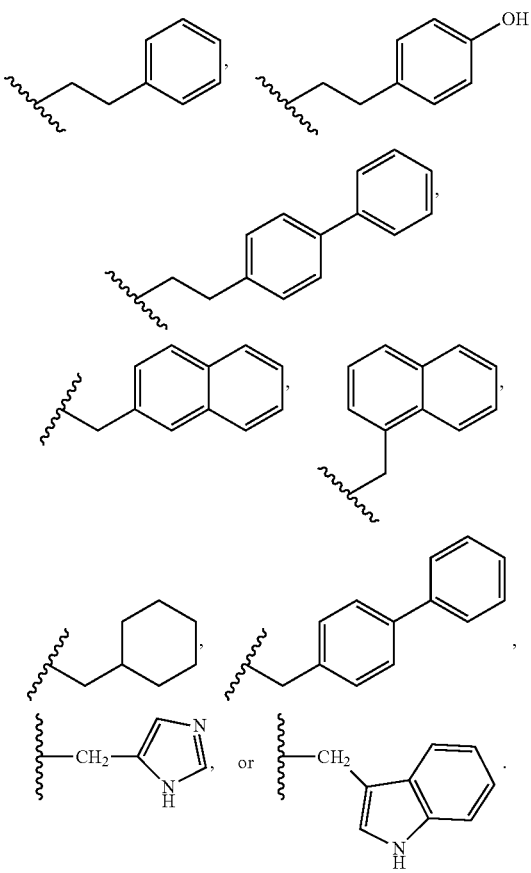

When the amino acid side chains include other than hydrogen (glycine), the carbon atom to which the amino acid side chain is attached is chiral. Each carbon atom to which the amino acid side chain is attached is independently in the (S) or (R) configuration, or a racemic mixture. Drug-linker reagents may thus be enantiomerically pure, racemic, or diastereomeric.

In exemplary embodiments, amino acid side chains are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit).

An exemplary valine-citrulline (val-cit or vc) dipeptide linker reagent useful for constructing a linker-PBD drug moiety intermediate for conjugation to an antibody, having a para-aminobenzylcarbamoyl (PAB) self-immolative spacer has the structure:

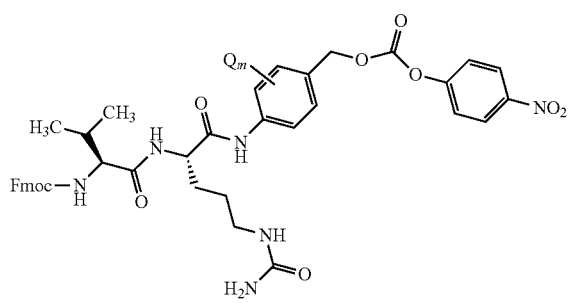

where Q is $C_1$-$C_8$ alkyl, —O—($C_1$-$C_8$ alkyl), -halogen, —$NO_2$ or —CN; and m is an integer ranging from 0-4.

An exemplary phe-lys(Mtr) dipeptide linker reagent having a p-aminobenzyl group can be prepared according to Dubowchik, et al. (1997) Tetrahedron Letters, 38:5257-60, and has the structure:

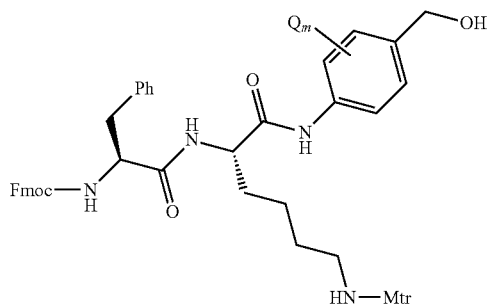

where Mtr is mono-4-methoxytrityl, Q is $C_1$—C alkyl, —O—($C_1$-$C_8$ alkyl), -halogen, —$NO_2$ or —CN; and m is an integer ranging from 0-4.

The "self-immolative linker" PAB (para-aminobenzyloxycarbonyl), attaches the drug moiety to the antibody in the antibody drug conjugate (Carl et al (1981) J. Med. Chem. 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other examples of self-immolative spacers besides PAB include, but are not limited to: (i) aromatic compounds that are electronically similar to the PAB group such as 2-aminoimidazol-5-methanol derivatives (Hay et al. (1999) Bioorg. Med. Chem. Lett. 9:2237), thiazoles (U.S. Pat. No. 7,375,078), multiple, elongated PAB units (de Groot et al (2001) J. Org. Chem. 66:8815-8830); and ortho or para-aminobenzylacetals; and (ii) homologated styryl PAB analogs (U.S. Pat. No. 7,223, 837). Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo [2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacers useful in ADC.

In one embodiment, a valine-citrulline dipeptide PAB analog reagent has a 2,6 dimethyl phenyl group and has the structure:

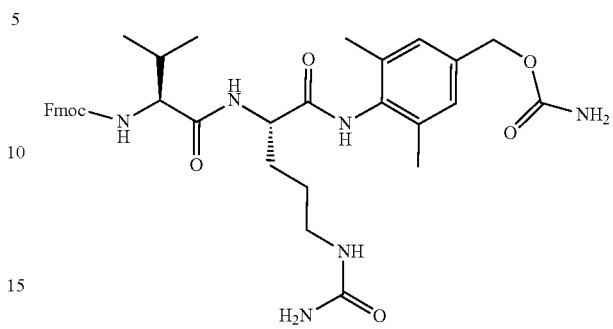

Linker reagents useful for the antibody drug conjugates of the invention include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succininiidyl-(4-vinylsulfone)benzoate), and bis-maleimide reagents: DTME, BMB, BMDB, BMH, BMOE, 1,8-bis-maleimidodiethyl-eneglycol (BM(PEO)$_2$), and 1,11-bis-maleimidotriethyl-eneglycol (BM(PEO)$_3$), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, PBD drug moiety, or linker intermediate include iodoacetamide, bromoacetamide, vinyl pyridine, disulfide, pyridyl disulfide, isocyanate, and isothiocyanate.

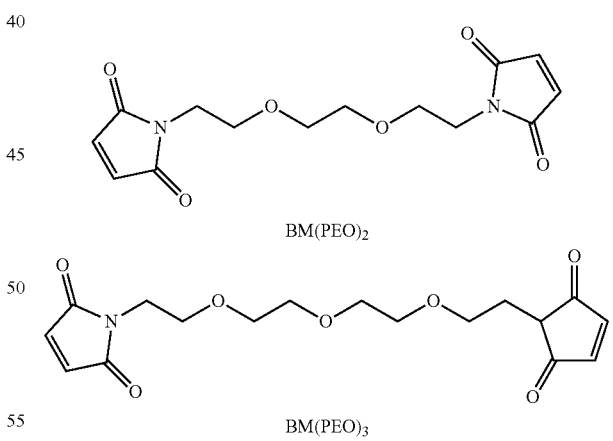

Other embodiments of linker reagents are: N-succinimidyl-4-(2-pyridylthio)pentanoate (SPP), N-succinimidyl-3-(2-pyridyldithio) propionate (SPDP, Carlsson et al (1978) Biochem. J. 173:723-737), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic or branched linker.

One exemplary embodiment of a dendritic type linker has the structure:

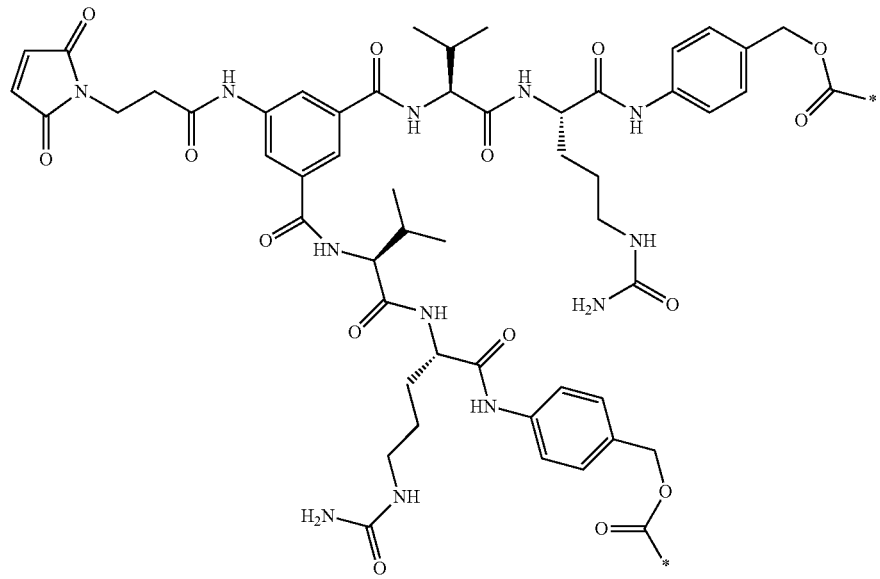 [SMILES: *C(=O)OCc1ccc(NC(=O)[C@H](CCCNC(N)=O)NC(=O)[C@@H](NC(=O)c2cc(NC(=O)CCN3C(=O)C=CC3=O)cc(C(=O)N[C@H](C(=O)N[C@@H](CCCNC(N)=O)C(=O)Nc3ccc(COC(*)=O)cc3)C(C)C)c2)C(C)C)cc1]

where the asterisk indicate the point of attachment to the N10 position of a PBD moiety.

$R^c$, Capping Group

The conjugate of the first aspect of the invention may have a capping group $R^C$ at the N10 position. Compound E may have a capping group $R^C$.

In one embodiment, where the conjugate is a dimer with each monomer being of formula (A), the group $R^{10}$ in one of the monomer units is a capping group $R^C$ or is a group $R^{10}$.

In one embodiment, where the conjugate is a dimer with each monomer being of formula (A), the group $R^{10}$ in one of the monomer units is a capping group $R^C$.

In one embodiment, where compound E is a dimer with each monomer being of formula (E), the group $R^L$ in one of the monomer units is a capping group $R^C$ or is a linker for connection to an antibody.

In one embodiment, where compound E is a dimer with each monomer being of formula (E), the group $R^L$ in one of the monomer units is a capping group $R^C$.

The group $R^C$ is removable from the N10 position of the PBD moiety to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine.

In one embodiment, $R^C$, may be a protecting group that is removable to leave an N10-C11 imine bond, a carbinolamine, a substituted cabinolamine, or, where $QR^{11}$ is $OSO_3M$, a bisulfite adduct. In one embodiment, $R^C$ is a protecting group that is removable to leave an N10-C11 imine bond.

The group $R^c$ is intended to be removable under the same conditions as those required for the removal of the group $R^{10}$, for example to yield an N10-C11 imine bond, a carbinolamine and so on. The capping group acts as a protecting group for the intended functionality at the N10 position. The capping group is intended not to be reactive towards an antibody. For example, $R^C$ is not the same as $R^L$.

Compounds having a capping group may be used as intermediates in the synthesis of dimers having an imine monomer. Alternatively, compounds having a capping group may be used as conjugates, where the capping group is removed at the target location to yield an imine, a carbinolamine, a substituted cabinolamine and so on. Thus, in this embodiment, the capping group may be referred to as a therapeutically removable nitrogen protecting group, as defined in the inventors' earlier application WO 00/12507.

In one embodiment, the group $R^C$ is removable under the conditions that cleave the linker $R^L$ of the group $R^{10}$. Thus, in one embodiment, the capping group is cleavable by the action of an enzyme.

In an alternative embodiment, the capping group is removable prior to the connection of the linker $R^L$ to the antibody. In this embodiment, the capping group is removable under conditions that do not cleave the linker $R^L$.

Where a compound includes a functional group $G^1$ to form a connection to the antibody, the capping group is removable prior to the addition or unmasking of $G^1$.

The capping group may be used as part of a protecting group strategy to ensure that only one of the monomer units in a dimer is connected to an antibody.

The capping group may be used as a mask for a N10-C11 imine bond. The capping group may be removed at such time as the imine functionality is required in the compound. The capping group is also a mask for a carbinolamine, a substituted cabinolamine, and a bisulfite adduct, as described above.

$R^C$ may be an N10 protecting group, such as those groups described in the inventors' earlier application, WO 00/12507. In one embodiment, $R^C$ is a therapeutically removable nitrogen protecting group, as defined in the inventors' earlier application, WO 00/12507.

In one embodiment, $R^C$ is a carbamate protecting group.

In one embodiment, the carbamate protecting group is selected from:

Alloc, Fmoc, Boc, Troc, Teoc, Psec, Cbz and PNZ.

Optionally, the carbamate protecting group is further selected from Moc.

In one embodiment, $R^C$ is a linker group $R^L$ lacking the functional group for connection to the antibody.

This application is particularly concerned with those $R^C$ groups which are carbamates.

In one embodiment, $R^C$ is a group:

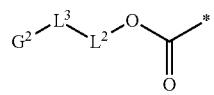

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{10}$.
$L^2$ is as defined above in relation to $R^{10}$.

Various terminating groups are described below, including those based on well known protecting groups.

In one embodiment, $L^3$ is a cleavable linker $L^1$, and $L^2$, together with OC(=O), forms a self-immolative linker. In this embodiment, $G^2$ is Ac (acetyl) or Moc, or a carbamate protecting group selected from:

Alloc, Fmoc, Boc, Troc, Teoc, Psec, Cbz and PNZ.

Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

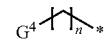

where the asterisk indicates the point of attachment to $L^3$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, and preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

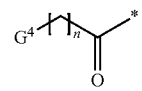

where the asterisk indicates the point of attachment to $L^3$, and n and $G^4$ are as defined above.

In one embodiment, the group $G^2$ is:

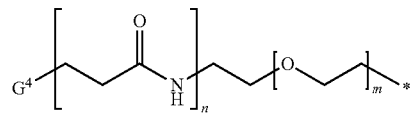

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

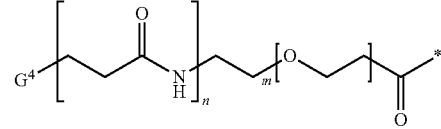

where the asterisk indicates the point of attachment to $L^3$, and n, m and $G^4$ are as defined above.

In one embodiment, the group $G^2$ is:

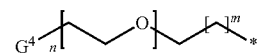

where n is 1-20, m is 0-6, and $G^4$ is selected from OH, OR, SH, SR, COOR, $CONH_2$, CONHR, CONRR', $NH_2$, NHR, NRR', $NO_2$, and halo. In one embodiment, n is 1-10. In another embodiment, n is 10 to 50, preferably 20 to 40. In one embodiment, n is 1. In one embodiment, m is 1. The groups OH, SH, NH$_2$ and NHR are protected. In one embodiment, G$^4$ is OR, SR, COOR, CONH$_2$, CONHR, CONRR', and NRR'. In one embodiment, G$^4$ is OR, SR, and NRR'. Preferably G$^4$ is selected from OR and NRR', most preferably G$^4$ is OR. Preferably G$^4$ is OMe.

In one embodiment, the group G$^2$ is:

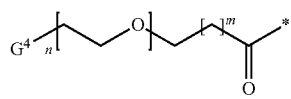

where the asterisk indicates the point of attachment to L$^3$, and n, m and G$^4$ are as defined above.

In each of the embodiments above G$^4$ may be OH, SH, NH$_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, NH$_2$ or NHR are protected with Boc, Moc, Z-Cl, Fmoc, Z, or Alloc.

In one embodiment, the group G$^2$ is present in combination with a group L$^3$, which group is a dipeptide.

The capping group is not intended for connection to the antibody. Thus, the other monomer present in the dimer serves as the point of connection to the antibody via a linker.

Accordingly, it is preferred that the functionality present in the capping group is not available for reaction with an antibody. Thus, reactive functional groups such as OH, SH, NH$_2$, COOH are preferably avoided. However, such functionality may be present in the capping group if protected, as described above.

Embodiments

Embodiments of the present invention include ConjA wherein the antibody is as defined above.

Embodiments of the present invention include ConjB wherein the antibody is as defined above.

Embodiments of the present invention include ConjC wherein the antibody is as defined above.

Embodiments of the present invention include ConjD wherein the antibody is as defined above.

Embodiments of the present invention include ConjE wherein the antibody is as defined above.

As mentioned above, some embodiments of the invention exclude ConjA, ConjB, ConjC, ConjD and ConjE.

Drug Loading

The drug loading is the average number of PBD drugs per antibody, e.g. antibody. Where the compounds of the invention are bound to cysteines, drug loading may range from 1 to 8 drugs (D$^L$) per antibody, i.e. where 1, 2, 3, 4, 5, 6, 7, and 8 drug moieties are covalently attached to the antibody. Compositions of conjugates include collections of antibodies, conjugated with a range of drugs, from 1 to 8. Where the compounds of the invention are bound to lysines, drug loading may range from 1 to 80 drugs (D$^L$) per antibody, although an upper limit of 40, 20, 10 or 8 may be preferred. Compositions of conjugates include collections of antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114

(13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Alternatively, site-specific conjugation can be achieved by engineering antibodies to contain unnatural amino acids in their heavy and/or light chains as described by Axup et al. ((2012), Proc Natl Acad Sci USA. 109(40):16101-16116). The unnatural amino acids provide the additional advantage that orthogonal chemistry can be designed to attach the linker reagent and drug.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 20. In some embodiments the range is selected from 1 to 8, 2 to 8, 2 to 6, 2 to 4, and 4 to 8.

In some embodiments, there is one dimer pyrrolobenzodiazepine group per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (–N⁺HR¹R²), a salt or solvate of the amino group, for example, a hydrochloride salt, as well as conventional protected forms of an amino group.

Similarly, a reference to a hydroxyl group also includes the anionic form (—O⁻), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.,* 66, 1-19 (1977).

For example, if the compound is anionic, or has a functional group which may be anionic (e.g. —COOH may be —COO—), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e. NH₄) and substituted ammonium ions (e.g. NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^A$OH, where $R^A$ is $C_{1-4}$ alkyl):

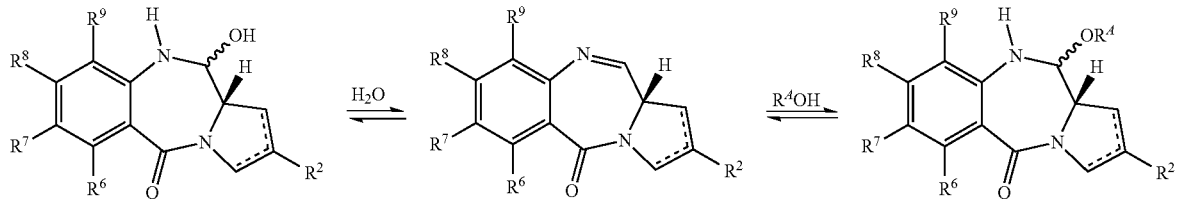

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

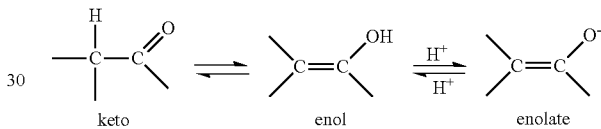

keto   enol   enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity
In Vitro Cell Proliferation Assays

Generally, the cytotoxic or cytostatic activity of an antibody-drug conjugate (ADC) is measured by: exposing mammalian cells having receptor proteins to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 µl per well) into black 96 well plates. Plates of adherent cell lines are incubated overnight to allow adherence. Suspension cell cultures can be used on the day of seeding.

A stock solution (1 ml) of ADC (20 µg/ml) is made in the appropriate cell culture medium. Serial 10-fold dilutions of stock ADC are made in 15 ml centrifuge tubes by serially transferring 100 µl to 900 µl of cell culture medium.

Four replicate wells of each ADC dilution (100 µl) are dispensed in 96-well black plates, previously plated with cell suspension (100 µl), resulting in a final volume of 200 µl. Control wells receive cell culture medium (100 µl).

If the doubling time of the cell line is greater than 30 hours, ADC incubation is for 5 days, otherwise a four day incubation is done.

At the end of the incubation period, cell viability is assessed with the Alamar blue assay. AlamarBlue (Invitrogen) is dispensed over the whole plate (20 µl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

Use

The conjugates of the invention may be used to provide a PBD compound at a target location.

The target location is preferably, a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound RelA, RelB, RelC, RelD or RelE. Thus, the conjugate may be used to selectively provide a compound RelA, RelB, Rel C, RelD or RelE to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to, non-Hodgkin Lymphoma including diffuse large B-cell lymphoma (DLBCL), follicular lymphoma, (FL), Mantle Cell lymphoma (MCL), chronic lymphatic, lymphoma (CLL) nd leukemias such as Hairy cell leukemia (HCL), Hairy cell leukemia variant (HCL-v) and Acute Lymphoblastic Leukaemia (ALL).

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gammall, calicheamicin omegall (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALL-OVECTIN®, LEUVECTIN®, and VAXID®; PROLEU-KIN® rIL-2; topoisomerase 1 inhibitors such as LURTO-TECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, New York, USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug Conjugates

Antibody drug conjugates may be prepared by several routes, employing organic chemistry reactions, conditions, and reagents known to those skilled in the art, including reaction of a nucleophilic group of an antibody with a drug-linker reagent. This method may be employed to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

Further Preferences

The following preferences may apply to all aspects of the invention as described above, or may relate to a single aspect. The preferences may be combined together in any combination.

In some embodiments, $R^{6'}$, $R^{7'}$, $R^{9'}$, and Y' are preferably the same as $R^6$, $R^7$, $R^9$, and Y respectively.

Dimer Link

Y and Y' are preferably O.

R" is preferably a $C_{3-7}$ alkylene group with no substituents. More preferably R" is a $C_3$, $C_5$ or $C_7$ alkylene. Most preferably, R" is a $C_3$ or $C_5$ alkylene.

$R^6$ to $R^9$ $R^9$ is preferably H.

$R^6$ is preferably selected from H, OH, OR, SH, $NH_2$, nitro and halo, and is more preferably H or halo, and most preferably is H.

$R^7$ is preferably selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. $-NMe_2$); $-(OC_2H_4)_qOMe$, where q is from 0 to 2; nitrogen-containing $C_6$ heterocyclyls, including morpholino, piperidinyl and N-methyl-piperazinyl.

These preferences apply to $R^{9'}$, $R^{6'}$ and $R^{7'}$ respectively.

$R^{12}$

When there is a double bond present between C2' and C3', $R^{12}$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

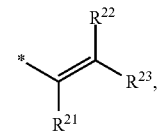

(d)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

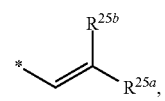

(e)

wherein one of $R^{25a}$ and $R^{25b}$ is H and the other is selected from: phenyl, which phenyl is optionally substituted by a group selected from halo methyl, methoxy; pyridyl; and thiophenyl; and

(f)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

When $R^{12}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^{12}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents, when $R^{12}$ is a $C_{5-10}$ Aryl Group

If a substituent on $R^{12}$ when $R^{12}$ is a $C_{5-10}$ aryl group is halo, it is preferably F or Cl, more preferably Cl.

If a substituent on $R^{12}$ when $R^{12}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g. phenoxy, pyridyloxy, furanyloxy). The alkoxy group may itself be further substituted, for example by an amino group (e.g. dimethylamino).

If a substituent on $R^{12}$ when $R^{12}$ is a $C_{5-10}$ aryl group is $C_{1-7}$ alkyl, it may preferably be a $C_{1-4}$ alkyl group (e.g. methyl, ethyl, propyl, butyl).

If a substituent on $R^{12}$ when $R^{12}$ is a $C_{5-10}$ aryl group is $C_{3-7}$ heterocyclyl, it may in some embodiments be C nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If the $C_6$ nitrogen containing heterocyclyl group is piperazinyl, the said further substituent may be on the second nitrogen ring atom.

If a substituent on $R^{12}$ when $R^{12}$ is a $C_{5-10}$ aryl group is bis-oxy-$C_{1-3}$ alkylene, this is preferably bis-oxy-methylene or bis-oxy-ethylene.

If a substituent on $R^{12}$ when $R^{12}$ is a $C_{5-10}$ aryl group is ester, this is preferably methyl ester or ethyl ester.

Particularly preferred substituents when $R^{12}$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituent for $R^{12}$ are dimethylaminopropyloxy and carboxy.

Particularly preferred substituted $R^{12}$ groups when $R^{12}$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_3$-6 saturated cycloalkyl, it may be cyclopropyl, cyclobutyl, cyclopentyl or cyclohexyl. In some embodiments, it may be cyclopropyl.

When $R^{12}$ is

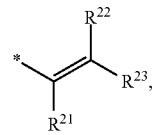

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^2$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{21}$ is H.
In some embodiments, $R^{22}$ is H.
In some embodiments, $R^{23}$ and H.
In some embodiments, $R^{21}$ and $R^{22}$ are H.
In some embodiments, $R^{21}$ and $R^{23}$ are H.
In some embodiments, $R^{22}$ and $R^{23}$ are H.
An $R^{12}$ group of particular interest is:

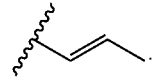 [SMILES: */C=C/C]

When $R^{12}$ is

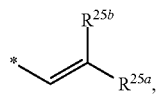

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

$R^{24}$, $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2' and C3', $R^{12}$ is

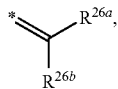

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^2$

The above preferences for $R^{12}$ apply equally to $R^2$.

$R^{22}$

In some embodiments, $R^{22}$ is of formula IIa.

A in $R^{22}$ when it is of formula IIa may be phenyl group or a $C_{5-7}$ heteroaryl group, for example furanyl, thiophenyl and pyridyl. In some embodiments, A is preferably phenyl.

$Q^2$-X may be on any of the available ring atoms of the $C_{5-7}$ aryl group, but is preferably on a ring atom that is not adjacent the bond to the remainder of the compound, i.e. it is preferably β or γ to the bond to the remainder of the compound. Therefore, where the $C_{5-7}$ aryl group (A) is phenyl, the substituent ($Q^2$-X) is preferably in the meta- or para-positions, and more preferably is in the para-position.

In some embodiments, $Q^1$ is a single bond. In these embodiments, $Q^2$ is selected from a single bond and —Z—$(CH_2)_n$—, where Z is selected from a single bond, O, S and NH and is from 1 to 3. In some of these embodiments, $Q^2$ is a single bond. In other embodiments, $Q^2$ is —Z—$(CH_2)_n$—. In these embodiments, Z may be O or S and n may be 1 or n may be 2. In other of these embodiments, Z may be a single bond and n may be 1.

In other embodiments, $Q^1$ is —CH=CH—.

In other embodiments, $R^{22}$ is of formula IIb. In these embodiments, $R^{C1}$, $R^{C2}$ and $R^{C3}$ are independently selected from H and unsubstituted $C_{1-2}$ alkyl. In some preferred embodiments, $R^{C1}$, $R^{C2}$ and $R^{C3}$ are all H. In other embodiments, $R^{C1}$, $R^{C2}$ and $R^{C3}$ are all methyl. In certain embodiments, $R^{C1}$, $R^{C2}$ and $R^{C3}$ are independently selected from H and methyl.

X is a group selected from the list comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

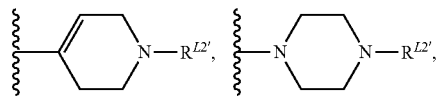

$NR^N R^{L2'}$, wherein $R^N$ is selected from the group comprising H and $C_{1-4}$ alkyl. X may preferably be: OH, SH, $CO_2H$, —N=C=O or $NHR^N$; and may more preferably be: O—$R^{L2'}$, S—$R^{L2'}$, $CO_2$—$R^{L2'}$, —NH—C(=O)—$R^{L2'}$ or NH—$R^{L2'}$. Particularly preferred groups include: O—$R^{L2'}$, S—$R^{2'}$ and NH—$R^{L2'}$, with NH—$R^{L2'}$ being the most preferred group.

In some embodiments $R^{22}$ is of formula IIc. In these embodiments, it is preferred that Q is $NR^N$—$R^{L2'}$. In other embodiments, Q is O—$R^{L2'}$. In further embodiments, Q is S—$R^{L2'}$. $R^N$ is preferably selected from H and methyl. In some embodiment, $R^N$ is H. In other embodiments, $R^N$ is methyl.

In some embodiments, $R^{22}$ may be -A-$CH_2$—X and -A-X. In these embodiments, X may be O—$R^{L2'}$, S—$R^{L2'}$, $CO_2$—$R^{L2'}$, CO—$R^{L2'}$ and NH—$R^{L2'}$. In particularly preferred embodiments, X may be NH—$R^{L2'}$.

$R^{10}$, $R^{11}$

In some embodiments, $R^{10}$ and $R^{11}$ together form a double bond between the nitrogen and carbon atoms to which they are bound.

In some embodiments, $R^{11}$ is OH.

In some embodiments, $R^{11}$ is OMe.

In some embodiments, $R^{11}$ is $SO_zM$, where z is 2 or 3 and M is a monovalent pharmaceutically acceptable cation.

$R^{11a}$

In some embodiments, $R^{11a}$ is OH.

In some embodiments, $R^{11a}$ is OMe.

In some embodiments, $R^{11a}$ is $SO_zM$, where z is 2 or 3 and M is a monovalent pharmaceutically acceptable cation.

$R^{20}$, $R^{21}$

In some embodiments, $R^{20}$ and $R^{21}$ together form a double bond between the nitrogen and carbon atoms to which they are bound.

In some embodiments $R^{20}$ is H.

In some embodiments, $R^{20}$ is $R^C$.

In some embodiments, $R^{21}$ is OH.

In some embodiments, $R^{21}$ is OMe.

In some embodiments, $R^{21}$ is $SO_zM$, where z is 2 or 3 and M is a monovalent pharmaceutically acceptable cation.

$R^{30}$, $R^{31}$

In some embodiments, $R^{30}$ and $R^{31}$ together form a double bond between the nitrogen and carbon atoms to which they are bound.

In some embodiments, $R^{31}$ is OH.

In some embodiments, $R^{31}$ is OMe.

In some embodiments, $R^{31}$ is $SO_zM$, where z is 2 or 3 and M is a monovalent pharmaceutically acceptable cation.

M and z

It is preferred that M is a monovalent pharmaceutically acceptable cation, and is more preferably $Na^+$.

z is preferably 3.

Preferred conjugates of the first aspect of the present invention may have a $D^L$ of formula Ia:

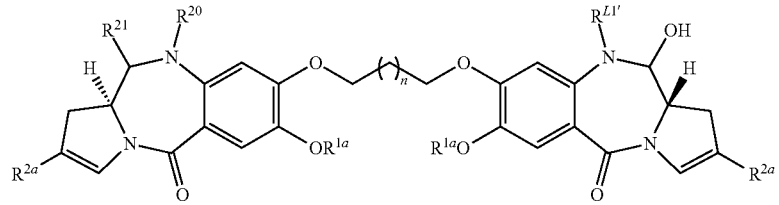

Ia where
$R^{L1'}$, $R^{20}$ and $R^{21}$ are as defined above;
n is 1 or 3;
$R^{1a}$ is methyl or phenyl; and
$R^{2a}$ is selected from:

(a)
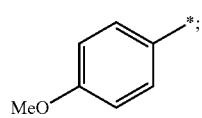

Preferred conjugates of the first aspect of the present invention may have a $D^L$ of formula Ib:

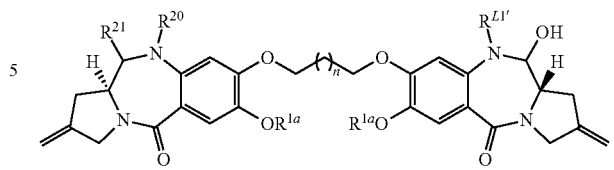

where
$R^{L1'}$, $R^{20}$ and $R^{21}$ are as defined above;
n is 1 or 3; and
$R^{1a}$ is methyl or phenyl.

Preferred conjugates of the first aspect of the present invention may have a $D^L$ of formula Ic:

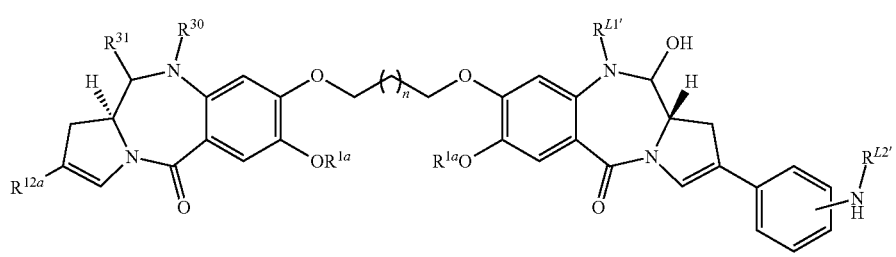

where $R^{L2'}$, $R^{10}$, $R^{11}$, $R^{30}$ and $R^{31}$ are as defined above
n is 1 or 3;
$R^{12a}$ is selected from:

(a)
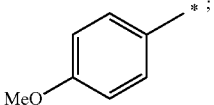

(b)

(c)
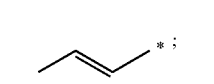

(d)
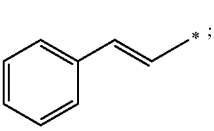

(e)

(f)

(g)
and

-continued (b)

(c)
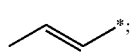

(d)
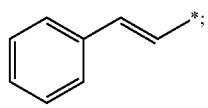

(e)

(f)

(g)
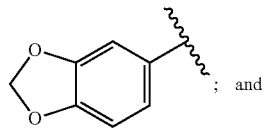
; and (h)
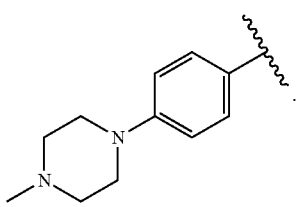
.

Preferred conjugates of the first aspect of the present invention may have a $D^L$ of formula Ib:

-continued (h)

[structure: 4-(4-methylpiperazin-1-yl)phenyl group]

the amino group is at either the meta or para positions of the phenyl group.

Preferred conjugates of the first aspect of the present invention may have a $D^L$ of formula Id:

Id

[structure of formula Id with substituents $R^{31}$, $R^{30}$, $R^{10}$, $R^{11}$, $OR^{1a}$, $R^{1a}O$, $R^{12a}$, $R^{L2'}$]

where $R^{L2'}$, $R^{10}$, $R^{11}$, $R^{30}$ and $R^{31}$ are as defined above
n is 1 or 3;
$R^{1a}$ is methyl or phenyl;
$R^{12a}$ is selected from:

(a)

[4-methoxyphenyl structure with *]

MeO

-continued (b)

[structure]

(c)

[structure]

(d)

[styryl structure with phenyl]

(e)

[cyclopropyl structure with *]

-continued (f)

[ethynyl structure]

(g)

[1,3-benzodioxol-5-yl structure]; and

-continued (h)

[4-(4-methylpiperazin-1-yl)phenyl structure]

Preferred conjugates of the first aspect of the present invention may have a $D^L$ of formula Ie:

Ie

[structure of formula Ie with substituents $R^{31}$, $R^{30}$, $R^{10}$, $R^{11}$, $OR^{1a}$, $R^{1a}O$, $R^{12a}$, $R^{L2'}$]

where $R^{L2'}$, $R^{10}$, $R^{11}$, $R^{30}$ and $R^{31}$ are as defined above
n is 1 or 3;
$R^{1a}$ is methyl or phenyl;
$R^{12a}$ is selected from:

(a)

[4-methoxyphenyl structure with *]

MeO (b)

[structure]

(c)

[structure]

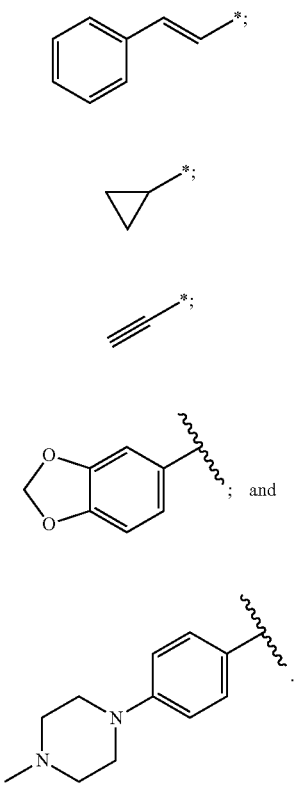

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS Conditions:

Method 1 (Default Method, Used Unless Stated Otherwise)

The HPLC (Waters Alliance 2695) was run using a mobile phase of water (A) (formic acid 0.1%) and acetonitrile (B) (formic acid 0.1%). Gradient: initial composition 5% B held over 1.0 min, then increase from 5% B to 95% B over a 3 min period. The composition was held for 0.1 min at 95% B, then returned to 5% B in 0.03 minutes and hold there for 0.87 min. Total gradient run time equals 5 minutes.

Method 2

The HPLC (Waters Alliance 2695) was run using a mobile phase of water (A) (formic acid 0.1%) and acetonitrile (B) (formic acid 0.1%). Gradient: initial composition 5% B held over 1.0 minute, then increase from 5% B to 95% B over a 2.5 minute period. The composition was held for 0.5 minutes at 95% B, then returned to 5% B in 0.1 minutes and hold there for 0.9 min. Total gradient run time equals 5 minutes.

For Both Methods

Flow rate 3.0 mL/min, 400 µL was split via a zero dead volume tee piece which passes into the mass spectrometer. Wavelength detection range: 220 to 400 nm. Function type: diode array (535 scans). Column: Phenomenex Onyx Monolithic C18 50×4.60 mm.

The reverse phase flash purification conditions were as follows: The Flash purification system (Varian 971-Fp) was run using a mobile phase of water (A) and acetonitrile (B). Gradient: initial composition 5% B over 20 C.V. (Column Volume) then 5% B to 70% B within 60 C.V. The composition was held for 15 C.V. at 95% B, and then returned to 5% B in 5 C.V. and held at 5% B for 10 C.V. Total gradient run time equals 120 C.V. Flow rate 6.0 mL/min. Wavelength detection range: 254 nm. Column: Agilent AX1372-1 SF10-5.5gC8.

Preparative HPLC: Reverse-phase ultra-high-performance liquid chromatography (UPLC) was carried out on Phenomenex Gemini NX 5µ C-18 columns of the following dimensions: 150×4.6 mm for analysis, and 150×21.20 mm for preparative work. All UPLC experiments were performed with gradient conditions. Eluents used were solvent A ($H_2O$ with 0.1% Formic acid) and solvent B ($CH_3CN$ with 0.1% Formic acid). Flow rates used were 1.0 ml/min for analytical, and 20.0 ml/min for preparative HPLC. Detection was at 254 and 280 nm.

Synthesis of Intermediate 12

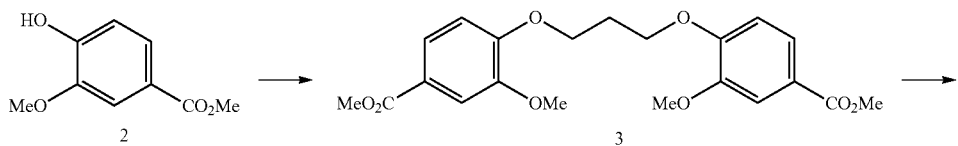

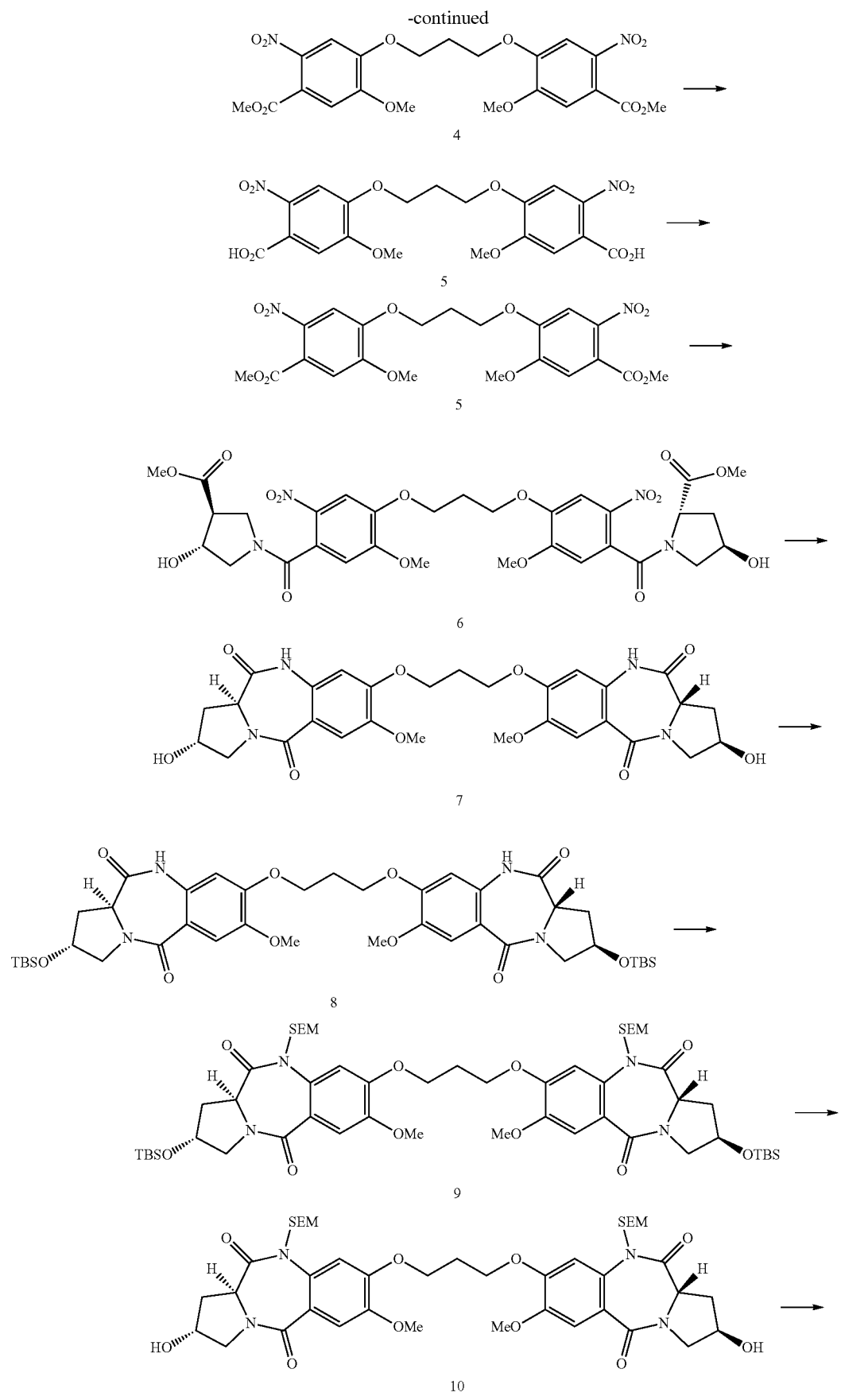

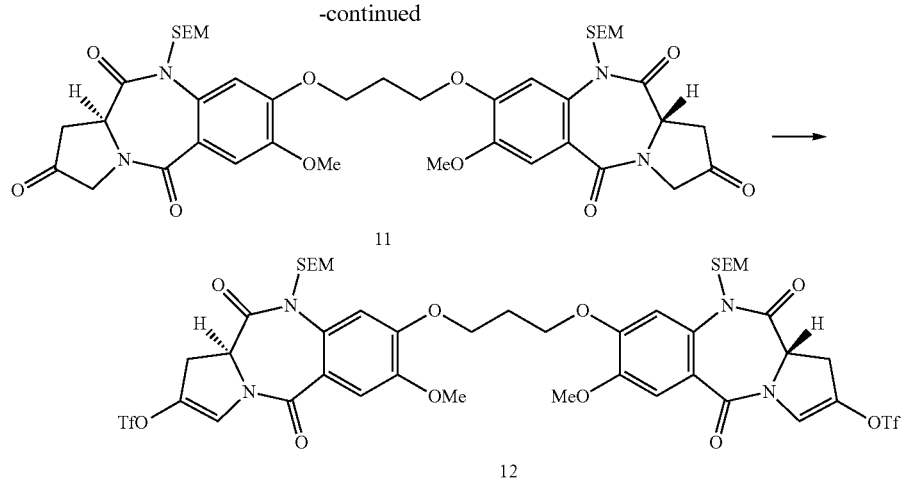

(a) 1',3'-Bis[2-methoxy-4-(methoxycarbonyl)phenoxy]propane (3)

Diisopropyl azodicarboxylate (71.3 mL, 73.2 g, 362 mmol) was added drop-wise over a period of 60 min to an overhead stirred solution of methyl vanillate 2 (60.0 g, 329 mmol) and Ph$_3$P (129.4 g, 494 mmol) in anhydrous THF (800 mL) at 0-5° C. (ice/acetone) under a nitrogen atmosphere. The reaction mixture was allowed to stir at 0-5° C. for an additional 1 hour after which time a solution of 1,3-propanediol (11.4 mL, 12.0 g, 158 mmol) in THF (12 mL) was added drop-wise over a period of 20 min. The reaction mixture was allowed to warm to room temperature and stirred for 5 days. The resulting white precipitate 3 was collected by vacuum filtration, washed with THF and dried in a vacuum desiccator to constant weight. Yield=54.7 g (84% based on 1,3-propanediol). Purity satisfactory by LC/MS (3.20 min (ES+) m/z (relative intensity) 427 ([M+Na]$^{+}$, 10); $^1$H NMR (400 MHz, CDCl$_3$) δ 7.64 (dd, 2H, J=1.8, 8.3 Hz), 7.54 (d, 2H, J=1.8 Hz), 6.93 (d, 2H, J=8.5 Hz), 4.30 (t, 4H, J=6.1 Hz), 3.90 (s, 6H), 3.89 (s, 6H), 2.40 (p, 2H, J=6.0 Hz).

(b) 1',3'-Bis[2-methoxy-4-(methoxycarbonyl)-5-nitrophenoxy]propane (4)

Solid Cu(NO$_3$)$_2$.3H$_2$O (81.5 g, 337.5 mmol) was added slowly to an overhead stirred slurry of the bis-ester 3 (54.7 g, 135 mmol) in acetic anhydride (650 mL) at 0-5° C. (ice/acetone). The reaction mixture was allowed to stir for 1 hour at 0-5° C. and then allowed to warm to room temperature. A mild exotherm (ca. 40-50° C.), accompanied by thickening of the mixture and evolution of NO$_2$ was observed at this stage. Additional acetic anhydride (300 mL) was added and the reaction mixture was allowed to stir for 16 hours at room temperature. The reaction mixture was poured on to ice (~1.5 L), stirred and allowed to return to room temperature. The resulting yellow precipitate was collected by vacuum filtration and dried in a desiccator to afford the desired bis-nitro compound 4 as a yellow solid. Yield=66.7 g (100%). Purity satisfactory by LC/MS (3.25 min (ES+) m/z (relative intensity) 517 ([M+Na]$^{+}$, 40); $^1$H NMR (400 MHz, CDCl$_3$) δ 7.49 (s, 2H), 7.06 (s, 2H), 4.32 (t, 4H, J=6.0 Hz), 3.95 (s, 6H), 3.90 (s, 6H), 2.45-2.40 (m, 2H).

(c) 1',3'-Bis(4-carboxy-2-methoxy-5-nitrophenoxy)propane (5)

A slurry of the methyl ester 4 (66.7 g, 135 mmol) in THF (700 mL) was treated with 1N NaOH (700 mL) and the reaction mixture was allowed to stir vigorously at room temperature. After 4 days stirring, the slurry became a dark coloured solution which was subjected to rotary evaporation under reduced pressure to remove THF. The resulting aqueous residue was acidified to pH 1 with concentrated HCl and the colourless precipitate 5 was collected and dried thoroughly in a vacuum oven (50° C.). Yield=54.5 g (87%). Purity satisfactory by LC/MS (2.65 min (ES+) m/z (relative intensity) 489 ([M+Na]$^{+}$, 30)); $^1$H NMR (400 MHz, DMSO-d$_6$) δ 7.62 (s, 2H), 7.30 (s, 2H), 4.29 (t, 4H, J=6.0 Hz), 3.85 (s, 6H), 2.30-2.26 (m, 2H).

(d) 1,1'-[[(Propane-1,3-diyl)dioxy]bis[(5-methoxy-2-nitro-1,4-phenylene) carbonyl]]bis[(2S,4R)-methyl-4-hydroxypyrrolidine-2-carboxylate] (6)

Oxalyl chloride (24.5 mL, 35.6 g, 281 mmol) was added to a stirred suspension of the nitrobenzoic acid 5 (43 g, 92.3 mmol) and DMF (6 mL) in anhydrous DCM (600 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation under reduced pressure; the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 min to a stirred suspension of (2S,4R)-methyl-4-hydroxypyrrolidine-2-carboxylate hydrochloride (38.1 g, 210 mmol) and TEA (64.5 mL, g, 463 mmol) in DCM (400 mL) at −40° C. (dry ice/CH$_3$CN). Immediately, the reaction was complete as judged by LC/MS (2.47 min (ES+) m/z (relative intensity) 721 ([M+H]$^{+}$, 100). The mixture was diluted with DCM (200 mL) and washed with 1N HCl (300 mL), saturated NaHCO$_3$ (300 mL), brine (400 mL), dried (MgSO$_4$), filtered and the solvent evaporated in vacuo to give the pure product 6 as an orange solid (66.7 g, 100%).

[α]$^{22}_D$=−46.1° (c=0.47, CHCl$_3$); $^1$H NMR (400 MHz, CDCl$_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, CDCl$_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl$_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^{+•}$, 47), 388 (80); HRMS [M+H]$^{+•}$ theoretical C$_{31}$H$_{36}$N$_4$O$_{16}$ m/z 721.2199, found (ES$^+$) m/z 721.2227.

(e) 1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (7)

Method A:

A solution of the nitro-ester 6 (44 g, 61.1 mmol) in MeOH (2.8 L) was added to freshly purchased Raney® nickel (~50 g of a ~50% slurry in H$_2$O) and anti-bumping granules in a 5 L 3-neck round bottomed flask. The mixture was heated at reflux and then treated dropwise with a solution of hydrazine hydrate (21.6 mL, 22.2 g, 693 mmol) in MeOH (200 mL) at which point vigorous effervescence was observed. When the addition was complete (~45 min) additional Raney® nickel was added carefully until effervescence had ceased and the initial yellow colour of the reaction mixture was discharged. The mixture was heated at reflux for a further 5 min at which point the reaction was deemed complete by TLC (90:10 v/v CHCl$_3$/MeOH) and LC/MS (2.12 min (ES+) m/z (relative intensity) 597 ([M+H]$^{+•}$, 100)). The reaction mixture was filtered hot immediately through a sinter funnel containing celite with vacuum suction. The filtrate was reduced in volume by evaporation in vacuo at which point a colourless precipitate formed which was collected by filtration and dried in a vacuum desiccator to provide 7 (31 g, 85%). [α]$^{27}_D$=+404° (c=0.10, DMF); $^1$H NMR (400 MHz, DMSO-d$_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-de) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^{+•}$, 10), 597 ([M+H]$^{+•}$, 52), 445 (12), 326 (11); HRMS [M+H]$^{+•}$ theoretical C$_{29}$H$_{32}$N$_4$O$_{10}$ m/z 597.2191, found (ES$^+$) m/z 597.2205.

Method B:

A suspension of 10% Pd/C (7.5 g, 10% w/w) in DMF (40 mL) was added to a solution of the nitro-ester 6 (75 g, 104 mmol) in DMF (360 mL). The suspension was hydrogenated in a Parr hydrogenation apparatus over 8 hours. Progress of the reaction was monitored by LC/MS after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2:1 volume of precipitate) and dried in a vacuum desiccator to provide 7 (50 g, 81%). Analytical data for method B: Identical to those obtained for Method A (optical rotation, $^1$H NMR, LC/MS and TLC).

(f) 1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (8)

TBSCl (27.6 g, 182.9 mmol) and imidazole (29.9 g, 438.8 mmol) were added to a cloudy solution of the tetralactam 7 (21.8 g, 36.6 mmol) in anhydrous DMF (400 mL) at 0° C. (ice/acetone). The mixture was allowed to stir under a nitrogen atmosphere for 3 hours after which time the reaction was deemed complete as judged by LC/MS (3.90 min (ES+) m/z (relative intensity) 825 ([M+H]$^{+•}$, 100). The reaction mixture was poured onto ice (~1.75 L) and allowed to warm to room temperature with stirring. The resulting white precipitate was collected by vacuum filtration, washed with H$_2$O, diethyl ether and dried in the vacuum desicator to provide pure 8 (30.1 g, 99%). [α]$^{23}_D$=+234° (c=0.41, CHCl$_3$); $^1$H NMR (400 MHz, CDCl$_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, CDCl$_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl$_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) m/z (relative intensity) 825 ([M+H]$^{+•}$, 62), 721 (14), 440 (38); HRMS [M+H]$^{+•}$ theoretical C$_{41}$H$_{60}$N$_4$O$_{10}$Si$_2$ m/z 825.3921, found (ES$^+$) m/z 825.3948.

(g) 1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (9)

A solution of n-BuLi (68.3 mL of a 1.6 M solution in hexane, 109 mmol) was added dropwise to a stirred suspension of the tetralactam 8 (30.08 g, 36.4 mmol) in anhydrous THF (600 mL) at −30° C. (dry ice/ethylene glycol) under a nitrogen atmosphere. The reaction mixture was allowed to stir at this temperature for 1 hour (now a reddish orange colour) at which point a solution of SEMCl (19.3 mL, 18.2 g, 109 mmol) in anhydrous THF (120 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^{+•}$, 100). The THF was removed by evaporation in vacuo and the resulting residue dissolved in EtOAc (750 mL), washed with H$_2$O (250 mL), brine (250 mL), dried (MgSO$_4$) filtered and evaporated in vacuo to provide the crude N10-SEM-protected tetralactam 9 as an oil (max$^m$ 39.5 g, 100%). Product carried through to next step without purification. [α]$^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, -1.24, -4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^{+\bullet}$, 48), 1085 ([M+H]$^{+\bullet}$, 100), 1009 (5), 813 (6); HRMS [M+H]$^{+\bullet}$ theoretical C$_{53}$H$_{88}$N$_4$O$_{12}$Si$_4$ m/z 1085.5548, found (ES$^+$) m/z 1085.5542.

(h) 1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (10)

A solution of TBAF (150 mL of a 1.0 M solution in THF, 150 mmol) was added to a stirred solution of the crude bis-silyl ether 9 [84.0 g (max$^m$ 56.8 g), 52.4 mmol] in THF (800 mL) at room temperature. After stirring for 1 hour, analysis of the reaction mixture by TLC (95:5 v/v CHCl$_3$/MeOH) revealed completion of reaction. The THF was removed by evaporation under reduced pressure at room temperature and the resulting residue dissolved in EtOAc (500 mL) and washed with NH$_4$Cl (300 mL). The combined organic layers were washed with brine (60 mL), dried (MgSO$_4$), filtered and evaporated under reduced pressure to provide the crude product. Purification by flash chromatography (gradient elution: 100% CHCl$_3$ to 96:4 v/v CHCl/MeOH) gave the pure tetralactam 10 as a white foam (36.0 g, 79%). LC/MS 3.33 min (ES+) m/z (relative intensity) 879 ([M+Na]$^{+\bullet}$, 100), 857 ([M+H]$^{+\bullet}$, 40); [α]$^{23}_D$=+202° (c=0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, -1.23; IR (ATR, CHCl$_3$) 2956, 1684, 1625, 1604, 1518, 1464, 1434, 1361, 1238, 1058, 1021 cm$^{-1}$; MS (ES$^+$) m/z (relative intensity) 885 ([M+29]$^{+\bullet}$, 70), 857 ([M+H]$^{+\bullet}$, 100), 711 (8), 448 (17); HRMS [M+H]$^{+\bullet}$ theoretical C$_{41}$H$_{60}$N$_4$O$_{12}$Si$_2$ m/z 857.3819, found (ES$^+$) m/z 857.3826.

(i) 1,1'-[[(Propane-1,3-diyl)dioxy]bis(11aS)-7-methoxy-2-oxo-10-((2-(trimethylsilyl)ethoxy)methyl)-1,2,3,10,11,11a-hexahydro-5H-pyrrolo[2,1-c][1,4]-benzodiazepin-5,11-dione] (11)

Diol 10 (25.6 g, 30 mmol, 1 eq.), NaOAc (6.9 g, 84 mmol, 2.8 eq.) and TEMPO (188 mg, 1.2 mmol, 0.04 eq.) were dissolved in DCM (326 mL) under Ar. This was cooled to -8° C. (internal temperature) and TCCA (9.7 g, 42 mmol, 1.4 eq.) was added portionwise over 15 minutes. TLC (EtOAc) and LC/MS [3.60 min. (ES+) m/z (relative intensity) 854.21 ([M+H]$^{+\bullet}$, 40), (ES−) m/z (relative intensity) 887.07 ([M−H+Cl]$^{−\bullet}$, 10)] after 30 minutes indicated that reaction was complete. Cold DCM (200 mL) was added and the mixture was filtered through a pad of Celite before washing with a solution of saturated sodium hydrogen carbonate/sodium thiosulfate (1:1 v/v; 200 mL x 2). The organic layer was dried with MgSO$_4$, filtered and the solvent removed in vacuo to yield a yellow/orange sponge (25.4 g, 99%). LC/MS [3.60 min. (ES+) m/z (relative intensity) 854.21 ([M+H]$^{+\bullet}$, 40); [α]$^{20}_D$=+291° (c=0.26, CHCl$_3$); $^1$H NMR (400 MHz, CDC$_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}$C NMR (100 MHz, CDCl$_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, -1.24; IR (ATR, CHCl$_3$) 2957, 1763, 1685, 1644, 1606, 1516, 1457, 1434, 1360, 1247, 1209, 1098, 1066, 1023 cm$^{-1}$; MS (ES$^+$) m/z (relative intensity) 881 ([M+29]$^{+\bullet}$, 38), 853 ([M+H]$^{+\bullet}$, 100), 707 (8), 542 (12); HRMS [M+H]$^{+\bullet}$ theoretical C$_{41}$H$_{56}$N$_4$O$_{12}$Si$_2$ m/z 853.3506, found (ES$^+$) m/z 853.3502.

(j) 1,1'-[[(Propane-1,3-diyl) dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (12)

Anhydrous 2,6-lutidine (5.15 mL, 4.74 g, 44.2 mmol) was injected in one portion to a vigorously stirred solution of bis-ketone 11 (6.08 g, 7.1 mmol) in dry DCM (180 mL) at -45°C (dry ice/acetonitrile) under a nitrogen atmosphere. Anhydrous triflic anhydride, taken from a freshly opened ampoule (7.2 mL, 12.08 g, 42.8 mmol), was injected rapidly dropwise, while maintaining the temperature at -40° C. or below. The reaction mixture was allowed to stir at -45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated NaHCO$_3$ (200 mL), brine (100 mL) and dried (MgSO$_4$). Filtration and evaporation of the solvent under reduced pressure afforded the crude product which was purified by flash column chromatography (gradient elution: 90:10 v/v n-hexane/EtOAc to 70:30 v/v n-hexane/EtOAc) to afford bis-enol triflate 12 as a yellow foam (5.5 g, 70%). LC/MS 4.32 min (ES+) m/z (relative intensity) 1139 ([M+Na]$^{+\bullet}$, 20); [α]$^{24D}$=+2710 (c=0.18, CHCl$_3$); $^1$H NMR (400 MHz, CDCl$_3$) δ 7.33 (s, 2H), 7.26 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H); $^{13}$C NMR (100 MHz, CDCl$_3$) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, -1.25; IR (ATR, CHCl$_3$) 2958, 1690, 1646, 1605, 1517, 1456, 1428, 1360, 1327, 1207, 1136, 1096, 1060, 1022, 938, 913 cm$^{-1}$; MS (ES$^+$) m/z (relative intensity) 1144 ([M+28]$^{+\bullet}$, 100), 1117 ([M+H]$^{+\bullet}$, 48), 1041 (40), 578 (8); HRMS [M+H]$^{+\bullet}$ theoretical C$_{43}$H$_{54}$N$_4$O$_{16}$Si$_2$S$_2$F$_6$ m/z 1117.2491, found (ES$^+$) m/z 1117.2465.

Example 1
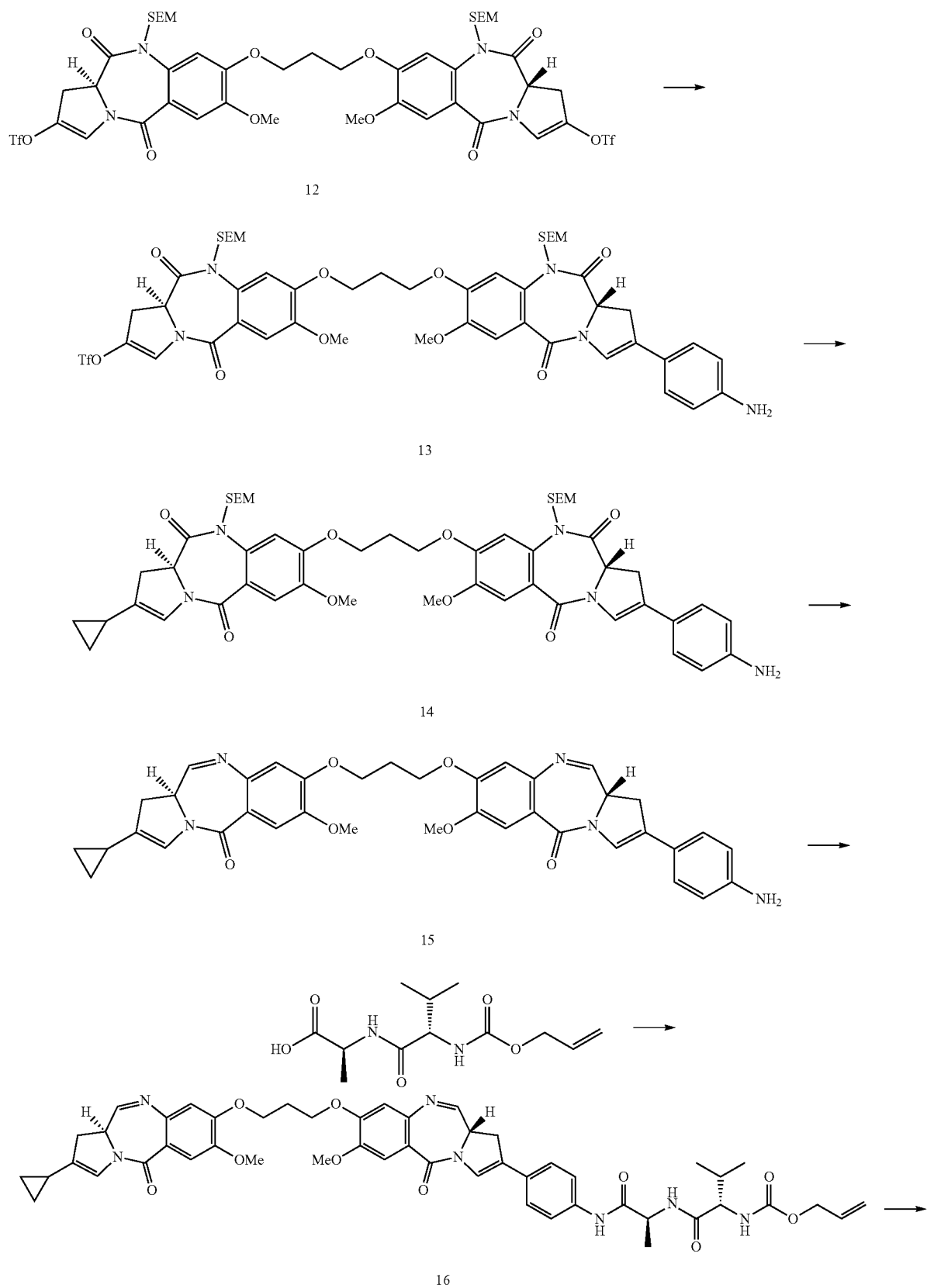

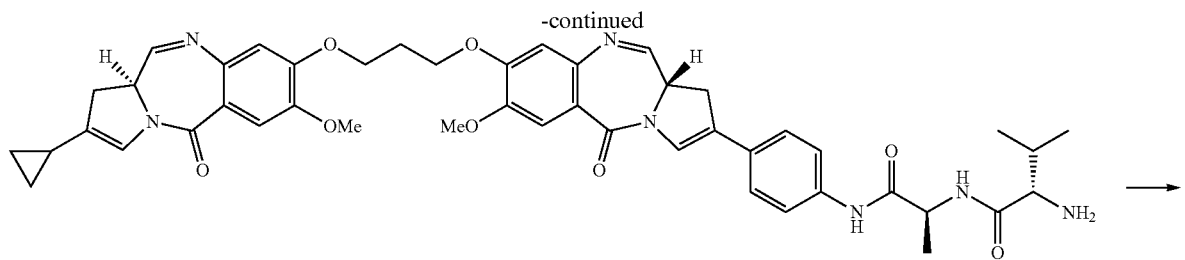

17

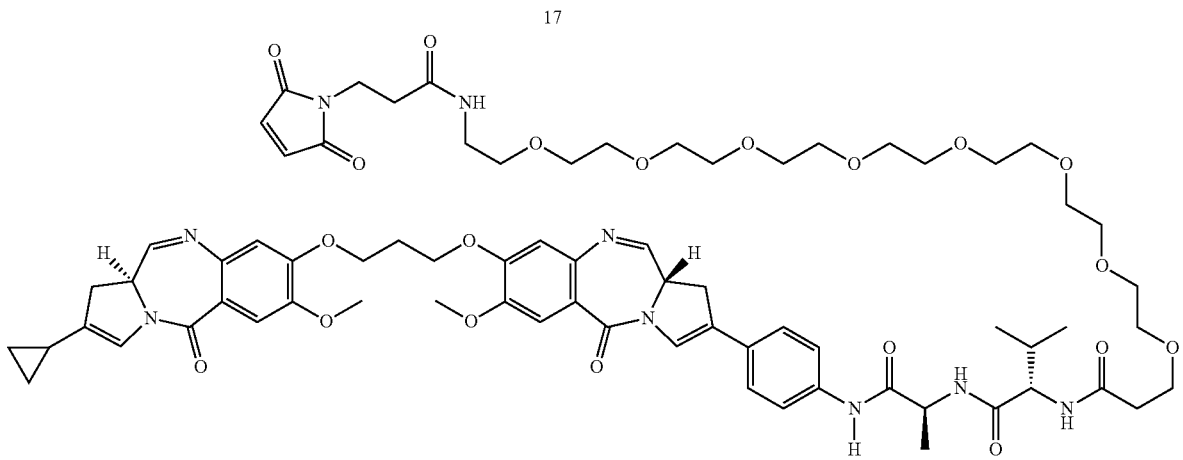

18

(a) (S)-8-(3-(((S)-2-(4-aminophenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (13)

Pd(PPh$_3$)$_4$ (116.9 mg, 0.101 mmol) was added to a stirred mixture of the bis-enol triflate 12. (5.65 g, 5.06 mmol), 4-Aminophenylboronic acid pinacol ester (1 g, 4.56 mmol), Na$_2$CO$_3$ (2.46 g, 23.2 mmol), MeOH (37 mL), toluene (74 mL) and water (37 mL). The reaction mixture was allowed to stir at 30° C. under a nitrogen atmosphere for 24 hours after which time all the boronic ester has consumed. The reaction mixture was then evaporated to dryness before the residue was taken up in EtOAc (150 mL) and washed with H$_2$O (2×100 mL), brine (150 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 13 as a yellowish foam (2.4 g, 45%). LC/MS 4.02 min (ES+) m/z (relative intensity) 1060.21 ([M+H]$^{+\bullet}$, 100); $^1$H-NMR: (CDCl$_3$, 400 MHz) δ 7.40 (s, 1H), 7.33 (s, 1H), 7.27 (bs, 3H), 7.24 (d, 2H, J=8.5 Hz), 7.15 (t, 1H, J=2.0 Hz), 6.66 (d, 2H, J=8.5 Hz), 5.52 (d, 2H, J=10.0 Hz), 4.77 (d, 1H, J=10.0 Hz), 4.76 (d, 1H, J=10.0 Hz), 4.62 (dd, 1H, J=3.7, 11.0 Hz), 4.58 (dd, 1H, J=3.4, 10.6 Hz), 4.29 (t, 4H, J=5.6 Hz), 4.00-3.85 (m, 8H), 3.80-3.60 (m, 4H), 3.16 (ddd, 1H, J=2.4, 11.0, 16.3 Hz), 3.11 (ddd, 1H, J=2.2, 10.5, 16.1 Hz), 2.43 (p, 2H, J=5.9 Hz), 1.1-0.9 (m, 4H), 0.2 (s, 18H). $^{13}$C-NMR: (CDCl$_3$, 100 MHz) δ 169.8, 168.3, 164.0, 162.7, 153.3, 152.6, 149.28, 149.0, 147.6, 139.6, 134.8, 134.5, 127.9, 127.5, 125.1, 123.21, 121.5, 120.5, 120.1, 116.4, 113.2, 108.7, 79.8, 79.6; 68.7, 68.5, 67.0, 66.8, 58.8, 58.0, 57.6, 32.8, 32.0, 30.3, 19.7, 0.25

(b) (S)-2-(4-Aminophenyl)-8-(3-(((S)-2-cyclopropyl-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-10-((2-(trimethylsilyl)ethoxy)methyl)-1H-benzo[e]pyrrolo[1,2-a][1,4]diazepine-5,11(10H,11aH)-dione (14)

Triphenylarsine (0.24 g, 0.8 mmol), silver (I) oxide (1.02 g, 4.4 mmol), cyclopropylboronic acid (0.47 g, 5.5 mmol) and starting material 13 (1.15 g, 1.1 mmol) were dissolved in dioxane (30 mL) under an argon atmosphere. Potassium phosphate tribasic (2.8 g, 13.2 mmol) was ground-up with a pestle and mortar and quickly added to the reaction mixture. The reaction mixture was evacuated and flushed with argon 3 times and heated to 71° C. Palladium (II) bis (benzonitrile chloride) (84 mg, 0.22 mmol) was added and the reaction vessel was evacuated and flushed with argon 3 times. After 10 minutes a small sample was taken for analysis by TLC (80:20 v/v ethyl acetate/hexane) and LC/MS. After 30 minutes the reaction had gone to completion (LC/MS analysis indicated complete consumption of starting material) and the reaction was filtered through celite and the filter pad washed with ethyl acetate (400 mL). The filtrate was washed with water (2×200 mL) and brine (2×200 mL). The organic layer was dried with MgSO$_4$, filtered and the solvent removed in vacuo. Purification by silica gel column chromatography (30:70 v/v Hexane/Ethyl acetate) afforded the product 14 as an orange/yellow solid (0.66 g, 63%). Method 1, LC/MS (3.85 min (ES$^+$) m/z (relative intensity) 952.17 ([M+H]$^{+\bullet}$, 100). $^1$H NMR (400 MHz, CDCl$_3$) δ 7.36 (d, 2H, J=8.4 Hz), 7.30 (s, 1H), 7.25-7.19 (m, 4H), 6.68 (s, 1H), 6.62 (d, 2H, J=8.4 Hz), 5.49 (dd, 2H, J=5.6, 10.0 Hz), 4.73 (app. t, 2H, J=10.8 Hz), 4.54 (dd, 1H, J=3.2, 10.4 Hz), 4.40 (dd, 1H, J=3.2, 10.4 Hz), 4.29-4.23 (m, 4H), 3.91-3.85 (m, 7H), 3.80-3.71 (m, 2H), 3.70-3.61 (m, 2H), 3.38-3.32 (m, 1H), 3.12-3.01 (m, 1H), 2.50-2.69 (m, 1H), 2.40 (q, 2H, J=5.6 Hz), 1.50-1.43 (m, 1H), 0.99-0.71 (m, 6H), 0.54-0.59 (m, 2H), 0.00 (s, 18H) ppm.

(c) (S)-2-(4-Aminophenyl)-8-(3-(((S)-2-cyclopropyl-7-methoxy-5-oxo-5,11a-dihydro-1H-benzo[e]pyrrolo[1,2-a][1,4]diazepin-8-yl)oxy)propoxy)-7-methoxy-1H-benzo[e]pyrrolo[1,2-a][1,4]diazepin-5(11aH)-one (15)

SEM dilactam 14 (0.66 g, 0.69 mmol) was dissolved in THF (23 mL) and cooled to −78° C. under an argon atmosphere. Super-Hydride® solution (1.7 mL, 1 M in THF) was added drop wise over 5 minutes while monitoring the temperature. After 20 minutes a small sample was taken and washed with water for LC/MS analysis. Water (50 mL) was added and the cold bath was removed. The organic layer was extracted and washed with brine (60 mL). The combined aqueous layers were washed with $CH_2Cl_2$/MeOH (90/10 v/v) (2×50 mL). The combined organic layers were dried with $MgSO_4$, filtered and the solvent removed in vacuo. The crude product was dissolved in MeOH (48 mL), $CH_2Cl_2$ (18 mL) and water (6 mL) and sufficient silica gel was added to afford a thick suspension. After 5 days stirring, the suspension was filtered through a sintered funnel and washed with $CH_2Cl_2$/MeOH (9:1) (~200 mL) until product ceased to be eluted. The organic layer was washed with brine (2×70 mL), dried with $MgSO_4$, filtered and the solvent removed in vacuo. Purification by silica gel column chromatography (100% $CHCl_3$ to 96/4 v/v $CHCl_3$/MeOH) afforded the product 15 as a yellow solid (302 mg, 66%). Method 1, LC/MS (2.42 min (ES$^+$) m/z (relative intensity) 660.74 ([M+H]$^{+•}$, 30). $^1$H NMR (400 MHz, $CDCl_3$) δ 7.86 (d, 1H, J=3.6 Hz), 7.78 (d, 1H, J=3.6 Hz), 7.58-7.44 (m, 3H), 7.34-7.20 (m, 3H), 6.88-6.66 (m, 4H), 4.35-4.15 (m, 6H), 3.95-3.75 (m, 7H), 3.39-3.22 (m, 1H), 3.14-3.04 (m, 1H), 2.93-2.85 (m, 1H), 2.46-2.36 (m, 2H), 1.49-1.41 (m, 1H), 0.80-0.72 (m, 2H), 0.58-0.51 (app. s, 2H) ppm.

(d) Allyl ((2S)-1-(((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methy-1-oxobutan-2-yl) carbamate (16)

In a degassed round bottom flask filled with argon, HO-Ala-Val-alloc (149.6 mg, 0.549 mmol) and EEDQ (135.8 mg, 0.549 mmol) were dissolved in a 9:1 mixture of dry $CH_2Cl_2$/MeOH (5 mL). The flask was wrapped in aluminium foil and the reaction mixture was allowed to stir at room temperature for 1 hour before starting material 15 (302 mg, 0.457 mmol) was added.

The reaction mixture was left to stir for a further 40 hours at room temperature before the volatiles were removed by rotary evaporation under reduced pressure (the reaction was followed by LC/MS, RT starting material 2.32 min, (ES$^+$ 660.29 ([M+H]$^{+•}$, 100)). The crude product was directly purified by silica gel chromatography column (100% $CHCl_3$ to 90/10 v/v $CHCl_3$/MeOH) to afford the pure product (16) in 42% yield (174 mg). Method 2 LC/MS (2.70 min (ES+) m/z (relative intensity) 914.73 ([M+H]$^{+•}$, 60), 660.43 (60), 184.31 (100)).

(e) (2S)-2-amino-N-((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)-3-methylbutanamide (17)

The starting material 16 (170 mg, 0.185 mmol) was dissolved in dry $CH_2Cl_2$ (5 mL) in a round bottom flask filled with argon, before pyrrolidine (41 µL, 0.21 mmol) was added. The flask was purged/refilled three times with argon before Pd(PPh$_3$)$_4$ (14 mg, 0.084 mmol) was added and the flushing operation repeated. After 1 hour, complete consumption of starting material was observed (the reaction was followed by LC/MS) and $Et_2O$ (50 mL) was added to the reaction mixture which was allowed to stir until all the product had crashed out of solution. The solid was filtered through a sintered funnel and washed twice with $Et_2O$ (2×25 mL). The collecting flask was replaced and the isolated solid was dissolved in $CHCl_3$ (100 mL or until all the product had passed through the sintered funnel). The volatiles were then removed by rotary evaporation under reduced pressure to afford the crude product 17 which was used directly in the next step (168 mg). LC/MS method 2 (2.70 min (ES+) m/z (relative intensity) 830.27 ([M+H]$^{+•}$, 50), 660.13 (80), 171.15 (100)).

(f) N—((R)-1-(((S)-1-((4-((S)-8-(3-(((S)-2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-1-(3-(2,5-dioxo-2,5-dihydro-1H-pyrrol-1-yl)propanamido)-3,6,9,12,15,18,21,24-octaoxaheptacosan-27-amide (18)

Starting material 17 (154 mg, 0.185 mmol) and EDCl.HCl (110 mg, 0.185 mmol) were solubilised in dry $CH_2Cl_2$ (5 mL) in a round bottom flask purged and filled with argon. The mixture was left to stir at room temperature for 1 hour before PEG$_8$-maleimide (35.6 mg, 0.185 mmol) was added and the reaction mixture stirred for a further 16 hours (or until the reaction is complete, monitored by LC/MS). The reaction solution was diluted with $CH_2Cl_2$ (50 mL) and the organics were washed with $H_2O$ (50 mL) and brine (50 mL) before being dried with $MgSO_4$, filtered and the solvent removed by rotary evaporation under reduced pressure to afford the crude product. Purification on silica gel column chromatography (100% $CHCl_3$ to 85/15 v/v $CHCl_3$/MeOH) gave the desired product (135 mg), however remaining traces of unreacted PEG$_8$-maleimide were observed (by LC/MS, 2.21 min, method 2). Automated reverse phase silica gel chromatography ($H_2O$/$CH_3CN$) (see general information for conditions) successfully removed the impurity affording pure final product (18, 37 mg of pure product starting from 110 mg, 33%). Overall yield=17%. Method 2 LC/MS (2.58 min (ES+) m/z (relative intensity) 1404.03 ([M+H]+•, 20), 702.63 (100)). $^1$H NMR (400 MHz, $CDCl_3$) δ 7.91 (t, J=3.5 Hz, 1H), 7.80 (d, J=4.0 Hz, 1H), 7.75 (d, J=8.8 Hz, 1H), 7.69 (d, J=8.7 Hz, 1H), 7.54-7.50 (m, 2H), 7.45 (s, 1H), 7.39-7.31 (m, 2H), 6.87 (d, J=10.5 Hz, 2H), 6.76 (s, 1H), 6.72-6.68 (m, 2H), 4.74-4.62 (m, 1H), 4.45-

4.17 (m, 7H), 3.95 (s, 3H), 3.94 (s, 3H), 3.67-3.58 (m, 34H), 3.54 (m, 2H), 3.42 (dd, J=10.2, 5.2 Hz, 2H), 3.16-3.07 (m, 1H), 2.92 (dd, J=16.1, 4.1 Hz, 1H), 2.62-2.49 (m, 4H), 2.48-2.39 (m, 2H), 2.37-2.25 (m, 1H), 1.92 (s, 1H), 1.52-
1.44 (m, 3H), 1.10-0.93 (m, 6H), 0.79 (dd, J=9.2, 5.3 Hz, 2H), 0.57 (dd, J=9.2, 5.3 Hz, 2H), NH were not observed.
Example 2
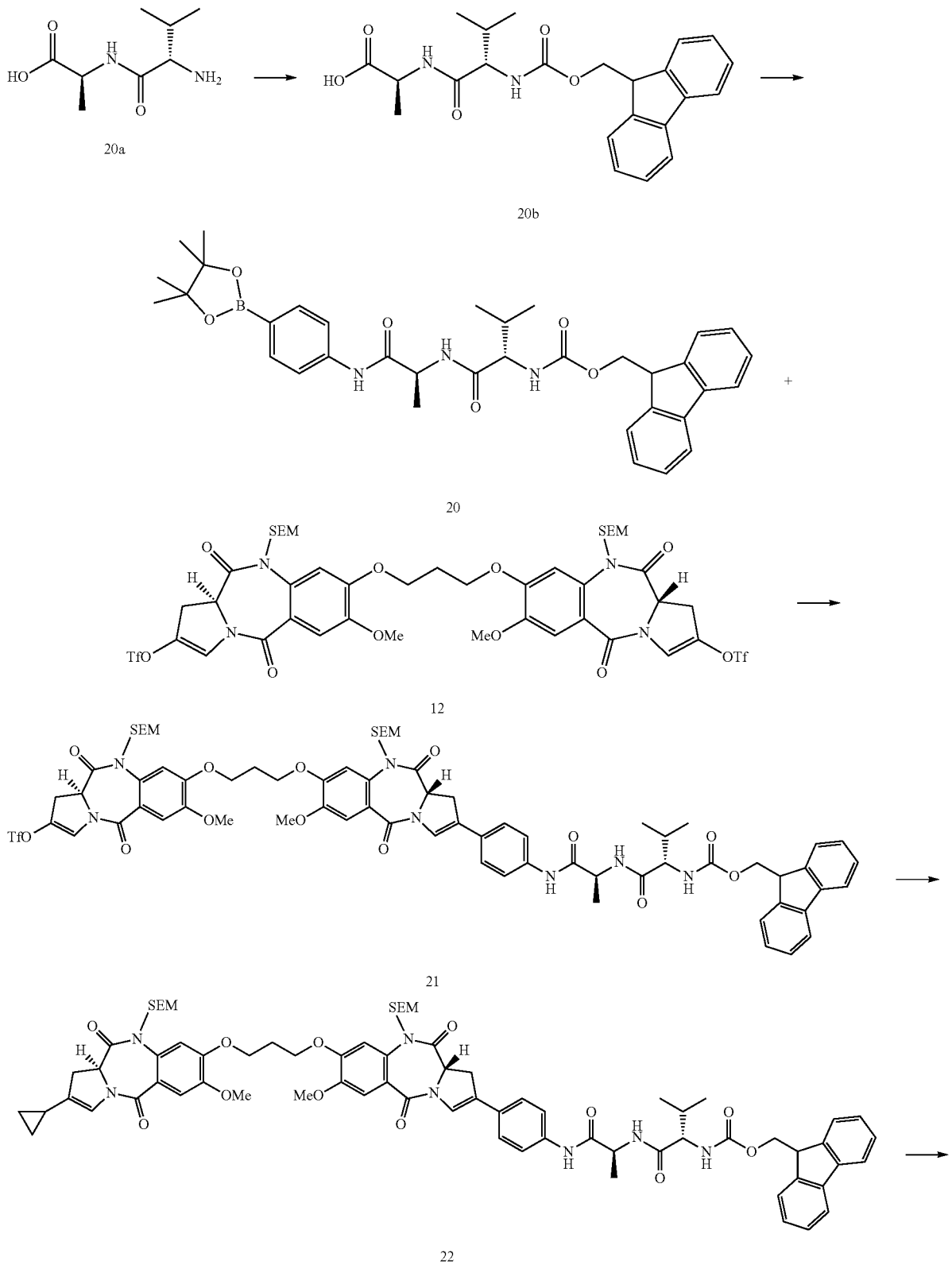

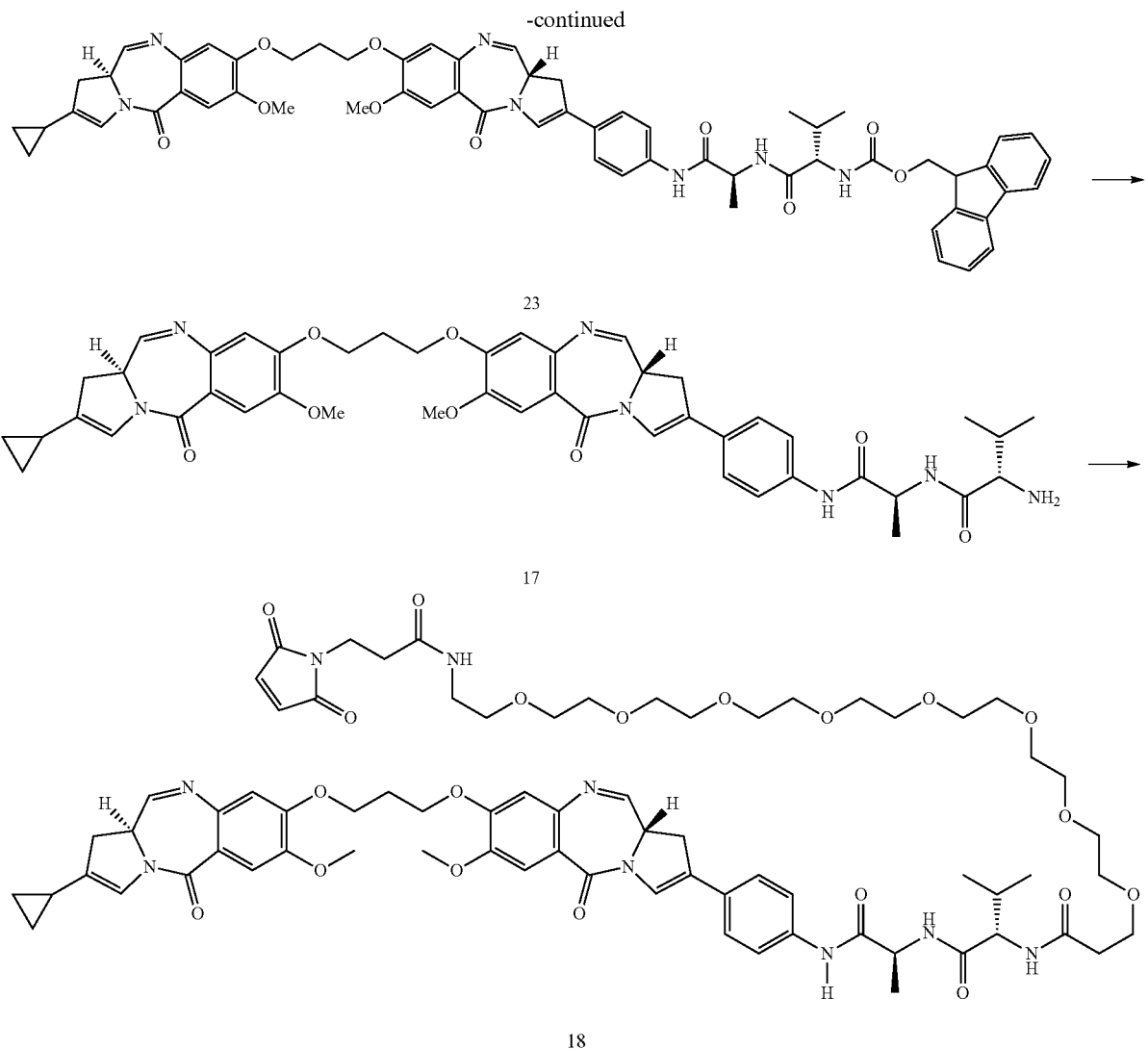

(a) (R)-2-((R)-2-((((9H-fluoren-9-yl)methoxy)carbonyl)amino)-3-methylbutanamido) propanoic acid (20b)

HO-Ala-Val-H 20a (350 mg, 1.86 mmol) and Na$_2$CO$_3$ (493 mg, 4.65 mmol) were dissolved in distilled H$_2$O (15 mL) and the mixture was cooled to 0° C. before dioxane (15 mL) was added (partial precipitation of the amino acid salt occurred). A solution of Fmoc-Cl (504 mg, 1.95 mmol) in dioxane (15 mL) was added dropwise with vigorous stirring over 10 minutes. The resulting mixture was stirred at 00C for 2 hours before the ice bath was removed and stirring was maintained for 16 hours. The solvent was removed by rotary evaporation under reduced pressure and the residue dissolved in water (150 mL). The pH was adjusted from 9 to 2 with 1N HCl and the aqueous layer was subsequently extracted with EtOAc (3×100 mL). The combined organics were washed with brine (100 mL), dried with MgSO$_4$, filtered and the volatiles removed by rotary evaporation under reduced pressure to afford pure HO-Ala-Val-Fmoc 20b (746 mg, 97% yield). LC/MS 2.85 min (ES+) m/z (relative intensity) 410.60; $^1$H-NMR (400 MHz, CDCl$_3$) δ 7.79 (d, J=7.77 Hz, 2H), 7.60 (d, J=7.77 Hz, 2H), 7.43 (d, J=7.5 Hz, 2H), 7.34 (d, J=7.5 Hz, 2H), 6.30 (bs, 1H), 5.30 (bs, 1H), 4.71-7.56 (m, 1H), 4.54-4.36 (m, 2H), 4.08-3.91 (m, 1H), 2.21-2.07 (m, 1H), 1.50 (d, J=7.1 Hz, 3H), 1.06-0.90 (m, 6H).

(b) (9H-fluoren-9-yl)methyl ((S)-3-methyl-1-oxo-1-(((S)-1-oxo-1-((4-(4,4,5,5-tetramethyl-1,3,2-dioxaborolan-2-yl)phenyl)amino)propan-2-yl)amino)butan-2-yl)carbamate (20)

4-Aminophenylboronic acid pinacol ester was added (146.9 mg, 0.67 mmol) was added to a solution of HO-Ala-Val-Fmoc 20b (330 mg, 0.8 mmol), DCC (166 mg, 0.8 mmol) and DMAP (5 mg, cat.) in dry DCM (8 mL) previously stirred for 30 minutes at room temperature in a flask flushed with argon. The reaction mixture was then allowed to stir at room temperature overnight. The reaction was followed by LCMS and TLC. The reaction mixture was diluted with CH$_2$Cl$_2$ and the organics were washed with H$_2$O and brine before being dried with MgSO$_4$, filtered and the solvent removed by rotary evaporation under reduced pressure. The crude product was dry loaded on a silica gel chromatography column (Hexane/EtOAc, 6:4) and pure product 20 was isolated as a white solid in 88% yield (360 mg).

(c) 8-(3-((2-(4-(((S)-2-((S)-2-(((((9H-fluoren-9-yl) methoxy)carbonyl)amino)-3-methylbutanamido) propanamido)phenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (21)

Bis-triflate 12 (2.03 g, 1.81 mmol), boronic pinacol ester (1 g, 1.63 mmol) and $Na_2CO_3$ (881 mg, 8.31 mmol) were dissolved in a mixture of toluene/MeOH/$H_2O$, 2:1:1 (40 mL). The reaction flask was purged and filled with argon three times before tetrakis(triphenylphosphine)palladium(0) (41 mg, 0.035 mmol) was added and the reaction mixture heated to 30° C. overnight. The solvents were removed under reduce pressure and the residue was taken up in $H_2O$ (100 mL) and extracted with EtOAc (3×100 mL). The combined organics were washed with brine (100 mL), dried with $MgSO_4$, filtered and the volatiles removed by rotary evaporation under reduced pressure. The crude product was purified by silica gel chromatography column (Hexane/EtOAc, 8:2 to 25:75) to afford pure 21 in 33% yield (885 mg). LC/MS 3.85 min (ES+) m/z (relative intensity) 1452.90; $^1$H NMR (400 MHz, $CDCl_3$) δ 7.78-7.16 (m, 17H), 7.13 (s, 1H), 6.51-6.24 (m, 1H), 5.51 (dd, J=10.0, 5.1 Hz, 2H), 5.36-5.11 (m, 1H), 4.74 (dd, J=10.1, 4.4 Hz, 2H), 4.70-4.53 (m, 2H), 4.47 (d, J=6.4 Hz, 1H), 4.37 (d, J=7.2 Hz, 1H), 4.27 (m, 4H), 4.20-4.14 (m, 1H), 3.90 (s, 3H), 3.89 (s, 3H), 3.77 (ddd, J=16.7, 9.0, 6.4 Hz, 3H), 3.71-3.61 (m, 2H), 3.24-2.91 (m, 3H), 2.55-2.33 (m, 2H), 2.22-2.07 (m, 1H), 1.52-1.37 (m, 3H), 1.04-0.86 (m, 1 OH), 0.00 (s, 18H).

(d) (9H-fluoren-9-yl)methyl((2S)-1-(((2S)-1-((4-(8-(3-((2-cyclopropyl-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl) oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl)phenyl)amino)-1-oxopropan-2-yl)amino)-3-methyl-1-oxobutan-2-yl)carbamate (22)

Triphenylarsine (42 mg, 0.137 mmol) was added to a mixture of PBD-triflate 21 (250 mg, 0.172 mmol), cyclopropylboronic acid (73.9 mg, 0.86 mmol), silver oxide (159 mg, 0.688 mmol) and potassium phosphate tribasic (438 mg, 2.06 mmol) in dry dioxane (10 mL) under an argon atmosphere. The reaction was flushed with argon 3 times and bis(benzonitrile)palladium(II) chloride (13.2 mg, 0.034 mmol) was added. The reaction was flushed with Argon 3 more times before being warmed to 75° C. and stirred for 10 minutes. The reaction mixture was filtered through a pad of celite which was subsequently rinsed with ethyl acetate. The solvent was removed by rotary evaporation under reduced pressure. The resulting residue was subjected to flash column chromatography (silica gel; 1% methanol/chloroform). Pure fractions were collected and combined, and excess eluent was removed by rotary evaporation under reduced pressure to afford the desired product 22 (132 mg, 50% yield). LC/MS 3.83 min (ES+) m/z (relative intensity) 1345.91; $^1$H NMR (400 MHz, $CDCl_3$) δ 7.88-7.14 (m, 17H), 6.69 (s, 1H), 6.45-6.25 (m, 1H), 5.57-5.41 (m, 2H), 5.34-5.14 (m, 1H), 4.78-4.67 (m, 2H), 4.62-4.55 (m, 1H), 4.50-4.45 (m, 2H), 4.51-4.44 (m, 1H), 4.31-4.21 (m, 4H), 4.16 (m, 1H), 3.92 (s, 3H), 3.86 (s 3H), 3.82-3.71 (m, 2H), 3.66 (m, 3H), 3.40-3.28 (m, 1H), 3.07 (m, 1H), 2.70-2.57 (m, 1H), 2.47-2.36 (m, 2H), 2.15 (m, 1H), 1.51-1.40 (m, 3H), 1.03-0.87 (m, 11H), 0.77-0.71 (m, 2H), 0.60-0.54 (m, 2H), 0.00 (t, J=3.0 Hz, 18H).

(e) (9H-fluoren-9-yl)methyl((2S)-1-(((2S)-1-((4-(8-(3-((2-cyclopropyl-7-methoxy-5-oxo-5,11a-dihydro-1H-benzo[e]pyrrolo[1,2-a][1,4]diazepin-8-yl)oxy) propoxy)-7-methoxy-5-oxo-5,11a-dihydro-1H-benzo [e]pyrrolo[1,2-a][1,4]diazepin-2-yl)phenyl)amino)-1-oxopropan-2-yl)amino)-3-methyl-1-oxobutan-2-yl) carbamate (23)

A solution of Super-Hydride® (0.5 mL, 1M in THF) was added dropwise to a solution of SEM dilactam 22 (265 mg g, 0.19 mmol) in THF (10 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with $MgSO_4$, filtered and the solvent removed by rotary evaporation under reduced pressure. The crude product was dissolved in MeOH (12 mL), $CH_2Cl_2$ (6 mL), water (2 mL) and enough silica gel to form a thick stirring suspension. After 5 days, the suspension was filtered through a sintered funnel and washed with $CH_2Cl_2$/MeOH (9:1) (200 mL) until the elution of the product was complete. The organic layer was washed with brine (2×70 mL), dried with $MgSO_4$, filtered and the solvent removed by rotary evaporation under reduced pressure. Purification by silica gel column chromatography (100% $CHCl_3$ to 96% $CHCl_3$/4% MeOH) afforded the product 23 as a yellow solid (162 mg, 78%). LC/MS 3.02 min (ES+) m/z (relative intensity) 1052.37.

(f) (2S)-2-amino-N-((2S)-1-((4-(8-(3-((2-cyclopropyl-7-methoxy-5-oxo-5,11a-dihydro-1H-benzo[e] pyrrolo[1,2-a][1,4]diazepin-8-yl)oxy)propoxy)-7-methoxy-5-oxo-5,11a-dihydro-1H-benzo[e]pyrrolo [1,2-a][1,4]diazepin-2-yl)phenyl)amino)-1-oxopropan-2-yl)-3-methylbutanamide (17)

Excess piperidine was added (0.2 mL, 2 mmol) to a solution of SEM-dilactam 23 (76 mg, 0.073 mmol) in DMF (1 mL). The mixture was allowed to stir at room temperature for 20 min, at which point the reaction had gone to completion (as monitored by LC/MS). The reaction mixture was diluted with $CH_2Cl_2$ (75 mL) and the organic phase was washed with $H_2O$ (3×75 mL) until complete piperidine removal. The organic phase was dried over $MgSO_4$, filtered and excess solvent removed by rotary evaporation under reduced pressure to afford crude product 17 which was used as such in the next step. LC/MS 2.32 min (ES+) m/z (relative intensity) 830.00.

(g) N-((2S)-1-(((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-1-(3-(2,5-dioxo-2,5-dihydro-1H-pyrrol-1-yl)propanamido)-3,6,9,12,15,18,21,24-octaoxaheptacosan-27-amide (18)

EDCl hydrochloride (14 mg, 0.0732 mmol) was added to a suspension of Maleimide-PEG$_8$-acid (43.4 mg, 0.0732 mmol) in dry CH$_2$Cl$_2$ (5 mL) under argon atmosphere. The mixture was stirred for 1 hour at room temperature before PBD 17 (60.7 mg, 0.0732 mmol) was added. Stirring was maintained until the reaction was complete (usually 5 hours). The reaction was diluted with CH$_2$Cl$_2$ and the organic phase was washed with H$_2$O and brine before being dried over MgSO$_4$, filtered and excess solvent removed by rotary evaporation under reduced pressure by rotary evaporation under reduced pressure. The product was purified by careful silica gel chromatography (slow elution starting with 100% CHCl$_3$ up to 9:1 CHCl$_3$/MeOH) followed by reverse phase chromatography to remove unreacted maleimide-PEG$_8$-acid. The product 18 was isolated in 17.6% (21.8 mg). LC/MS 2.57 min (ES+) m/z (relative intensity) 1405.30; $^1$H NMR (400 MHz, CDCl$_3$) δ 7.91 (t, J=3.5 Hz, 1H), 7.80 (d, J=4.0 Hz, 1H), 7.75 (d, J=8.8 Hz, 1H), 7.69 (d, J=8.7 Hz, 1H), 7.54-7.50 (m, 2H), 7.45 (s, 1H), 7.39-7.31 (m, 2H), 6.87 (d, J=10.5 Hz, 2H), 6.76 (s, 1H), 6.72-6.68 (m, 2H), 4.74-4.62 (m, 1H), 4.45-4.17 (m, 7H), 3.95 (s, 3H), 3.94 (s, 3H), 3.67-3.58 (m, 34H), 3.54 (m, 2H), 3.42 (dd, J=10.2, 5.2 Hz, 2H), 3.16-3.07 (m, 1H), 2.92 (dd, J=16.1, 4.1 Hz, 1H), 2.62-2.49 (m, 4H), 2.48-2.39 (m, 2H), 2.37-2.25 (m, 1H), 1.92 (s, 1H), 1.52-1.44 (m, 3H), 1.10-0.93 (m, 6H), 0.79 (dd, J=9.2, 5.3 Hz, 2H), 0.57 (dd, J=9.2, 5.3 Hz, 2H), NH were not observed.

Example 3

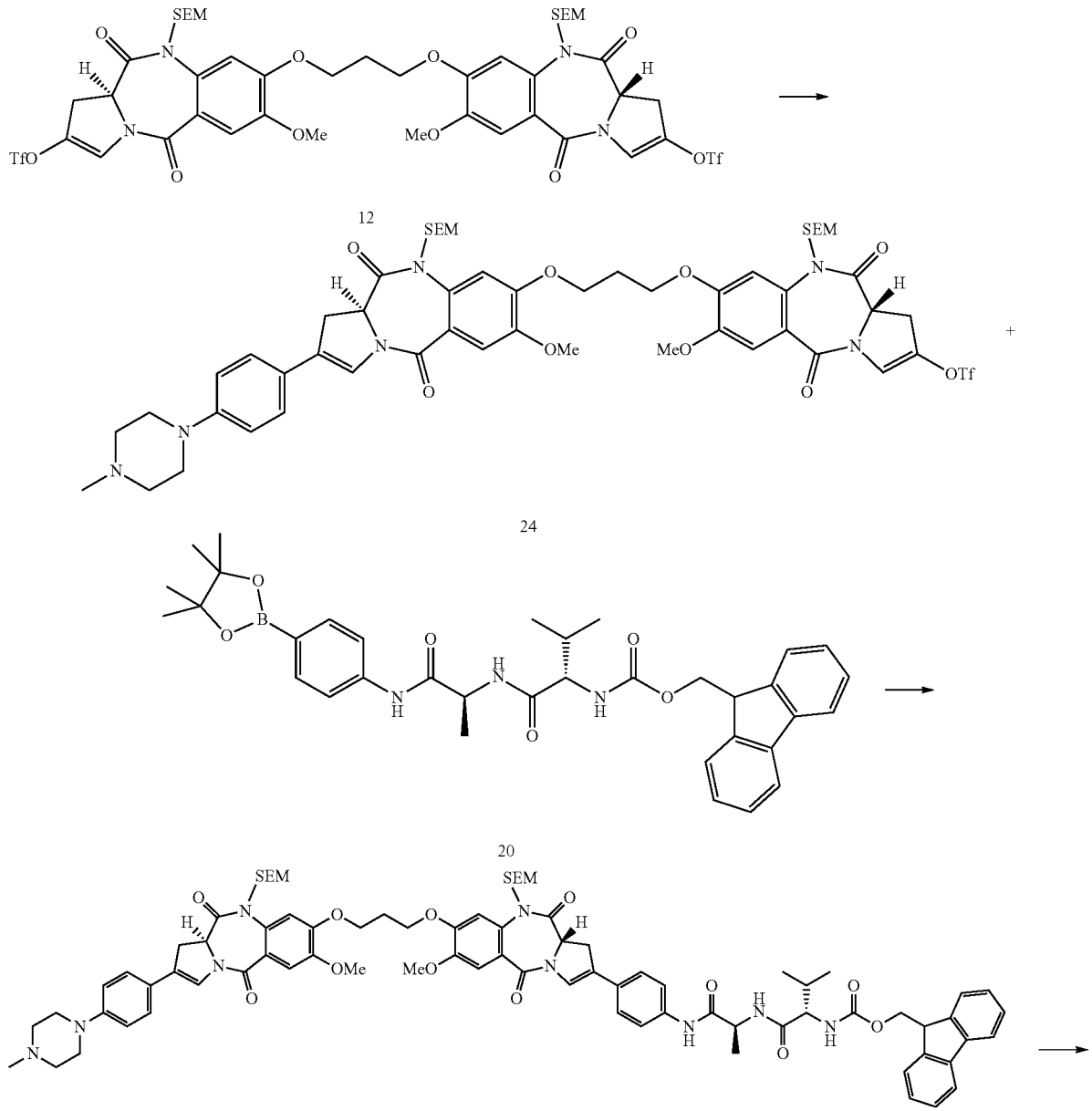

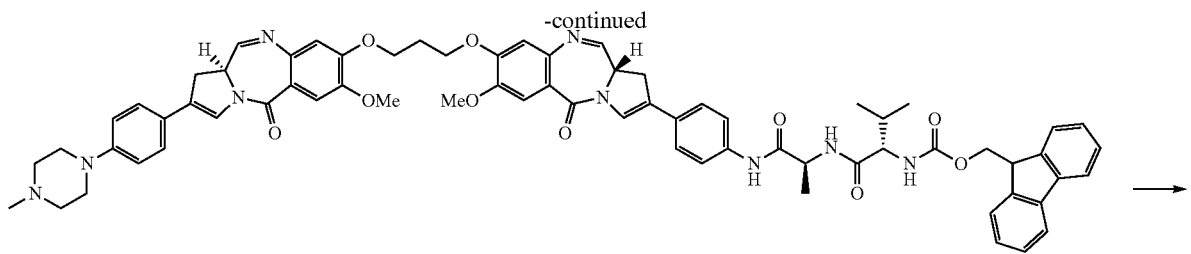

26

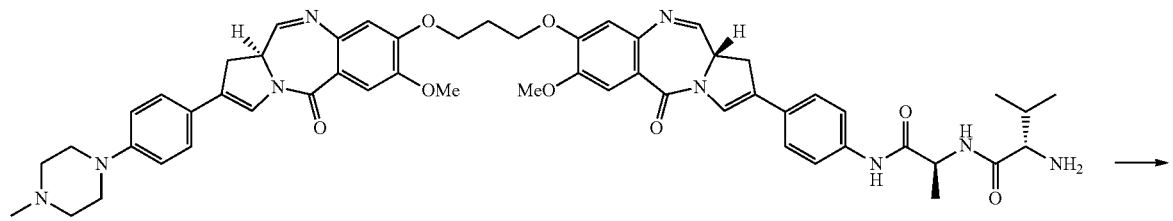

27

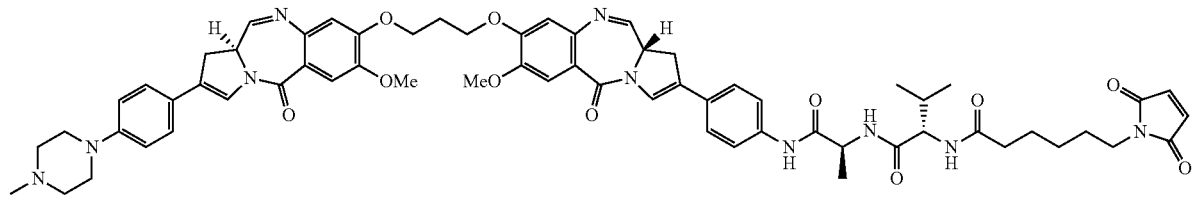

28

(a) (S)-7-methoxy-8-(3-(((S-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propyl)-5,11-dioxo-10-((2-trimethylsilyl)ethoxy)methyl)-5,10,11,11a-tetrahydro-1H-pyrrolo[2,1-c][1,4]benzodiazepin-2-yl trifluormethanesulfonate (24)

Pd(PPh$_3$)$_4$ (20.6 mg, 0.018 mmol) was added to a stirred mixture of the bis-enol triflate 12 (500 mg, 0.44 mmol), N-methyl piperazine boronic ester (100 mg, 0.4 mmol), Na$_2$CO$_3$ (218 mg, 2.05 mmol), MeOH (2.5 mL), toluene (5 mL) and water (2.5 mL). The reaction mixture was allowed to stir at 30° C. under a nitrogen atmosphere for 24 hours after which time all the boronic ester has consumed. The reaction mixture was then evaporated to dryness before the residue was taken up in EtOAc (100 mL) and washed with H$_2$O (2×50 mL), brine (50 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 24 as a yellowish foam (122.6 mg, 25%). LC/MS 3.15 min (ES+) m/z (relative intensity) 1144 ([M+H]$^{+•}$, 20%).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-0-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (25)

PBD-triflate 24 (359 mg, 0.314 mmol), boronic pinacol ester 20 (250 mg, 0.408 mmol) and triethylamine (0.35 mL, 2.51 mmol) were dissolved in a mixture of toluene/MeOH/H$_2$O, 2:1:1 (3 mL). The microwave vessel was purged and filled with argon three times before tetrakis(triphenylphosphine)palladium(0) (21.7 mg, 0.018 mmol) was added and the reaction mixture placed in the microwave at 80° C. for 10 minutes. Subsequently, CH$_2$Cl$_2$ (100 mL) was added and the organics were washed with water (2×50 mL) and brine (50 mL) before being dried with MgSO$_4$, filtered and the volatiles removed by rotary evaporation under reduced pressure. The crude product was purified by silica gel chromatography column (CHCl$_3$/MeOH, 100% to 9:1) to afford pure 25 (200 mg, 43% yield). LC/MS 3.27 min (ES+) m/z (relative intensity) 1478 ([M+H]$^{+•}$, 100%).

(c) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl) carbamate (26)

A solution of Super-Hydride® (0.34 mL, 1M in THF) was added dropwise to a solution of SEM-dilactam 25 (200 mg, 0.135 mmol) in THF (5 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with MgSO$_4$, filtered and the solvent removed by rotary evaporation under reduced pressure. The crude product was dissolved in MeOH (6 mL), CH$_2$Cl$_2$ (3 mL), water (1 mL) and enough silica gel to form a thick stirring suspension. After 5 days, the suspension was filtered through a sintered funnel and washed with CH$_2$Cl$_2$/MeOH (9:1) (100 mL) until the elution of the product was complete. The organic layer was washed with brine (2×50 mL), dried with MgSO$_4$, filtered and the solvent removed by rotary evaporation under reduced pressure. Purification by silica gel column chromatography (100% CHCl$_3$ to 96% CHCl$_3$/4% MeOH) afforded the product 26 as a yellow solid (100 mg, 63%). LC/MS 2.67 min (ES+) m/z (relative intensity) 1186 ([M+H]$^{+•}$, 5%).

(d) (S)-2-amino-N—((S)-1-((4-((R)-7-methoxy-8-(3-(((R)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (27)

Excess piperidine was added (0.1 mL, 1 mmol) to a solution of PBD 26 (36.4 mg, 0.03 mmol) in DMF (0.9 mL). The mixture was allowed to stir at room temperature for 20 min, at which point the reaction had gone to completion (as monitored by LC/MS). The reaction mixture was diluted with CH$_2$Cl$_2$ (50 mL) and the organic phase was washed with H$_2$O (3×50 mL) until complete piperidine removal. The organic phase was dried over MgSO$_4$, filtered and excess solvent removed by rotary evaporation under reduced pressure to afford crude product 27 which was used as such in the next step. LC/MS 2.20 min (ES+) m/z (relative intensity) 964 ([M+H]$^{+•}$, 5%).

(e) 6-(2,5-dioxo-2,5-dihydro-1H-pyrrol-1-yl)-N—((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (28)

EDCl hydrochloride (4.7 mg, 0.03 mmol) was added to a suspension of 6-maleimidohexanoic acid (6.5 mg, 0.03 mmol) in dry CH$_2$Cl$_2$ (3 mL) under argon atmosphere. The mixture was stirred for 1 hour at room temperature before PBD 27 (34 mg, crude) was added. Stirring was maintained until the reaction was complete (6 hours). The reaction was diluted with CH$_2$Cl$_2$ and the organic phase was washed with H$_2$O and brine before being dried over MgSO$_4$, filtered and excess solvent removed by rotary evaporation under reduced pressure by rotary evaporation under reduced pressure. The product was purified by careful silica gel chromatography (slow elution starting with 100% CHCl$_3$ up to 9:1 CHCl$_3$/MeOH) followed by reverse phase chromatography to remove unreacted maleimide-PEG$_8$-acid. The product 28 was isolated in 41% over two steps (14.6 mg). LC/MS 2.40 min (ES+) m/z (relative intensity) 1157 ([M+H]$^{+•}$, 5%)

Example 4—Alternative Synthesis of Compound 25

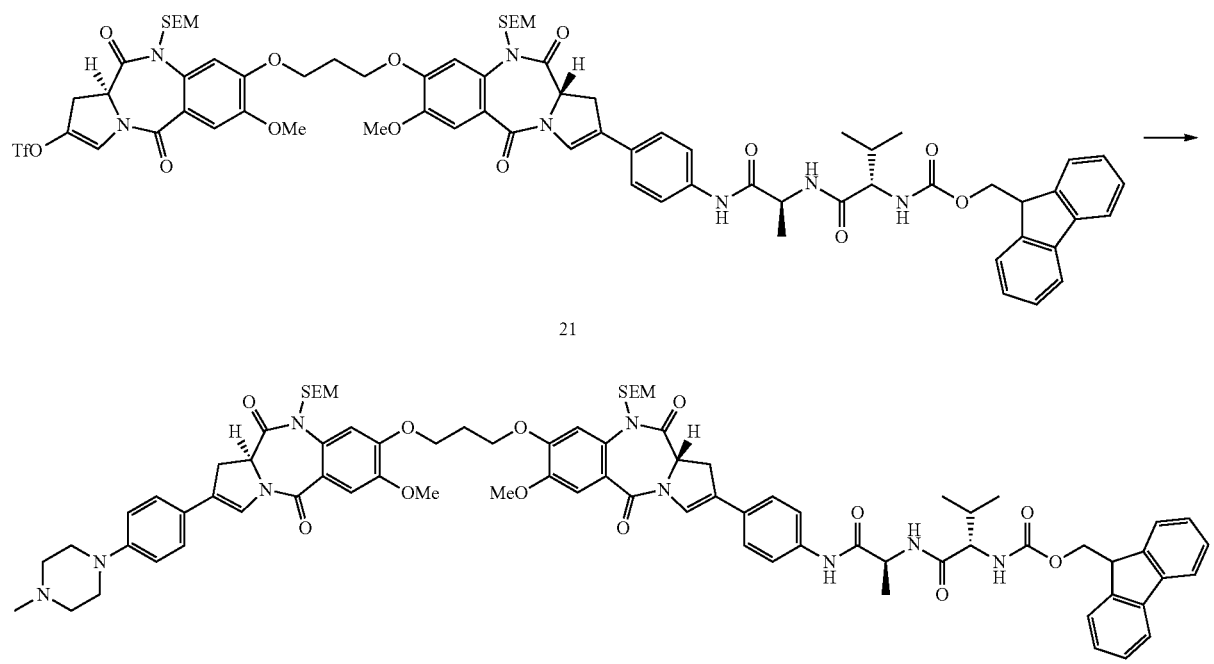

PBD-triflate 21 (469 mg, 0.323 mmol), boronic pinacol ester (146.5 mg, 0.484 mmol) and Na$_2$CO$_3$ (157 mg, 1.48 mmol) were dissolved in a mixture of toluene/MeOH/H$_2$O, 2:1:1 (10 mL). The reaction flask was purged with argon three times before tetrakis(triphenylphosphine)palladium(0) (7.41 mg, 0.0064 mmol) was added and the reaction mixture heated to 30° C. overnight. The solvents were removed under reduced pressure and the residue was taken up in H$_2$O (50 mL) and extracted with EtOAc (3×50 mL). The combined organics were washed with brine (100 mL), dried with MgSO$_4$, filtered and the volatiles removed by rotary evaporation under reduced pressure. The crude product was purified by silica gel column chromatography (CHCl$_3$ 100% to CHCl$_3$/MeOH 95%:5%) to afford pure 25 in 33% yield (885 mg). LC/MS 3.27 min (ES+) m/z (relative intensity) 1478 ([M+H]$^{+\bullet}$, 100%).

Example 5

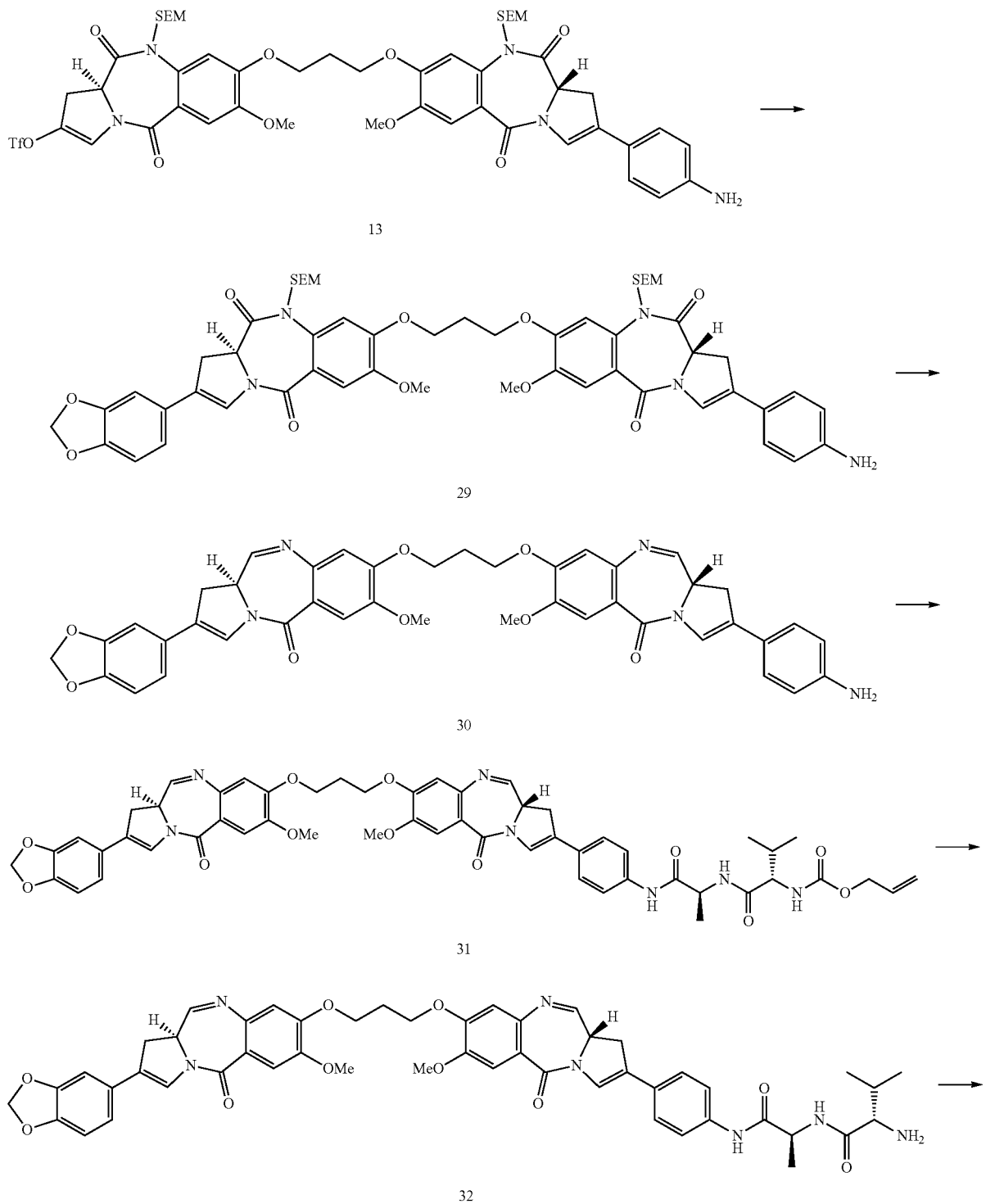

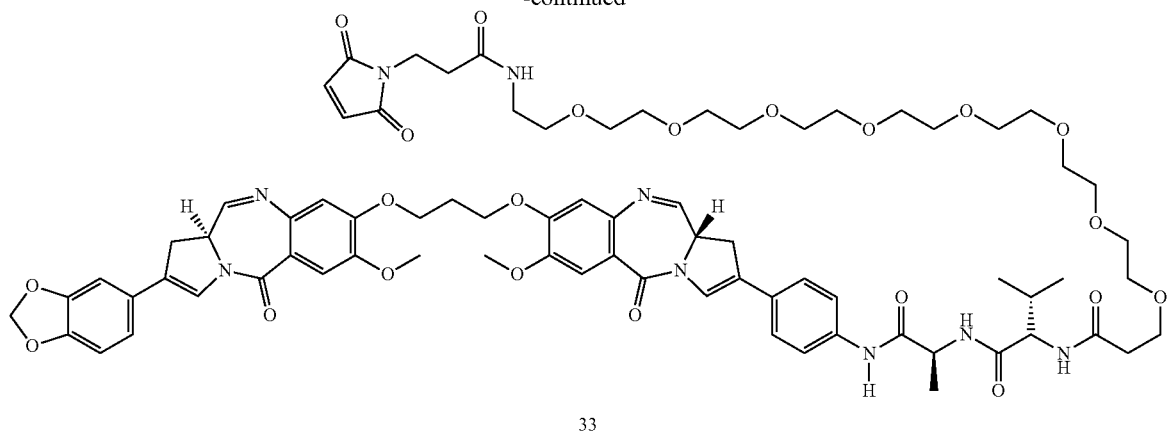

33

(a) (S)-2-(4-Aminophenyl)-8-(3-(((S)-2-(benzo[d][1,3]dioxol-5-yl)-7-methoxy-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-7-methoxy-10-((2-(trimethylsilyl)ethoxy)methyl)-1H-pyrrolo[2,1-c][1,4]benzodiazepine-5,11(10H,11aH)-dione (29)

3,4-(Methylenedioxy)phenyl boronic acid (356 mg, 2.1 mmol, 1.3 equiv.), TEA (1.8 mL, 12.9 mmol, 8 equiv.) and triflate/aniline 13 (1.75 g, 1.7 mmol, 1 equiv.) were dissolved in a mixture of ethanol (7 mL), toluene (13 mL) and water (2 mL) under an Ar atmosphere. The reaction mixture was evacuated and flushed with Ar 3 times, before addition of tetrakis(triphenylphosphine)palladium(0) (114 mg, 0.1 mmol, 0.06 equiv.). The flask was again evacuated and flushed with Ar 3 times and heated in a microwave at 80° C. for 8 minutes with 30 seconds pre-stirring time. Analysis by TLC (80:20 v/v ethyl acetate/hexane) indicated complete consumption of starting material. The reaction mixture was diluted with dichloromethane (50 mL) and washed with water (50 mL). The organic layer was dried with $MgSO_4$, filtered and the solvent removed in vacuo. Purification by silica gel column chromatography (60:40 to 20:80 v/v hexane/ethyl acetate) afforded the product 29 as a yellow solid (1.21 g, 71%). LC/MS (3.92 min ($ES^+$) m/z (relative intensity) 1032.44 ([M+H]$^{+\bullet}$, 100).

(b) (S)-2-(4-Aminophenyl)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-1H-pyrrolo[2,1-c][1,4]benzodiazepin-5(11aH)-one (30)

SEM dilactam 29 (0.25 g, 0.24 mmol, 1 equiv.) was dissolved in THF (8 mL) and cooled to −78° C. under an Ar atmosphere. Super-Hydride® (0.6 mL, 1 M in THF, 2.5 equiv.) was added drop wise over 5 minutes while monitoring the temperature. After 20 minutes a small sample was taken and worked-up for LCMS analysis. Water (50 mL) was added, the cold bath was removed and the solution washed with ethyl acetate (50 mL). The organic layer was extracted and washed with brine (60 mL), dried with $MgSO_4$, filtered and the solvent removed in vacuo. The crude product was dissolved in EtOH (15 mL), $CH_2Cl_2$ (7.5 mL) and water (2.5 mL) and enough silica gel was added until it was a thick suspension. After 5 days stirring, it was filtered through a sintered funnel and washed with $CH_2Cl_2$/MeOH (9:1) (100 mL) until product ceased to be eluted. The organic layer was washed with brine (2×50 mL), dried with $MgSO_4$, filtered and the solvent removed in vacuo. Purification by silica gel column chromatography ($CHCl_3$ with 1% to 4% MeOH gradient) afforded the product 30 as a yellow solid (94 mg, 53%). LC/MS (2.53 min ($ES^+$) m/z (relative intensity) 739.64 ([M]$^{+\bullet}$, 70).

(c) Allyl ((S)-1-(((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (31)

Under an Ar atmosphere, Alanine-Valine-Alloc (180 mg, 0.66 mmol, 1.2 equiv.) was stirred with EEDQ (163 mg, 0.66 mmol, 1.2 equiv.) in anhydrous $CH_2Cl_2$ (21 mL) and methanol (1 mL) for 1 hour. The PBD 30 (407 mg, 0.55 mmol, 1 equiv.) was dissolved in anhydrous $CH_2Cl_2$ (21 mL) and methanol (1 mL) and added to the reaction. LC/MS after 5 days stirring at room temperature showed majority product formation. The solvent was removed in vacuo before purification by column chromatography ($CH_2Cl_2$ with 1% to 6% MeOH gradient) to yield the product 31 as a yellow solid (184 mg, 34%). LC/MS (2.95 min ($ES^+$) m/z (relative intensity) 994.95 ([M+H]$^{+\bullet}$, 60).

(d) (S)-2-Amino-N—((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)-3-methylbutanamide (32)

The imine 31 (100 mg, 0.1 mmol, 1 equiv.) was dissolved in anhydrous DCM (10 mL) (with the aid of one drop of methanol to aid dissolution) under an Ar atmosphere. Pyrrolidine (30 µL, 0.15 mmol, 1.5 equiv.) was added drop wise before the flask was evacuated and flushed with Ar three times. Pd(PPh$_3$)$_4$ (7 mg, 6 µmol, 0.06 equiv.) was added and the flask was evacuated and flushed with Ar three times. LC/MS analysis after 1 hour indicated product formation and complete loss of starting material. Et$_2$O (60 mL) was added to the reaction mixture and it was left to stir until all the product had crashed out of solution. The precipitate was filtered through a sintered funnel and washed twice with Et$_2$O (2×20 mL). The collection flask was replaced and the isolated solid was dissolved and washed through the sinter with CHCl$_3$ (100 mL). The solvent was removed in vacuo to afford the crude product 32 as a yellow solid which was used directly in the next step. LC/MS (1.14 min (ES⁺) m/z (relative intensity) 910.40 ([M+H]⁺˙, 67).

(e) N—((S)-1-(((S)-1-((4-((S)-8-(3-(((S)-2-(Benzo [d][1,3]dioxol-5-yl)-7-methoxy-5-oxo-5,11a-dihydro-1H-pyrrolo[2,1-c][1,4]benzodiazepin-8-yl) oxy)propoxy)-7-methoxy-5-oxo-5,11a-dihydro-1H-pyrrolo[2,1-c][1,4]benzodiazepin-2-yl)phenyl) amino)-1-oxopropan-2-yl)amino)-3-methyl-1-oxobutan-2-yl)-1-(3-(2,5-dioxo-2,5-dihydro-1H-pyrrol-1-yl)propanamido)-3,6,9,12,15,18,21,24-octaoxaheptacosan-27-amide (33)

The imine 32 (92 mg, 0.1 mmol, 1.1 equiv.) was dissolved in CHCl₃ (6 mL) with one drop of anhydrous MeOH to aid dissolution. Maleimide-PEG₈-acid (53 mg, 0.09 mmol, 1 equiv.) was added followed by EEDQ (33 mg, 0.14 mmol, 1.5 equiv.). This was left to stir vigorously at room temperature under Ar for 4 days until LC/MS analysis showed majority product formation. The solvent was removed in vacuo and the crude product was partially purified by silica gel column chromatography (CHCl₃ with 1% to 10% MeOH gradient) yielding 33 (81 mg). The material was purified further by preparative HPLC to give 33 as a yellow solid (26.3 mg, 18%). Fast Formic run: LC/MS (1.39 min (ES+) m/z (relative intensity) 1485.00 ([M+H]⁺˙, 64).

Example 6

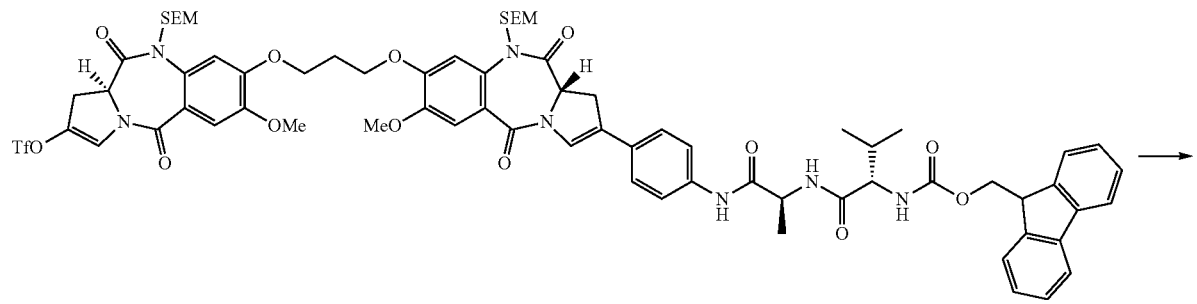

21

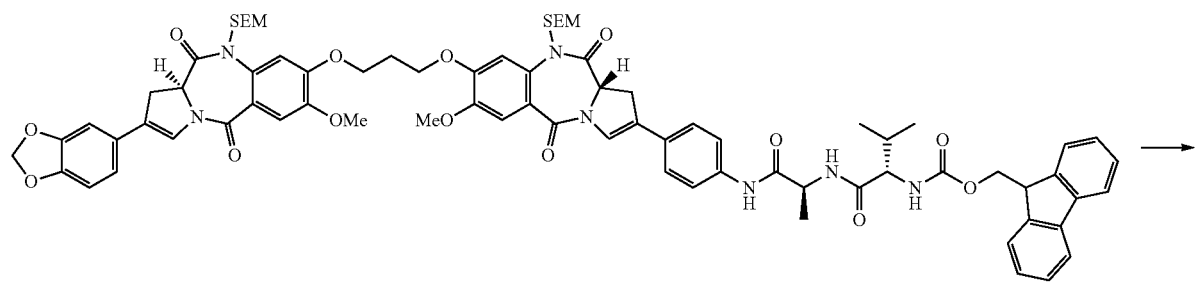

34

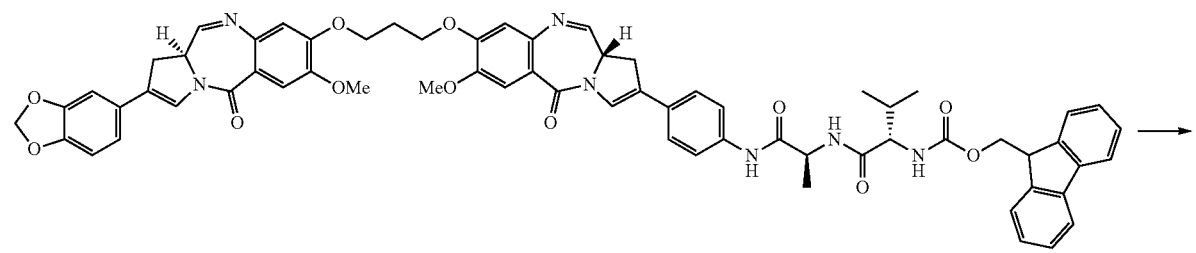

35

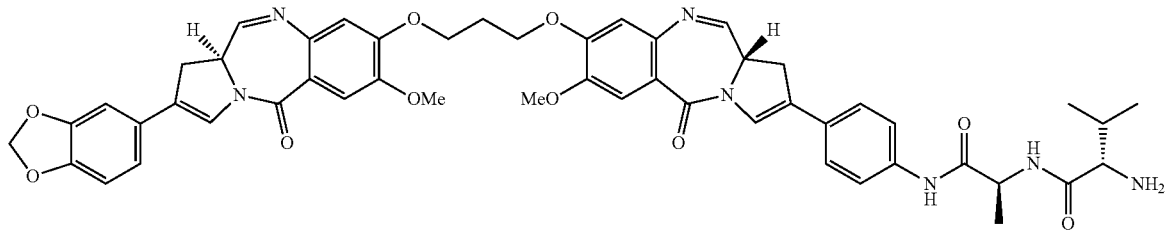

32

(a) 9H-Fluoren-9-yl) methyl ((S)-1-(((S)-1-((4-((S)-8-(3-(((S)-2-(benzo[d][1,3]dioxol-5-yl)-7-methoxy-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-7-methoxy-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (34)

The triflate 21 (0.5 g, 0.35 mmol, 1 equiv.), 3,4-(methylenedioxy)phenyl boronic acid (75 mg, 0.45 mmol, 1.3 equiv.) and Na$_2$CO$_3$ (0.17 g, 1.6 mmol, 4.5 equiv.) were dissolved in toluene (11 mL), EtOH (5.5 mL) and water (5.5 mL) under an Ar atmosphere. The flask was evacuated and flushed with Ar three times. Pd(PPh$_3$)$_4$ (24 mg, 0.02 mmol, 0.06 equiv.) was added and again the flask was evacuated and flushed with Ar three times. This was heated to 30° C. and left stirring overnight. Analysis by LC/MS showed complete loss of starting material. The solvent was removed in vacuo and the residue dissolved in water (60 mL) before washing with ethyl acetate (60 mL×3). The combined organic layers were washed with brine (50 mL), dried with MgSO$_4$, filtered and the solvent removed in vacuo. Purification by column chromatography (50:50 to 25:75 v/v hexane/ethyl acetate) afforded the product 34 as a yellow solid (310 mg, 64%). LC/MS (1.44 min (ES$^-$) m/z (relative intensity) 1423.35 ([M−H]$^{-\bullet}$, 79).

(b) (9H-Fluoren-9-yl)methyl ((S)-1-(((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (35)

SEM dilactam 34 (0.31 g, 0.22 mmol, 1 equiv.) was dissolved in THF (10 mL) and cooled to −78° C. under an Ar atmosphere. Super-Hydride® (0.5 mL, 1 M in THF, 2.5 equiv.) was added drop wise over 5 minutes while monitoring the temperature. After 30 minutes a small sample was taken and worked-up for LC/MS analysis. Water (50 mL) was added, the cold bath was removed and the solution washed with ethyl acetate (50 mL). The organic layer was extracted and washed with brine (60 mL), dried with MgSO$_4$, filtered and the solvent removed in vacuo. The crude product was dissolved in EtOH (13.2 mL), CH$_2$Cl$_2$ (6.6 mL) and water (2.2 mL) and enough silica gel was added until it was a thick suspension. After 5 days stirring, it was filtered through a sintered funnel and washed with CH$_2$Cl$_2$/MeOH (9:1) (100 mL) until product ceased to be eluted. The organic layer was washed with brine (2×50 mL), dried with MgSO$_4$, filtered and the solvent removed in vacuo. Purification by silica gel column chromatography (CHCl$_3$ with 1% to 4% MeOH gradient) afforded the pure product 35 as a yellow solid (185 mg, 75%). LC/MS (1.70 min (ES$^+$) m/z (relative intensity) 1132.85 ([M+H]$^{+\bullet}$, 60).

(c) (S)-2-Amino-N—((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)-3-methylbutanamide (32)

The imine 35 (82 mg, 0.07 mmol, 1 equiv.) was dissolved in DMF (1 mL) before piperidine (0.2 mL, 2 mmol, excess) was added slowly. This solution was left to stir at room temperature for 20 minutes until LC/MS analysis showed complete consumption of starting material. The reaction mixture was diluted with CH$_2$Cl$_2$ (50 mL), washed with water (50 mL×4), dried with MgSO$_4$, filtered and the solvent removed in vacuo. The product 33 was used without further purification in the next step. LC/MS (1.15 min (ES$^+$) m/z (relative intensity) 910.60 ([M+H]$^{+\bullet}$, 58).

Example 7

(i) (S)-(2-amino-5-methoxy-4-((triisopropylsilyl)oxy)phenyl) (2-(((tert-butyldimethylsilyl)oxy)methyl)-4-methyl-2,3-dihydro-1H-pyrrol-1-yl)methanone (49)

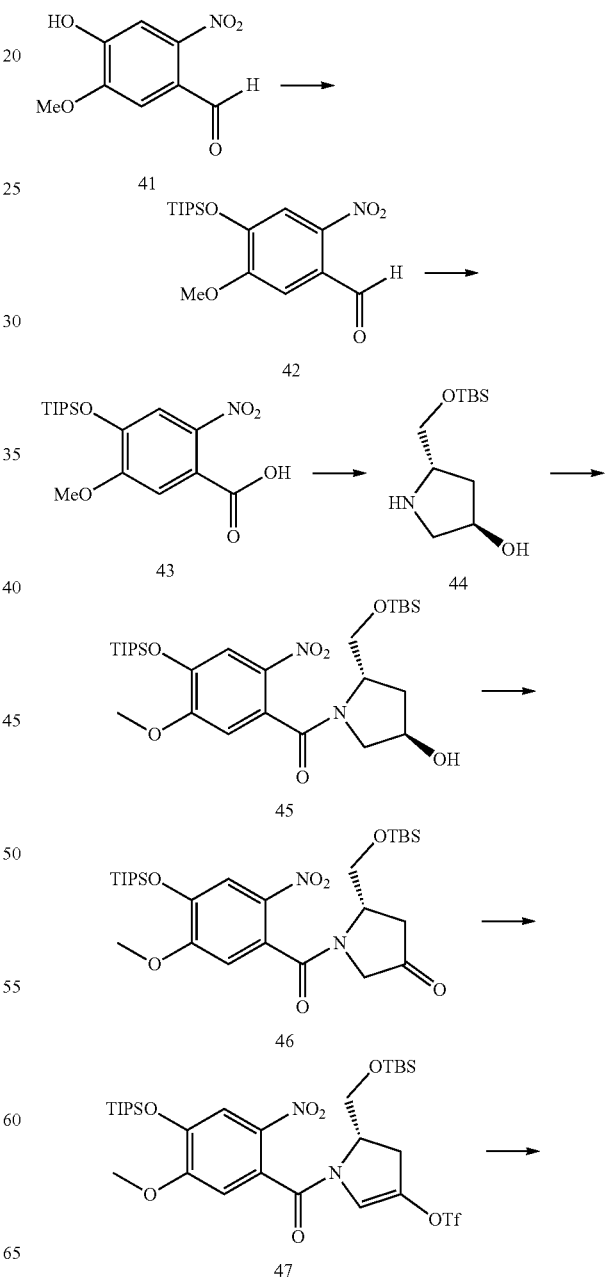

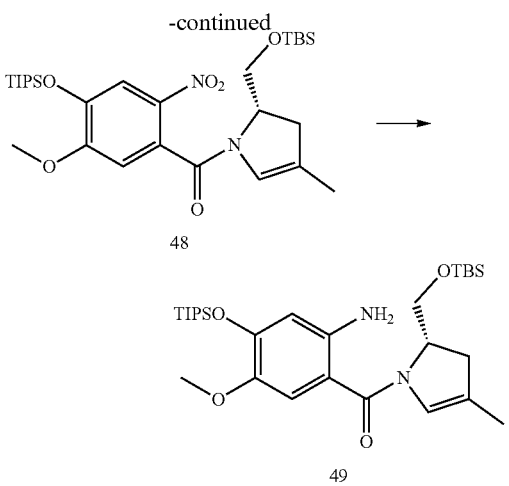

48

49

(a) 5-methoxy-2-nitro-4-((triisopropylsilyl)oxy)benzaldehyde (42)

Neat triisopropylsilylchloride (56.4 mL, 262 mmol) was added to a mixture of imidazole (48.7 g, 715.23 mmol) and 4-hydroxy-5-methoxy-2-nitrobenzaldehyde 41 (47 g, 238 mmol) (ground together). The mixture was heated until the phenol and imidazole melted and went into solution (100° C.). The reaction mixture was allowed to stir for 15 minutes and was then allowed to cool, whereupon a solid was observed to form at the bottom of the flask (imidazole chloride). The reaction mixture was diluted with 5% EtOAc/hexanes and loaded directly onto silica gel and the pad was eluted with 5% EtOAc/hexanes, followed by 10% EtOAc/hexanes (due to the low excess, very little unreacted TIPSCl was found in the product). The desired product was eluted with 5% ethyl acetate in hexane. Excess eluent was removed by rotary evaporation under reduced pressure, followed by drying under high vacuum to afford a crystalline light sensitive solid (74.4 g, 88%). Purity satisfactory by LC/MS (4.22 min (ES+) m/z (relative intensity) 353.88 ([M+H]$^{+•}$, 100)); $^1$H NMR (400 MHz, CDCl$_3$) δ 10.43 (s, 1H), 7.60 (s, 1H), 7.40 (s, 1H), 3.96 (s, 3H), 1.35-1.24 (m, 3H), 1.10 (m, 18H).

(b) 5-methoxy-2-nitro-4-((triisopropylsilyl)oxy)benzoic acid (43)

A solution of sodium chlorite (47.3 g, 523 mmol, 80% technical grade) and sodium dihydrogenphosphate monobasic (35.2 g, 293 mmol) (NaH$_2$PO$_4$) in water (800 mL) was added to a solution of compound 2 (74 g, 209 mmol) in tetrahydrofuran (500 mL) at room temperature. Hydrogen peroxide (60% w/w, 140 mL, 2.93 mol) was immediately added to the vigorously stirred biphasic mixture. The reaction mixture evolved gas (oxygen), the starting material dissolved and the temperature of the reaction mixture rose to 45° C. After 30 minutes LC/MS revealed that the reaction was complete. The reaction mixture was cooled in an ice bath and hydrochloric acid (1 M) was added to lower the pH to 3 (this step was found unnecessary in many instances, as the pH at the end of the reaction is already acidic; please check the pH before extraction). The reaction mixture was then extracted with ethyl acetate (1 L) and the organic phases washed with brine (2×100 mL) and dried over magnesium sulphate. The organic phase was filtered and excess solvent removed by rotary evaporation under reduced pressure to afford the product 43 in quantitative yield as a yellow solid. LC/MS (3.93 min (ES−) m/z (relative intensity) 367.74 ([M−H]$^{−•}$, 100)); $^1$H NMR (400 MHz, CDCl$_3$) δ 7.36 (s, 1H), 7.24 (s, 1H), 3.93 (s, 3H), 1.34-1.22 (m, 3H), 1.10 (m, 18H).

(c) ((2S,4R)-2-(((tert-butyldimethylsilyl)oxy)methyl)-4-hydroxypyrrolidin-1-yl) (5-methoxy-2-nitro-4-((triisopropylsilyl)oxy)phenyl)methanone (45)

DCC (29.2 g, 141 mmol, 1.2 eq) was added to a solution of acid 3 (43.5 g, 117.8 mmol, 1 eq), and hydroxybenzotriazole hydrate (19.8 g, 129.6 mmol, 1.1 eq) in dichloromethane (200 mL) at 0° C. The cold bath was removed and the reaction was allowed to proceed for 30 mins at room temperature, at which time a solution of (2S,4R)-2-t-butyldimethylsilyloxymethyl-4-hydroxypyrrolidine 44 (30 g, 129.6 mmol, 1.1 eq) and triethylamine (24.66 mL, 176 mmol, 1.5 eq) in dichloromethane (100 mL) was added rapidly at −10° C. under argon (on large scale, the addition time could be shortened by cooling the reaction mixture even further. The reaction mixture was allowed to stir at room temperature for 40 minutes to 1 hour and monitored by LC/MS and TLC (EtOAc). The solids were removed by filtration over celite and the organic phase was washed with cold aqueous 0.1 M HCl until the pH was measured at 4 or 5. The organic phase was then washed with water, followed by saturated aqueous sodium bicarbonate and brine. The organic layer was dried over magnesium sulphate, filtered and excess solvent removed by rotary evaporation under reduced pressure. The residue was subjected to column flash chromatography (silica gel; gradient 40/60 ethyl acetate/hexane to 80/20 ethyl acetate/hexane). Excess solvent was removed by rotary evaporation under reduced pressure afforded the pure product 45, (45.5 g of pure product 66%, and 17 g of slightly impure product, 90% in total). LC/MS 4.43 min (ES+) m/z (relative intensity) 582.92 ([M+H]$^{+•}$, 100); $^1$H NMR (400 MHz, CDCl$_3$) δ 7.66 (s, 1H), 6.74 (s, 1H), 4.54 (s, 1H), 4.40 (s, 1H), 4.13 (s, 1H), 3.86 (s, 3H), 3.77 (d, J=9.2 Hz, 1H), 3.36 (dd, J=11.3, 4.5 Hz, 1H), 3.14-3.02 (m, 1H), 2.38-2.28 (m, 1H), 2.10 (ddd, J=13.3, 8.4, 2.2 Hz, 1H), 1.36-1.19 (m, 3H), 1.15-1.05 (m, 18H), 0.91 (s, 9H), 0.17-0.05 (m, 6H), (presence of rotamers).

(d) (S)-5-(((tert-butyldimethylsilyl)oxy)methyl)-1-(5-methoxy-2-nitro-4-((triisopropylsilyl)oxy)benzoyl)pyrrolidin-3-one (46)

TCCA (8.82 g, 40 mmol, 0.7 eq) was added to a stirred solution of 45 (31.7 g, 54 mmol, 1 eq) and TEMPO (0.85 g, 5.4 mmol, 0.1 eq) in dry dichloromethane (250 mL) at 0° C. The reaction mixture was vigorously stirred for 20 minutes, at which point TLC (50/50 ethyl acetate/hexane) revealed complete consumption of the starting material. The reaction mixture was filtered through celite and the filtrate washed with aqueous saturated sodium bicarbonate (100 mL), sodium thiosulphate (9 g in 300 mL), brine (100 mL) and dried over magnesium sulphate. Rotary evaporation under reduced pressure afforded product 46 in quantitative yield. LC/MS 4.52 min (ES+) m/z (relative intensity) 581.08 ([M+H]$^{+•}$, 100); $^1$H NMR (400 MHz, CDCl$_3$) δ 7.78-7.60 (m, 1H), 6.85-6.62 (m, 1H), 4.94 (dd, J=30.8, 7.8 Hz, 1H), 4.50-4.16 (m, 1H), 3.99-3.82 (m, 3H), 3.80-3.34 (m, 3H), 2.92-2.17 (m, 2H), 1.40-1.18 (m, 3H), 1.11 (t, J=6.2 Hz, 18H), 0.97-0.75 (m, 9H), 0.15--0.06 (m, 6H), (presence of rotamers).

(e) (S)-5-(((tert-butyldimethylsilyl)oxy)methyl)-1-(5-methoxy-2-nitro-4-((triisopropylsilyl)oxy)benzoyl)-4,5-dihydro-1H-pyrrol-3-yl trifluoromethanesulfonate (47)

Triflic anhydride (27.7 mL, 46.4 g, 165 mmol, 3 eq) was injected (temperature controlled) to a vigorously stirred suspension of ketone 46 (31.9 g, 55 mmol, 1 eq) in dry dichloromethane (900 mL) in the presence of 2,6-lutidine (25.6 mL, 23.5 g, 220 mmol, 4 eq, dried over sieves) at −50° C. (acetone/dry ice bath). The reaction mixture was allowed to stir for 1.5 hours when LC/MS, following a mini work-up (water/dichloromethane), revealed the reaction to be complete. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel; 10/90 v/v ethyl acetate/hexane), removal of excess eluent afforded the product 47 (37.6 g, 96%) LC/MS, method 2, 4.32 min (ES+) m/z (relative intensity) 712.89 ([M+H]$^{+\bullet}$, 100); $^1$H NMR (400 MHz, CDCl$_3$) δ 7.71 (s, 1H), 6.75 (s, 1H), 6.05 (d, J=1.8 Hz, 1H), 4.78 (dd, J=9.8, 5.5 Hz, 1H), 4.15-3.75 (m, 5H), 3.17 (ddd, J=16.2, 10.4, 2.3 Hz, 1H), 2.99 (ddd, J=16.3, 4.0, 1.6 Hz, 1H), 1.45-1.19 (m, 3H), 1.15-1.08 (m, 18H), 1.05 (s, 6H), 0.95-0.87 (m, 9H), 0.15-0.08 (m, 6H).

(f) (S)-(2-(((tert-butyldimethylsilyl)oxy)methyl)-4-methyl-2,3-dihydro-1H-pyrrol-1-yl)(5-methoxy-2-nitro-4-((triisopropylsilyl)oxy)phenyl)methanone (48)

Triphenylarsine (1.71 g, 5.60 mmol, 0.4 eq) was added to a mixture of triflate 47 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(III) chloride (540 mg, 1.40 mmol, 0.1 eq) was added. The reaction was flushed with argon 3 more times before being warmed instantaneously to 110° C. (the drysyn heating block was previously warmed to 110° C. prior addition of the flask). After 10 mins the reaction was cooled to room temperature and filtered through a pad celite. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 48 (4.5 g, 55%). LC/MS, 4.27 min (ES+) m/z (relative intensity) 579.18 ([M+H]$^{+\bullet}$, 100); $^1$H NMR (400 MHz, CDCl$_3$) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(g) (S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone (49)

Zinc powder (28 g, 430 mmol, 37 eq) was added to a solution of compound 48 (6.7 g, 11.58 mmol) in 5% formic acid in ethanol v/v (70 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 49 (5.1 g, 80%). LC/MS, 4.23 min (ES+) m/z (relative intensity) 550.21 ([M+H]$^{+\bullet}$, 100); $^1$H NMR (400 MHz, CDCl$_3$) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03--0.03 (m, J=6.2 Hz, 6H).

(ii) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate

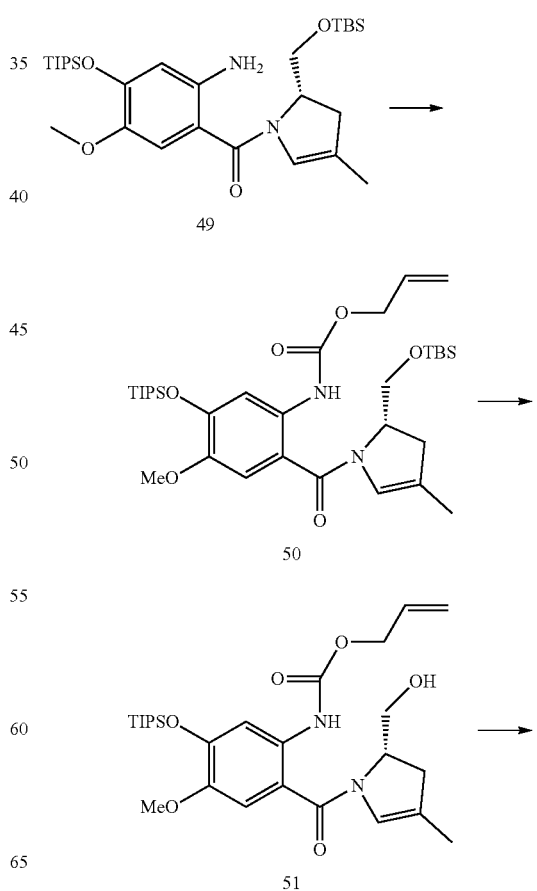

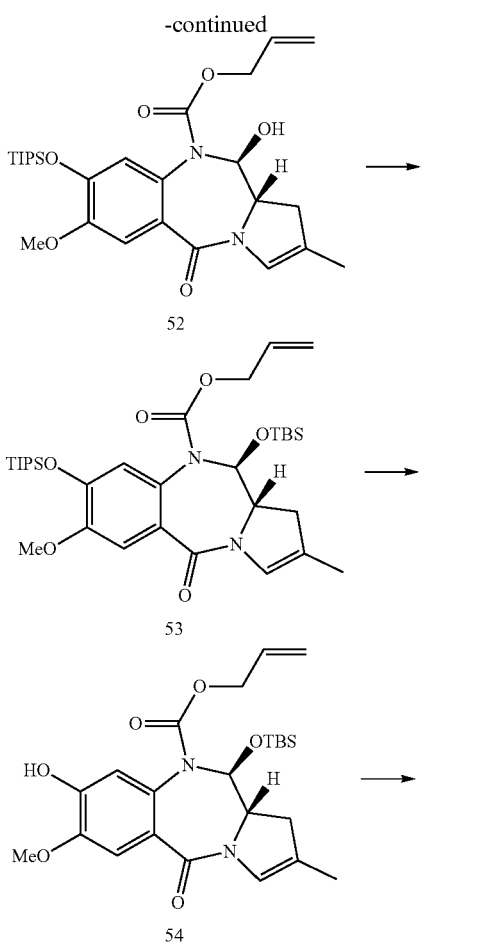

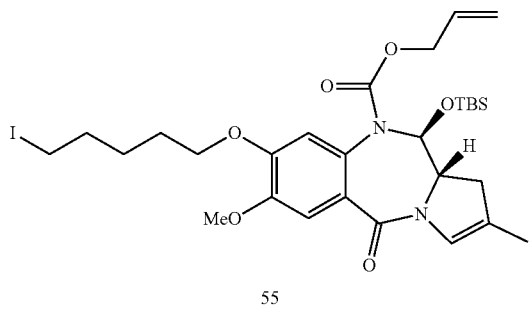

(a) (S)-allyl (2-(2-(((tert-butyldimethylsilyl)oxy)methyl)-4-methyl-2,3-dihydro-1H-pyrrole-1-carbonyl)-4-methoxy-5-((triisopropylsilyl)oxy)phenyl)carbamate (50)

Allyl chloroformate (0.30 mL, 3.00 mmol, 1.1 eq) was added to a solution of amine 49 (1.5 g, 2.73 mmol) in the presence of dry pyridine (0.48 mL, 6.00 mmol, 2.2 eq) in dry dichloromethane (20 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 50 which was used directly in the next reaction. LC/MS, 4.45 min (ES+) m/z (relative intensity) 632.91 ([M+H]$^{+•}$, 100)

(b) (S)-allyl (2-(2-(hydroxymethyl)-4-methyl-2,3-dihydro-1H-pyrrole-1-carbonyl)-4-methoxy-5-((triisopropylsilyl)oxy)phenyl)carbamate (51)

The crude 50 was dissolved in a 7:1:1:2 mixture of acetic acid/methanol/tetrahydrofuran/water (28:4:4:8 mL) and allowed to stir at room temperature. After 3 hours, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel, 25% ethyl acetate in hexane). Pure fractions were collected and combined and excess eluent was removed by rotary evaporation under reduced pressure to afford the desired product 51 (1 g, 71%). LC/MS, 3.70 min (ES+) m/z (relative intensity) 519.13 ([M+H]+, 95); $^1$H NMR (400 MHz, CDCl$_3$) δ 8.34 (s, 1H), 7.69 (s, 1H), 6.78 (s, 1H), 6.15 (s, 1H), 5.95 (ddt, J=17.2, 10.5, 5.7 Hz, 1H), 5.33 (dq, J=17.2, 1.5 Hz, 1H), 5.23 (ddd, J=10.4, 2.6, 1.3 Hz, 1H), 4.73 (tt, J=7.8, 4.8 Hz, 1H), 4.63 (dt, J=5.7, 1.4 Hz, 2H), 4.54 (s, 1H), 3.89-3.70 (m, 5H), 2.87 (dd, J=16.5, 10.5 Hz, 1H), 2.19 (dd, J=16.8, 4.6 Hz, 1H), 1.70 (d, J=1.3 Hz, 3H), 1.38-1.23 (m, 3H), 1.12 (s, 10H), 1.10 (s, 8H).

(c) (11S,11aS)-allyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (52)

Dimethyl sulphoxide (0.35 mL, 4.83 mmol, 2.5 eq) was added dropwise to a solution of oxalyl chloride (0.2 mL, 2.32 mmol, 1.2 eq) in dry dichloromethane (10 mL) at −78° C. (dry ice/acetone bath) under an atmosphere of argon. After 10 minutes a solution of 51 (1 g, 1.93 mmol) in dry dichloromethane (8 mL) was added slowly with the temperature still at −78° C. After 15 min triethylamine (1.35 mL, dried over 4 Å molecular sieves, 9.65 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 52 (658 mg, 66%). LC/MS, 3.52 min (ES+) m/z (relative intensity) 517.14 ([M+H]$^{+•}$, 100); $^1$H NMR (400 MHz, CDCl$_3$) δ 7.20 (s, 1H), 6.75-6.63 (m, J=8.8, 4.0 Hz, 2H), 5.89-5.64 (m, J=9.6, 4.1 Hz, 2H), 5.23-5.03 (m, 2H), 4.68-4.38 (m, 2H), 3.84 (s, 3H), 3.83-3.77 (m, 1H), 3.40 (s, 1H), 3.05-2.83 (m, 1H), 2.59 (d, J=17.1 Hz, 1H), 1.78 (d, J=1.3 Hz, 3H), 1.33-1.16 (m, 3H), 1.09 (d, J=2.2 Hz, 9H), 1.07 (d, J=2.1 Hz, 9H).

(d) (11S,11aS)-allyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (53)

Tert-butyldimethylsilyltriflate (0.70 mL, 3.00 mmol, 3 eq) was added to a solution of compound 52 (520 mg, 1.00 mmol) and 2,6-lutidine (0.46 mL, 4.00 mmol, 4 eq) in dry dichloromethane (40 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 53 (540 mg, 85%). LC/MS, 4.42 min (ES+) m/z (relative intensity) 653.14 ([M+Na]+•, 100); $^1$H NMR (400 MHz, CDCl$_3$) δ 7.20 (s, 1H), 6.71-6.64 (m, J=5.5 Hz, 2H), 5.83 (d, J=9.0 Hz, 1H), 5.80-5.68 (m, J=5.9 Hz, 1H), 5.14-5.06 (m, 2H), 4.58 (dd, J=13.2, 5.2 Hz, 1H), 4.36 (dd, J=13.3, 5.5 Hz, 1H), 3.84 (s, 3H), 3.71 (td, J=10.1, 3.8 Hz, 1H), 2.91 (dd, J=16.9, 10.3 Hz, 1H), 2.36 (d, J=16.8 Hz, 1H), 1.75 (s, 3H), 1.31-1.16 (m, 3H), 1.12-1.01 (m, J=7.4, 2.1 Hz, 18H), 0.89-0.81 (m, 9H), 0.25 (s, 3H), 0.19 (s, 3H).

(e) (11S,11aS)-allyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (54)

Lithium acetate (87 mg, 0.85 mmol) was added to a solution of compound 53 (540 mg, 0.85 mmol) in wet dimethylformamide (6 mL, 50:1 DMF/water). After 4 hours, the reaction was complete and the reaction mixture was diluted with ethyl acetate (25 mL) and washed with aqueous citric acid solution (pH 3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 54 (400 mg, quantitative). LC/MS, (3.33 min (ES+) m/z (relative intensity) 475.26 ([M+H]+, 100).

(f) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate (55)

Diiodopentane (0.63 mL, 4.21 mmol, 5 eq) and potassium carbonate (116 mg, 0.84 mmol, 1 eq) were added to a solution of phenol 54 (400 mg, 0.84 mmol) in acetone (4 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate). Pure fractions were collected and combined and excess eluent was removed to provide 55 in 90% yield. LC/MS, 3.901 min (ES+) m/z (relative intensity) 670.91 ([M]+, 100). $^1$H NMR (400 MHz, CDCl$_3$) δ 7.23 (s, 1H), 6.69 (s, 1H), 6.60 (s, 1H), 5.87 (d, J=8.8 Hz, 1H), 5.83-5.68 (m, J=5.6 Hz, 1H), 5.15-5.01 (m, 2H), 4.67-4.58 (m, 1H), 4.45-4.35 (m, 1H), 4.04-3.93 (m, 2H), 3.91 (s, 3H), 3.73 (td, J=10.0, 3.8 Hz, 1H), 3.25-3.14 (m, J=8.5, 7.0 Hz, 2H), 2.92 (dd, J=16.8, 10.3 Hz, 1H), 2.38 (d, J=16.8 Hz, 1H), 1.95-1.81 (m, 4H), 1.77 (s, 3H), 1.64-1.49 (m, 2H), 0.88 (s, 9H), 0.25 (s, 3H), 0.23 (s, 3H).

(iii) (11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (70)

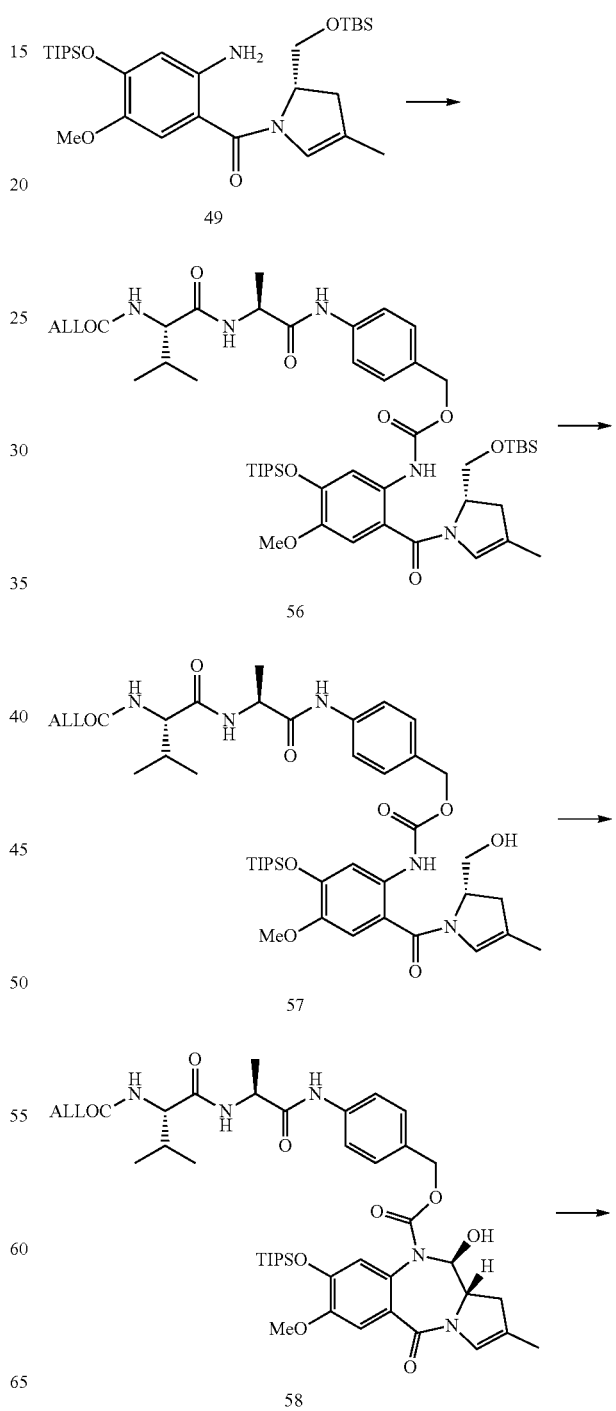

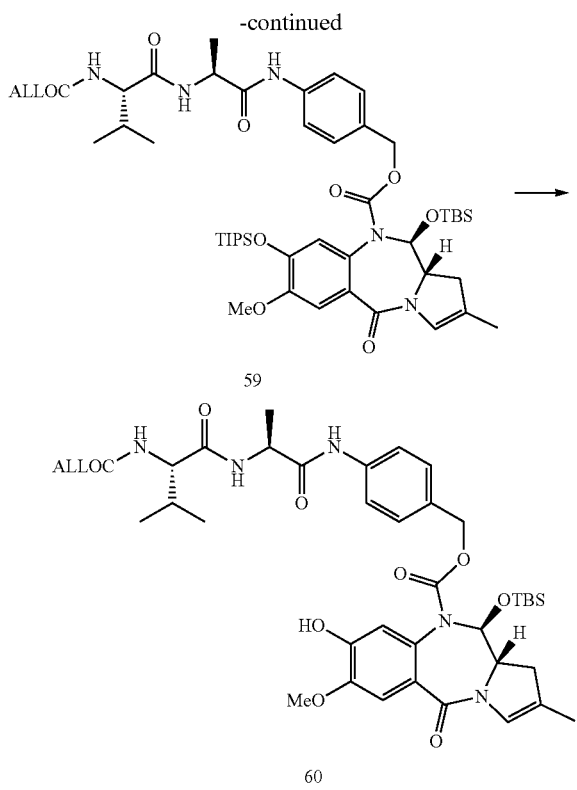

59

60

(a) Allyl 3-(2-(2-(4-(((((2-((S)-2-(((tert-butyldimethylsilyl)oxy)methyl)-4-methyl-2,3-dihydro-1H-pyrrole-1-carb on yl)-4-methoxy-5-((triisopropylsilyl)oxy)phenyl) carbamoyl)oxy)methyl)phenyl) hydrazinyl) propanamido)-4-methyl-2-oxopentanoate (56)

Triethylamine (2.23 mL, 18.04 mmol, 2.2 eq) was added to a stirred solution of the amine 49 (4 g, 8.20 mmol) and triphosgene (778 mg, 2.95 mmol, 0.36 eq) in dry tetrahydrofuran (40 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (4.12 g, 12.30 mmol, 1.5 eq) and triethylamine (1.52 mL, 12.30 mmol, 1.5 eq) in dry tetrahydrofuran (40 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 56 (3.9 g, 50%). LC/MS, 4.23 min (ES+) m/z (relative intensity) 952.36 ([M+H]$^{+\omega}$, 100); $^1$H NMR (400 MHz, CDCl$_3$) δ 8.62 (br s, 1H), 8.46 (s, 1-H), 7.77 (br s, 1H), 7.53 (d, J=8.4 Hz, 2H), 7.32 (d, J=8.5 Hz, 2H), 6.76 (s, 1H), 6.57 (d, J=7.6 Hz, 1H), 6.17 (s, 1H), 6.03-5.83 (m, 1H), 5.26 (dd, J=33.8, 13.5 Hz, 3H), 5.10 (s, 2H), 4.70-4.60 (m, 2H), 4.58 (dd, J=5.7, 1.3 Hz, 2H), 4.06-3.99 (m, 1H), 3.92 (s, 1H), 3.82-3.71 (m, 1H), 3.75 (s, 3H), 2.79-2.64 (m, 1H), 2.54 (d, J=12.9 Hz, 1H), 2.16 (dq, J=13.5, 6.7 Hz, 1H), 1.67 (s, 3H), 1.46 (d, J=7.0 Hz, 3H), 1.35-1.24 (m, 3H), 1.12 (s, 9H), 1.10 (s, 9H), 0.97 (d, J=6.8 Hz, 3H), 0.94 (d, J=6.8 Hz, 3H), 0.87 (s, 9H), 0.07--0.02 (m, 6H).

(b) Allyl 3-(2-(2-(4-(((((2-((S)-2-(hydroxymethyl)-4-methyl-2,3-dihydro-1H-pyrrole-1-carbonyl)-4-methoxy-5-((triisopropylsilyl)oxy)phenyl)carbamoyl)oxy)methyl)phenyl)hydrazinyl) propanamido)-4-methyl-2-oxopentanoate (57)

The TBS ether 56 (1.32 g, 1.38 mmol) was dissolved in a 7:1:1:2 mixture of acetic acid/methanol/tetrahydrofuran/water (14:2:2:4 mL) and allowed to stir at room temperature. After 3 hours no more starting material was observed by LC/MS. The reaction mixture was diluted with ethyl acetate (25 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol in dichloromethane). Pure fractions were collected and combined and excess eluent was removed by rotary evaporation under reduced pressure to afford the desired product 57 (920 mg, 80%). LC/MS, 3.60 min (ES+) m/z (relative intensity) 838.18 ([M+H]$^{+\ast}$, 100). $^1$H NMR (400 MHz, CDCl$_3$) δ 8.55 (s, 1H), 8.35 (s, 1H), 7.68 (s, 1H), 7.52 (d, J=8.1 Hz, 2H), 7.31 (d, J=8.4 Hz, 2H), 6.77 (s, 1H), 6.71 (d, J=7.5 Hz, 1H), 6.13 (s, 1H), 5.97-5.82 (m, J=5.7 Hz, 1H), 5.41-5.15 (m, 3H), 5.10 (d, J=3.5 Hz, 2H), 4.76-4.42 (m, 5H), 4.03 (t, J=6.6 Hz, 1H), 3.77 (s, 5H), 2.84 (dd, J=16.7, 10.4 Hz, 1H), 2.26-2.08 (m, 2H), 1.68 (s, 3H), 1.44 (d, J=7.0 Hz, 3H), 1.30 (dt, J=14.7, 7.4 Hz, 3H), 1.12 (s, 9H), 1.10 (s, 9H), 0.96 (d, J=6.8 Hz, 3H), 0.93 (d, J=6.8 Hz, 3H).

(c) (11S,11aS)-4-(2-(1-((1-(allyloxy)-4-methyl-1,2-dioxopentan-3-yl)amino)-1-oxopropan-2-yl)hydrazinyl)benzyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (58)

Dimethyl sulphoxide (0.2 mL, 2.75 mmol, 2.5 eq) was added dropwise to a solution of oxalyl chloride (0.11 mL, 1.32 mmol, 1.2 eq) in dry dichloromethane (7 mL) at −78° C. (dry ice/acetone bath) under an atmosphere of argon. After 10 minutes a solution of 57 (920 mg, 1.10 mmol) in dry dichloromethane (5 mL) was added slowly with the temperature still at -78° C. After 15 min triethylamine (0.77 mL, dried over 4 Å molecular sieves, 5.50 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 2% methanol to 5% methanol in dichloromethane). Pure fractions were collected and combined and removal of excess eluent by rotary evaporation under reduced pressure afforded the product 58 (550 mg, 60%). LC/MS, 3.43 min (ES+) m/z (relative intensity) 836.01 ([M]$^{+\ast}$, 100). $^1$H NMR (400 MHz, CDCl$_3$) δ 8.39 (s, 1H), 7.52-7.40 (min, 2H), 7.21-7.08 (m, J=11.5 Hz, 2H), 6.67 (s, 1H), 6.60-6.47 (m, J=7.4 Hz, 1H), 5.97-5.83 (m, 1H), 5.79-5.66 (m, 1H), 5.38-4.90 (m, 6H), 4.68-4.52 (m, J=18.4, 5.5 Hz, 4H), 4.04-3.94 (m, J=6.5 Hz, 1H), 3.87-3.76 (m, 5H), 3.00-2.88 (m, 1H), 2.66-2.49 (m, 2H), 2.21-2.08 (m, 2H), 1.76 (s, 3H), 1.45 (d, J=7.0 Hz, 3H), 1.09-0.98 (m, J=8.9 Hz, 18H), 0.96 (d, J=6.7 Hz, 3H), 0.93 (d, J=6.9 Hz, 3H).

(d) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (59)

Tert-butyldimethylsilyltriflate (0.38 mL, 1.62 mmol, 3 eq) was added to a solution of compound 58 (450 mg, 0.54 mmol) and 2,6-lutidine (0.25 mL, 2.16 mmol, 4 eq) in dry dichloromethane (5 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 59 (334 mg, 65%). LC/MS, 4.18 min (ES+) m/z (relative intensity) 950.50 ([M]$^{+\cdot}$, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(e) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (60)

Lithium acetate (50 mg, 0.49 mmol) was added to a solution of compound 59 (470 mg, 0.49 mmol) in wet dimethylformamide (4 mL, 50:1 DMF/water). After 4 hours, the reaction was complete and the reaction mixture was diluted with ethyl acetate and washed with citric acid (pH~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 25/75 v/v hexane/ethyl acetate). Pure fractions were collected and combined and excess eluent was removed by rotary evaporation under reduced pressure to give the product 60 (400 mg, quantitative). LC/MS, 3.32 min (ES+) m/z (relative intensity) 794.18 ([M+H]$^{+\cdot}$, 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(iv) (11S,11aS)-4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (64)

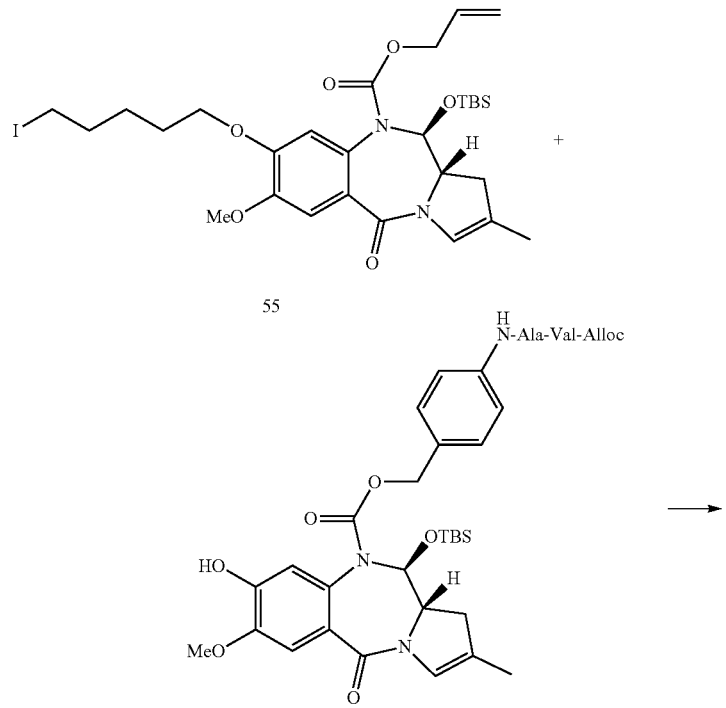

-continued
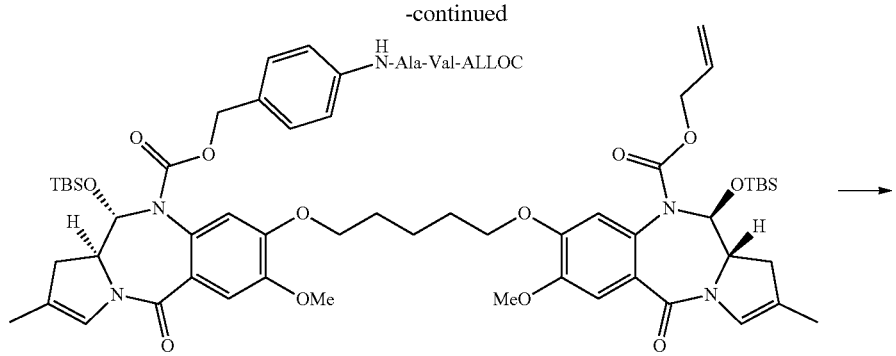
61
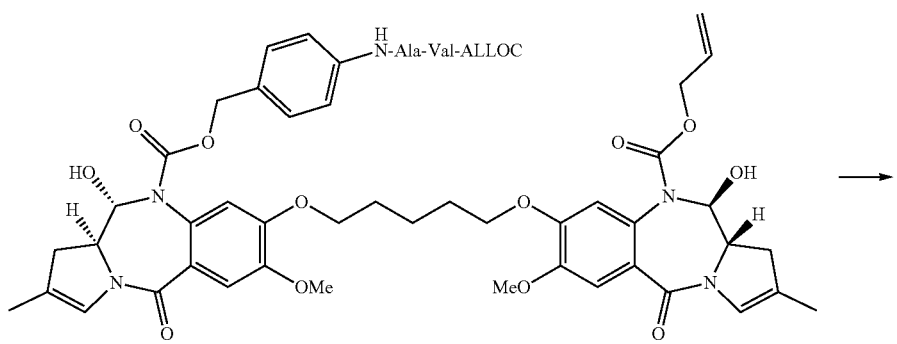
62
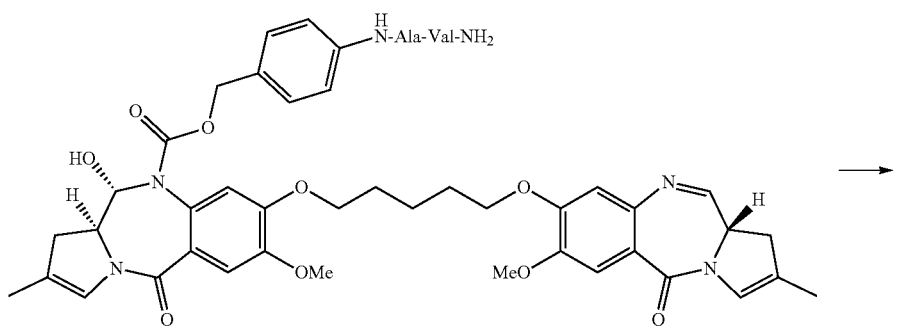
63
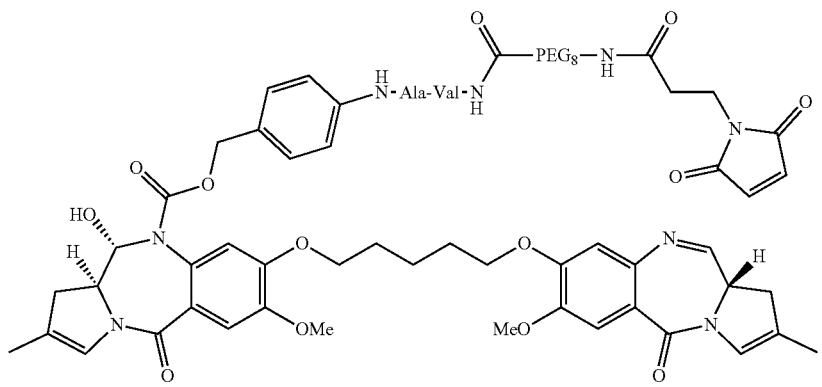
64

(a) (11S)-allyl 8-((5-(((11S)-10-(((4-(2-(1-((1-(ally-loxy)-4-methyl-1,2-dioxopentan-3-yl)amino)-1-oxo-propan-2-yl)hydrazinyl)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)pentyl)oxy)-1-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate (61)

Potassium carbonate (70 mg, 0.504 mmol, 1 eq) was added to a solution of 55 (370 mg, 0.552 mmol, 1.2 eq) and phenol 60 (400 mg, 0.504 mmol) in dry acetone (25 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 61 (385 mg, 57%). LC/MS, 4.07 min (ES+) m/z (relative intensity) 1336.55 ([M+H]+•, 50).

(b) (11S)-allyl 8-((5-(((11S)-0-(((4-(2-(1-((1-(ally-loxy)-4-methyl-1,2-dioxopentan-3-yl)amino)-1-oxo-propan-2-yl)hydrazinyl)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)pentyl)oxy)-11-hydroxy-7-methoxy-2-methyl-5-oxo-11,11a-dihydro-1H-benzo[e]pyrrolo[1,2-a][1,4]diazepine-10(5H)-carboxylate (62)

Tetra-n-butylammonium fluoride (1M, 0.34 mL, 0.34 mmol, 2 eq) was added to a solution of 61 (230 mg, 0.172 mmol) in dry tetrahydrofuran (3 mL). The starting material was totally consumed after 10 minutes. The reaction mixture was diluted with ethyl acetate (30 mL) and washed sequentially with water and brine. The organic phase was dried over magnesium sulphate filtered and excess ethyl acetate removed by rotary evaporation under reduced pressure. The resulting residue 62 was used as a crude mixture for the next reaction. LC/MS, 2.87 min (ES+) m/z (relative intensity) 1108.11 ([M+H]+•, 100).

(c) (11S)-4-(2-(1-((1-amino-3-methyl-1-oxobutan-2-yl)amino)-1-oxopropan-2-yl)hydrazinyl)benzyl 11-hydroxy-7-methoxy-8-((5-((7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (63)

Tetrakis(triphenylphosphine)palladium(0) (12 mg, 0.01 mmol, 0.06 eq) was added to a solution of crude 62 (0.172 mmol) and pyrrolidine (36 µL, 0.43 mmol, 2.5 eq) in dry dichloromethane (10 mL). The reaction mixture was stirred 20 minutes and diluted with dichloromethane and washed sequentially with saturated aqueous ammonium chloride and brine. The organic phase was dried over magnesium sulphate filtered and excess dichloromethane removed by rotary evaporation under reduced pressure. The resulting residue 63 was used as a crude mixture for the next reaction. LC/MS, 2.38 min (ES+) m/z (relative intensity) 922.16 ([M+H]+•, 40).

(d) (11S,11aS)-4-((2S,5S)-37-(2,5-dioxo-2,5-di-hydro-1H-pyrrol-1-yl)-5-isopropyl-2-methy-4,7,35-trioxo-10,13,16,19,22,25,28,31-octaoxa-3,6,34-tri-azaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (64)

1-ethyl-3-(3'-dimethylaminopropyl)carbodiimide (EDCl, 33 mg, 0.172 mmol) was added to a solution of crude 63 (0.172 mmol) and Mal-(PEG)$_8$-acid (100 mg, 0.172 mmol) in dry dichloromethane (10 mL). The reaction was stirred for 2 hours and the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was subjected to flash column chromatography (silica gel; 100% chloroform to 10% methanol in chloroform). Pure fractions were collected and combined and excess eluent was removed by rotary evaporation under reduced pressure to give 64 (E) (60 mg, 25% over 3 steps).

Example 8

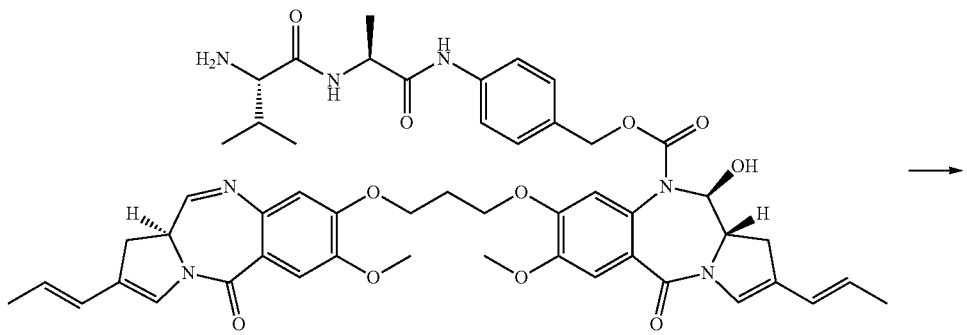

65

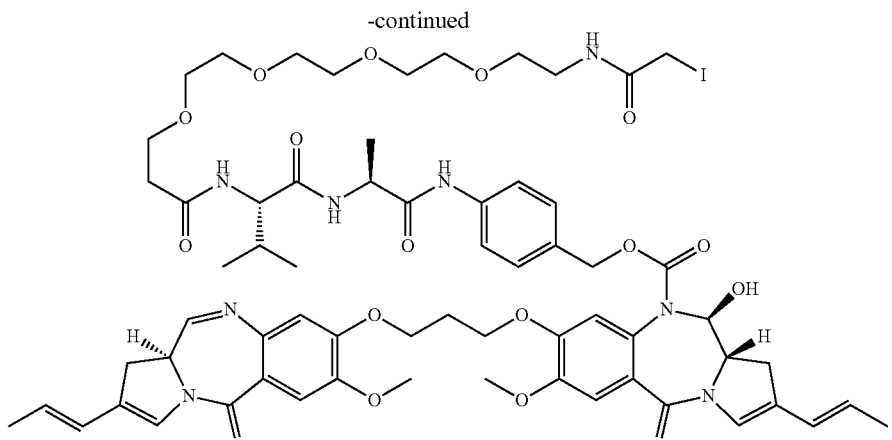

66

Compound 65 is compound 79 of WO 2011/130598

(11S)-4-(1-iodo-20-isopropyl-23-methyl-2,18,21-trioxo-6,9,12,15-tetraoxa-3,19,22-triazatetracosanamido)benzyl 11-hydroxy-7-methoxy-8-(3-((7-methoxy-5-oxo-2-((E)-prop-1-en-1-yl)-5,11a-dihydro-1H-benzo[e]pyrrolo[1,2-a][1,4]diazepin-8-yl)oxy)propoxy)-5-oxo-2-((E)-prop-1-en-1-yl)-11,11a-dihydro-1H-benzo[e]pyrrolo[1,2-a][1,4]diazepine-10(5H)-carboxylate (66)

N,N'-diisopropylcarbodiimide (DIC, 4.71 μL, 0.0304 mmol) was added to a solution of amine 65 (0.0276 mmol) and Iodo-(PEG)$_4$-acid (13.1 mg, 0.0304 mmol) in dry dichloromethane (0.8 mL). The reaction was stirred for 3 hours and the presence of starting material was no longer observed by LC/MS. The reaction mixture was directly loaded onto a thin-layer chromatography, (TLC) plate and purified by prep-TLC (10% methanol in chloroform). Pure bands were scraped off the TLC plate, taken up in 10% methanol in chloroform, filtered and excess eluent removed by rotary evaporation under reduced pressure to give 66 (D) (20.9 mg, 56%). LC/MS, method 2, 3.08 min (ES+) m/z (relative intensity) 1361.16 ([M+H]+, 100).

General Experimental Methods for Example 9

LCMS data were obtained using an Agilent 1200 series LC/MS with an Agilent 6110 quadrupole MS, with Electrospray ionisation. Mobile phase A -0.1% Acetic acid in water. Mobile Phase B-0.1% in acetonitrile. Flow rate of 1.00 ml/min. Gradient from 5% B rising up to 95% B over 3 minutes, remaining at 95% B for 1 minute and then back down to 5% B over 6 seconds. The total run time is 5 minutes. Column: Phenomenex Gemini-NX 3 μm C18, 30×2.00 mm. Chromatograms based on UV detection at 254 nm. Mass Spectra were achieved using the MS in positive mode. Proton NMR chemical shift values were measured on the delta scale at 400 MHz using a Bruker AV400. The following abbreviations have been used: s, singlet; d, doublet; t, triplet; q, quartet; m, multiplet; br, broad. Coupling constants are reported in Hz. Unless otherwise stated, column chromatography (by the flash procedure) were performed on Merck Kieselgel silica (Art. 9385). Mass spectroscopy (MS) data were collected using a Waters Micromass LCT instrument coupled to a Waters 2795 HPLC separations module. Thin Layer Chromatography (TLC) was performed on silica gel aluminium plates (Merck 60, F$_{254}$). All other chemicals and solvents were purchased from Sigma-Aldrich or Fisher Scientific and were used as supplied without further purification.

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, F$_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220

Example 9

(i) Key Intermediates

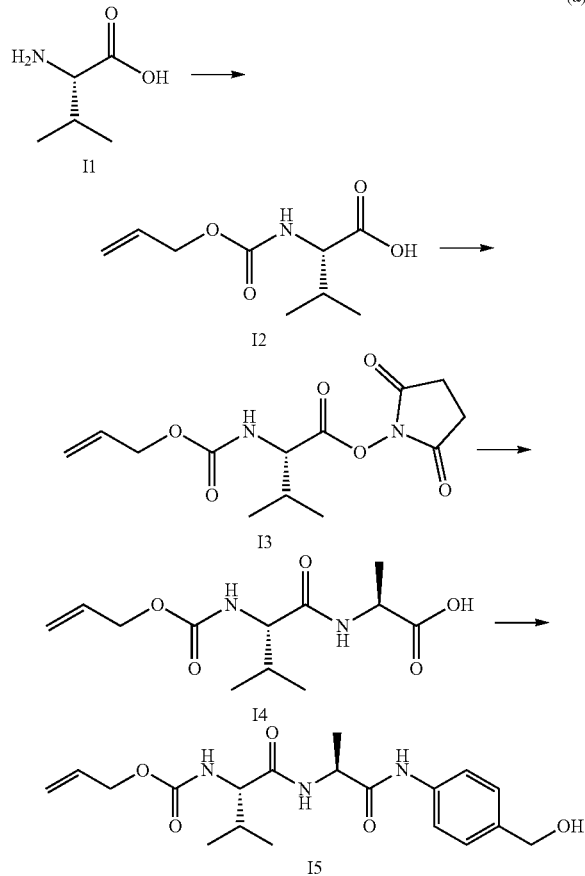

(a-i) (S)-2-(allyloxycarbonylamino)-3-methylbutanoic acid (12)

Allyl chloroformate (36.2 ml, 340.59 mmol, 1.2 eq) was added dropwise to a stirred solution of L-valine (11)(33.25 g, 283.82 mmol, 1.0 eq) and potassium carbonate (59.27 g, 425.74 mmol, 1.5 eq) in water (650 mL) and THF (650 mL). The reaction mixture was stirred at room temperature for 18 hours, then the solvent was concentrated under reduced pressure and the remaining solution extracted with diethyl ether (3×100 mL). The aqueous portion was acidified to pH 2 with conc. HCl and extracted with DCM (3×100 mL). The combined organics were washed with brine, dried over MgSO$_4$, filtered and concentrated under reduced pressure to afford the product as a colourless oil (57.1 g, assumed 100% yield). LC/MS (1.966 min (ES$^+$)), m/z: 202.1 [M+H]$^+$. $^1$H NMR (400 MHz, DMSO-d$_6$) δ 12.57 (br s, 1H), 7.43 (d, 1H, J=8.6 Hz), 5.96-5.86 (m, 1H), 5.30 (ddd, 1H, J=17.2, 3.4, 1.7 Hz), 5.18 (ddd, 1H, J=10.4, 2.9, 1.6 Hz), 4.48 (dt, 2H, J=5.3, 1.5 Hz), 3.85 (dd, 1H, J=8.6, 6.0 Hz), 2.03 (oct, 1H, J=6.6 Hz), 0.89 (d, 3H, J=6.4 Hz), 0.87 (d, 3H, J=6.5 Hz).

(a-ii) (S)-2,5-dioxopyrrolidin-1-yl 2-(allyloxycarbonylamino)-3-methylbutanoate (13)

To a stirred solution of the protected acid 12 (60.6 g, 301.16 mmol, 1.0 eq) and N-hydroxysuccinimide (34.66 g, 301.16 mmol, 1.0 eq) in dry THF (800 mL) was added dicyclohexylcarbodiimide (62.14 g, 301.16 mmol, 1 eq). The reaction was stirred for 18 hours at room temperature. The reaction mixture was then filtered, the solid washed with THF and the combined filtrate was concentrated under reduced pressure. The residue was re-dissolved in DCM and left to stand at 00° C. for 30 minutes. The suspension was filtered and washed with cold DCM. Concentration of the filtrate under reduced pressure afforded the product as a viscous colourless oil (84.7 g, assumed 100% yield) which was used in the next step without further purification. LC/MS (2.194 min (ES$^+$)), m/z: 321.0 [M+Na]$^+$. $^1$H NMR (400 MHz, DMSO-d$_6$) δ 8.0 (d, 1H, J=8.3 Hz), 5.97-5.87 (m, 1H), 5.30 (ddd, 1H, J=17.2, 3.0, 1.7 Hz), 5.19 (ddd, 1H, J=10.4, 2.7, 1.4 Hz), 4.52 (dt, 2H, J=5.3, 1.4 Hz), 4.32 (dd, 1H, J=8.3, 6.6 Hz), 2.81 (m, 4H), 2.18 (oct, 1H, J=6.7 Hz), 1.00 (d, 6H, J=6.8 Hz).

(a-iii) (S)-2-((S)-2-(allyloxycarbonylamino)-3-methylbutanamido)propanoic acid (14)

A solution of succinimide ester 13(12.99 g, 43.55 mmol, 1.0 eq) in THF (50 mL) was added to a solution of L-alanine (4.07 g, 45.73 mmol, 1.05 eq) and NaHCO$_3$ (4.02 g, 47.90 mmol, 1.1 eq) in THF (100 mL) and H$_2$O (100 mL). The mixture was stirred at room temperature for 72 hours when the THF was removed under reduced pressure. The pH was adjusted to 3-4 with citric acid to precipitate a white gum. After extraction with ethyl acetate (6×150 mL), the combined organics were washed with H$_2$O (200 mL), dried over MgSO$_4$, filtered and concentrated under reduced pressure. Trituration with diethyl ether afforded the product as a white powder which was collected by filtration and washed with diethyl ether (5.78 g, 49%). LC/MS (1.925 min (ES$^+$)), m/z: 273.1 [M+H]$^+$. $^1$H NMR (400 MHz, DMSO-d$_6$) δ 12.47 (br s, 1H), 8.17 (d, 1H, J=6.8 Hz), 7.16 (d, 1H, J=9.0 Hz), 5.95-5.85 (m, 1H), 5.29 (dd, 1H, J=17.2, 1.7 Hz), 5.17 (dd, 1H, J=10.4, 1.5 Hz), 4.46 (m, 2H), 4.18 (quin, 1H, J=7.2 Hz), 3.87 (dd, 1H, J=9.0, 7.1 Hz), 1.95 (oct, 1H, J=6.8 Hz), 1.26 (d, 3H, J=7.3 Hz), 0.88 (d, 3H, J=6.8 Hz), 0.83 (d, 3H, J=6.8 Hz).

(a-iv) Allyl (S)-1-((S)-1-(4-(hydroxymethyl)phenylamino)-1-oxopropan-2-ylamino)-3-methyl-1-oxobutan-2-ylcarbamate (15)

EEDQ (5.51 g, 22.29 mmol, 1.05 eq) was added to a solution of p-aminobenzyl alcohol (2.74 g, 22.29 mmol, 1.05 eq) and acid 14 (5.78 g, 21.23 mmol, 1 eq) in dry THF (100 mL), and stirred at room temperature for 72 hours. The reaction mixture was then concentrated under reduced pressure and the resulting brown solid was triturated with diethyl ether and filtered with subsequent washing with an excess of diethyl ether to afford the product as an off-white solid (7.1 g, 88%). LC/MS (1.980 min (ES$^+$)), m/z: 378.0 [M+H]$^-$ $^1$H NMR (400 MHz, DMSO-d$_6$) δ 9.89 (br s, 1H), 8.13 (d, 1H, J=7.0 Hz), 7.52 (d, 2H, J=8.5 Hz), 7.26 (m, 1H), 7.23 (d, 2H, J=8.5 Hz), 5.91 (m, 1H), 5.30 (m, 1H), 5.17 (m, 1H), 4.46 (m, 2H), 5.09 (t, 1H, J=5.6 Hz), 4.48 (m, 2H), 4.42 (m, 3H), 3.89 (dd, 1H, J=8.6, 6.8 Hz), 1.97 (m, 1H), 1.30 (d, 3H, J=7.1 Hz), 0.88 (d, 3H, J=6.8 Hz), 0.83 (d, 3H, J=6.7 Hz).

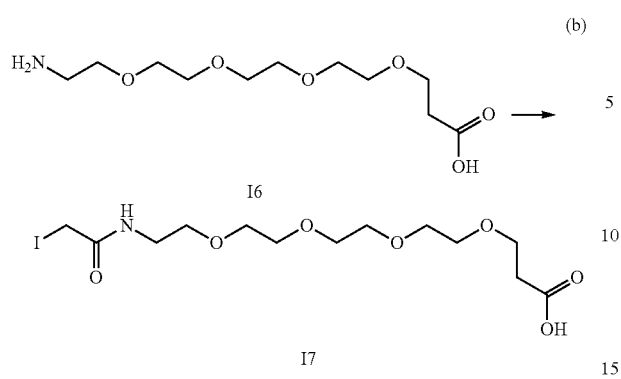

1-iodo-2-oxo-6,9,12,15-tetraoxa-3-azaoctadecan-18-oic acid (17)

A solution of iodoacetic anhydride (0.250 g, 0.706 mmol, 1.1 eq) in dry DCM (1 mL) was added to amino-PEG$_{(4)}$-acid 16 (0.170 g, 0.642 mmol, 1.0 eq) in DCM (1 mL). The mixture was stirred in the dark at room temperature overnight. The reaction mixture was washed with 0.1 M HCl, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as an orange oil (0.118 g, 42%). LC/MS (1.623 min (ES$^+$)), m/z: 433.98 [M+H]$^+$. $^1$H NMR (400 MHz, CDCl$_3$) δ 8.069 (s, 1H), 7.22 (br s, 1H), 3.79 (t, 2H, J=5.8 Hz), 3.74 (s, 2H), 3.72-3.58 (m, 14H), 3.50-3.46 (m, 2H), 2.62 (t, 2H, J=5.8 Hz).

(ii) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (74)

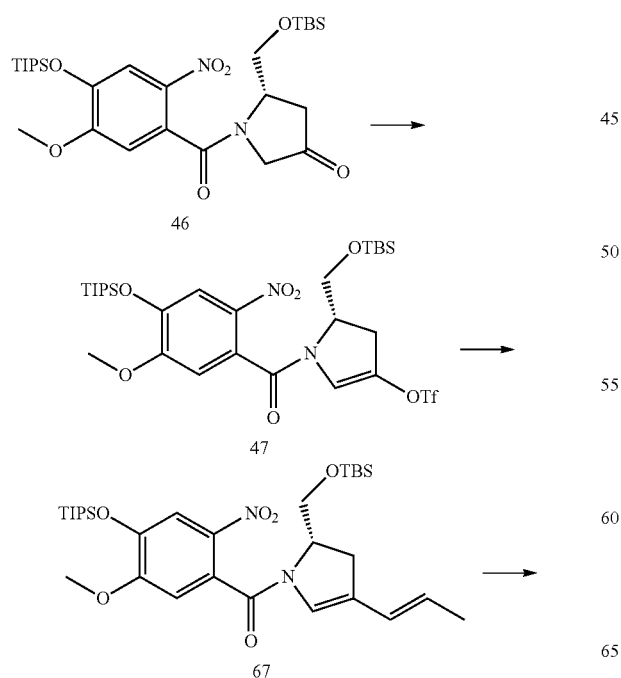

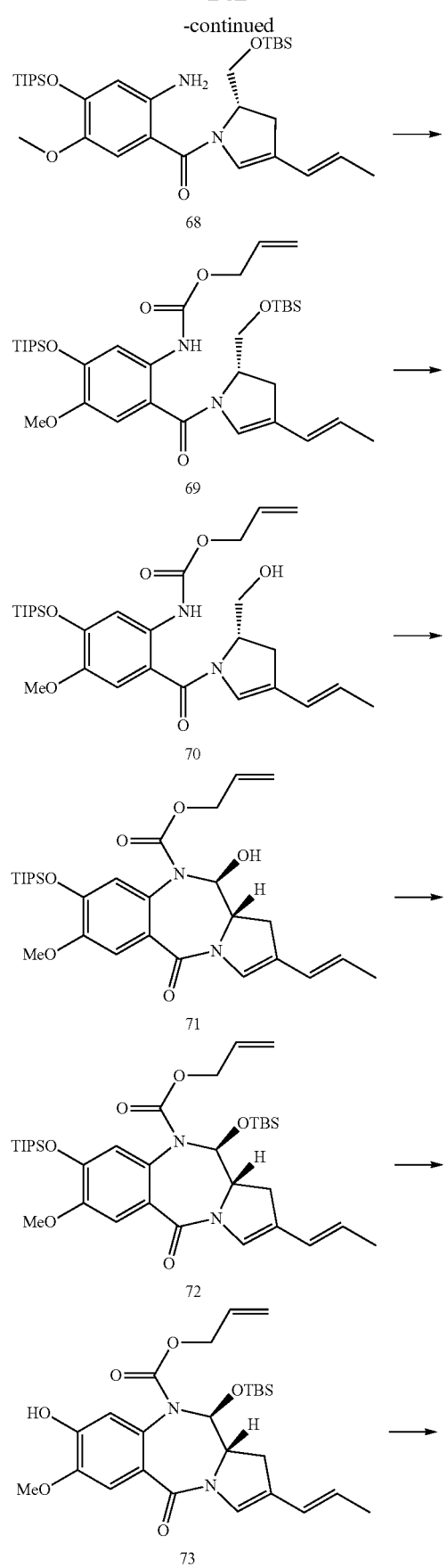

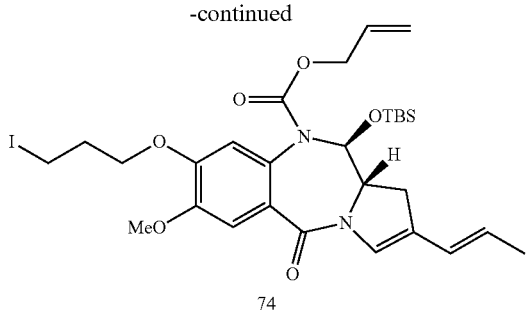

74

(a) (S)-5-((tert-butyldimethylsilyloxy)methyl)-1-(5-methoxy-2-nitro-4-(triisopropylsilyloxy)benzoyl)-4,5-dihydro-1H-pyrrol-3-yl trifluoromethanesulfonate (47)

Triflic anhydride (28.4 g, 100.0 mmol, 3.0 eq) was added dropwise, over 25 mins, to a vigorously stirred solution of the ketone 46 (19.5 g, 30.0 mmol, 1.0 eq) in DCM (550 mL) containing 2,6-lutidine (14.4 g, 130.0 mmol, 4.0 eq) at −50° C. The reaction mixture was stirred for 1.5 hours when LC/MS indicated complete reaction. The organic phase was washed successively with water (100 mL), saturated sodium bicarbonate (150 mL), brine (50 mL), and the organic phase was dried over $MgSO_4$, filtered and concentrated under reduced pressure. The residue was purified by flash chromatography (silica gel, 90/10 v/v n-hexane/EtOAc) to afford the product as a pale yellow oil (19.5 g, 82%). LC/MS (4.391 min (ES$^+$)), m/z: 713.25 [M+H]$^+$. $^1$H NMR (400 MHz, CDCl$_3$) δ 7.68 (s, 1H), 6.72 (s, 1H), 6.02 (t, 1H, J=1.9 Hz), 4.75 (m, 1H), 4.05 (m, 2H), 3.87 (s, 3H), 3.15 (ddd, 1H, J=16.2, 10.3, 2.3 Hz), 2.96 (ddd, 1H, J=16.2, 4.0, 1.6 Hz), 1.28-1.21 (m, 3H), 1.07 (d, 18H, J=7.2 Hz), 0.88 (s, 9H), 0.09 (s, 3H), 0.08 (s, 3H).

(b) (S,E)-(2-((tert-butyldimethylsilyloxy)methyl)-4-(prop-1-enyl)-2,3-dihydro-1H-pyrrol-1-yl)(5-methoxy-2-nitro-4-(triisopropylsilyloxy)phenyl)methanone (67)

Tetrakis(triphenylphosphine)palladium(0) (0.41 g, 0.35 mmol, 0.03 eq) was added to a mixture of the triflate 47 (8.4 g, 11.8 mmol, 1.0 eq), E-1-propene-1-ylboronic acid (1.42 g, 16.5 mmol, 1.4 eq) and potassium phosphate (5.0 g, 23.6 mmol, 2.0 eq) in dry dioxane (60 mL) under a nitrogen atmosphere. The mixture was stirred at 25° C. for 120 mins when LC/MS indicated complete reaction. Ethyl acetate (120 mL) and water (120 mL) were added, the organic phase was removed, washed with brine (20 mL), dried over $MgSO_4$, filtered and concentrated under reduced pressure. The residue was purified by flash chromatography (silica gel, 95/5 v/v n-hexane/EtOAc to 90/10 v/v n-hexane/EtOAc) to afford the product as a yellow foam (4.96 g, 70%). LC/MS (4.477 min (ES$^+$)), m/z: 605.0 [M+H]$^+$. $^1$H NMR (400 MHz, CDCl$_3$) δ 7.67 (s, 1H), 6.74 (s, 1H), 5.93 (d, 1H, J=15.4 Hz), 5.67 (s, 1H), 4.65 (m, 1H), 4.04 (m, 2H), 3.86 (s, 3H), 2.85 (m, 1H), 2.71 (m, 1H), 1.72 (dd, 3H, J=6.8, 1.0 Hz), 1.30-1.22 (m, 3H), 1.07 (d, 18H, J=7.2 Hz), 0.87 (s, 9H), 0.08 (s, 3H), 0.07 (s, 3H).

(c) (S,E)-(2-amino-5-methoxy-4-(triisopropylsilyloxy)phenyl) (2-((tert-butyldimethylsilyloxy)methyl)-4-(prop-1-enyl)-2,3-dihydro-1H-pyrrol-1-yl)methanone (68)

Zinc dust (22.0 g, 0.33 mol, 37 eq) was added, in portions over 20 mins, to a solution of the propenyl intermediate 67 (5.5 g, 9.1 mmol, 1.0 eq) in 5% v/v formic acid/ethanol (55 mL), using an ice bath to maintain the temperature between 25-30° C. After 30 mins, the reaction mixture was filtered through a short bed of Celite®. The Celite® was washed with ethyl acetate (65 mL) and the combined organics were washed successively with water (35 mL), saturated sodium bicarbonate (35 mL) and brine (10 mL). The organic phase was dried over $MgSO_4$, filtered and concentrated under reduced pressure. The residue was purified by flash chromatography (silica gel, 90/10 v/v n-hexane/EtOAc) to afford the product as a pale yellow oil (3.6 g, 69.0%). LC/MS (4.439 min (ES$^+$)), m/z: 575.2 [M+H]$^+$. $^1$H NMR (400 MHz, CDCl$_3$) b 6.75 (m, 1H), 6.40 (br s, 1H), 6.28 (m, 1H), 6.11 (d, 1H, J=15.4 Hz), 5.53 (m, 1H), 4.67 (m, 1H), 4.36 (m, 2H), 3.93 (br s, 1H), 3.84 (br s, 1H), 3.73 (s, 3H), 2.86 (dd, 1H, J=15.7, 10.4 Hz), 2.73 (dd, 1H, J=15.9, 4.5 Hz), 1.80 (dd, 3H, J=6.8, 1.3 Hz), 1.35-1.23 (m, 3H), 1.12 (d, 18H, J=7.3 Hz), 0.89 (s, 9H), 0.08 (s, 3H), 0.07 (s, 3H).

(d) (S,E)-allyl 2-(2-((tert-butyldimethylsilyloxy)methyl)-4-(prop-1-enyl)-2,3-dihydro-1H-pyrrole-1-carbonyl)-4-methoxy-5-(triisopropylsilyloxy)phenylcarbamate (69)

Allyl chloroformate (0.83 g, 6.88 mmol, 1.1 eq) was added to a solution of the amine 68 (3.6 g, 6.26 mmol, 1.0 eq) in dry DCM (80 mL) containing dry pyridine (1.09 g, 13.77 mmol, 2.2 eq) at −78° C. The dry ice was removed and the reaction mixture allowed to warm to room temperature. After stirring for a further 15 minutes, LC/MS indicated complete reaction. The organic phase was washed successively with 0.01N HCl (50 mL), saturated sodium bicarbonate (50 mL), brine (10 mL), dried over $MgSO_4$, filtered and concentrated under reduced pressure to leave a pale yellow oil which was used in the next step without further purification (4.12 g, assumed 100% yield). LC/MS (4.862 min (ES$^+$)), m/z: 659.2 [M+H]$^+$.

(e) (S,E)-allyl 2-(2-(hydroxymethyl)-4-(prop-1-enyl)-2,3-dihydro-1H-pyrrole-1-carbonyl)-4-methoxy-5-(triisopropylsilyloxy)phenylcarbamate (70)

The crude intermediate 69 (assumed 100% yield, 4.12 g, 6.25 mmol, 1.0 eq) was dissolved in a mixture of acetic acid (70 mL), methanol (10 mL), THF (10 mL) and water (20 mL) and allowed to stir at room temperature. After 6 hours the reaction mixture was diluted with ethyl acetate (500 mL) and washed successively with water (2×500 mL), saturated sodium bicarbonate (300 mL) and brine (50 mL). The organic phase was dried over $MgSO_4$, filtered and concentrated under reduced pressure. The residue was purified by flash chromatography (silica gel, 1/99 v/v methanol/DCM to 5/95 v/v methanol/DCM) to afford the product as a yellow oil and a further 1 g of unreacted starting material was recovered. This material was subjected to the same reaction conditions as above, but was left stirring for 16 h. After work up and purification, additional product was isolated (2.7 g, 79%, 2 steps) LC/MS (3.742 min (ES$^+$)), m/z: 545.2 [M+H]$^+$. $^1$H NMR (400 MHz, CDCl$_3$) δ 8.38 (m, 1H), 7.72 (m, 1H), 6.81 (s, 1H), 6.37 (m, 1H), 6.10 (d, 1H, J=15.8 Hz), 5.97 (m, 1H), 5.53 (m, 1H), 5.36 (ddd, 1H, J=17.2, 3.1, 1.5 Hz), 5.25 (ddd, 1H, J=10.4, 2.5, 1.3 Hz), 4.78 (m, 1H), 4.65 (dt, 2H, J=5.7, 1.3 Hz), 3.84 (m, 3H), 3.79 (s, 3H), 3.04 (dd, 1H, J=16.7, 10.5 Hz), 2.40 (dd, 1H, J=16.0, 4.5 Hz), 1.82 (dd, 3H, J=6.8, 1.0 Hz), 1.36-1.26 (m, 3H), 1.14 (d, 18H, J=7.3 Hz).

(f) (11S,11aS)-allyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (71)

Dry dimethyl sulfoxide (1.16 g, 14.87 mmol, 3.0 eq) was added dropwise to a solution of oxalyl chloride (0.94 g, 7.43 mmol, 1.5 eq) in DCM (25 mL) at −78° C. under an atmosphere of nitrogen. Maintaining the temperature at −78° C., after 10 mins a solution of the primary alcohol 70 (2.7 g, 4.96 mmol, 1.0 eq) in DCM (20 mL) was added dropwise. After a further 15 mins, dry triethylamine (2.5 g, 24.78 mmol, 5.0 eq) was added, and the reaction mixture allowed to warm to room temperature. The reaction mixture was washed successively with cold 0.1N HCl (50 mL), saturated sodium hydrogen carbonate (50 mL) and brine (10 mL) and the organic layer was dried over MgSO$_4$, filtered and concentrated under reduced pressure to afford the product as a yellow oil which was used in the next step without further purification (2.68 g, assumed 100% yield). LC/MS (3.548 min (ES$^+$)), m/z: 543.2 [M+H]$^+$.

(g) (11S,11aS)-allyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (72)

Tert-butyldimethylsilyltrifluoromethane sulfonate (3.93 g, 14.87 mmol, 3.0 eq) was added to a solution of the carbinolamine 71 (assumed 100% yield, 2.68 g, 4.96 mmol, 1.0 eq) and 2,6-lutidine (2.12 g, 19.83 mmol, 4.0 eq) in dry DCM (40 mL) at 0° C. under an atmosphere of nitrogen. After 10 minutes, the reaction mixture was allowed to warm to room temperature and stirred for a further 60 minutes. The organic phase was washed successively with water (10 mL), saturated sodium bicarbonate (10 mL) and brine (5 mL), dried over MgSO$_4$, filtered and concentrated under reduced pressure. The residue was purified by flash chromatography (silica gel, chloroform to 2/98 v/v Methanol/chloroform) to afford the product as a yellow oil (2.0 g, 63%, 2 steps). LC/MS (4.748 min (ES$^+$)), m/z: 657.2 [M+H]$^+$. $^1$H NMR (400 MHz, CDCl$_3$) δ 7.19 (s, 1H), 6.86 (m, 1H), 6.66 (s, 1H), 6.22 (d, 1H, J=15.4 Hz), 5.81 (d, 1H, J=8.8 Hz), 5.78 (m, 1H), 5.48 (m, 1H), 5.11 (d, 1H, J=5.0 Hz), 5.08 (m, 1H), 4.58 (dd, 1H, J=13.4, 5.4 Hz), 4.35 (dd, 1H, J=13.2, 5.7 Hz), 3.83 (s, 3H), 3.76 (s, 3H), 3.00 (dd, 1H, J=15.6, 11.0 Hz), 2.53 (m, 1H), 1.81 (dd, 3H, J=6.8, 0.9 Hz), 1.30-1.18 (m, 3H), 1.08 (d, 9H, J=2.3 Hz), 1.06 (d, 9H, J=2.3 Hz), 0.86 (s, 9H), 0.25 (s, 3H), 0.18 (s, 3H).

(h) (11S,11aS)-allyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (73)

Lithium acetate dihydrate (0.31 g, 3.04 mmol, 1.0 eq) was added to a solution of the diazepine 72 (2.0 g, 3.04 mmol, 1.0 eq) in wet DMF (20 mL) at 25° C. and stirred for 4 hours. The reaction mixture was diluted with ethyl acetate (200 mL) and washed successively with 0.1M citric acid (50 mL, pH 3), water (50 mL) and brine (10 mL), dried over MgSO$_4$, filtered and concentrated under reduced pressure. The residue was purified by flash chromatography (silica gel, 50/50 v/v n-hexane/EtOAc to 25/75 v/v n-hexane/EtOAc) to afford the product as a pale yellow solid (0.68 g, 45%). LC/MS (3.352 min (ES$^+$)), m/z: 501.1 [M+H]$^+$. $^1$H NMR (400 MHz, CDCl$_3$) δ 7.02 (s, 1H), 6.66 (m, 1H), 6.53 (s, 1H), 6.03 (d, 1H, J=15.5 Hz), 5.80 (s, 1H), 5.63 (d, 1H, J=8.9 Hz), 5.55 (m, 1H), 5.29 (m, 1H), 4.87 (m, 2H), 4.39 (dd, 1H, J=13.5, 4.2 Hz), 4.20 (dd, 1H, J=13.2, 5.7 Hz), 3.73 (s, 3H), 3.59 (m, 1H), 2.81 (dd, 1H, J=16.1, 10.5 Hz), 2.35 (d, 1H, J=15.7 Hz), 1.61 (d, 3H, J=6.4 Hz), 0.67 (s, 9H), 0.05 (s, 3H), 0.00 (s, 3H).

(i) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (74)

Diiodopropane (0.295 g, 1.00 mmol, 5.0 eq) and potassium carbonate (0.028 g, 0.20 mmol, 1.0 eq) were added to a solution of the phenol 33 (0.100 g, 0.020 mmol, 1.0 eq) in dry acetone (5 mL). The reaction mixture was heated at 60° C. for 6 hours when LC/MS showed complete reaction. The reaction mixture was concentrated to dryness under reduced pressure and the residue was purified by flash chromatography (silica gel, 75/25 v/v n-hexane/EtOAc to 50/50 v/v n-hexane/EtOAc) to afford the product as a colourless oil (0.074 g, 56%). LC/MS (3.853 min (ES$^+$)), m/z: 669.0 [M+H]$^+$. $^1$H NMR (400 MHz, CDCl$_3$) δ 7.26 (s, 1H), 6.90 (s, 1H), 6.68 (s, 1H), 6.24 (d, 1H, J=15.3 Hz), 5.87 (d, 1H, J=8.9 Hz), 5.78 (m, 1H), 5.53 (m, 1H), 5.12 (m, 2H), 4.65 (m, 2H), 4.41 (m, 1H), 4.11 (m, 1H), 3.93 (s, 3H), 3.81 (m, 1H), 3.40 (t, 2H, J=6.7 Hz), 3.05 (dd, 1H, J=16.3, 10.1 Hz), 2.57 (m, 1H), 2.34 (m, 2H), 1.84 (d, 3H, J=6.6 Hz), 0.92 (s, 9H), 0.28 (s, 3H), 0.26 (s, 3H).

(iii) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate 79)

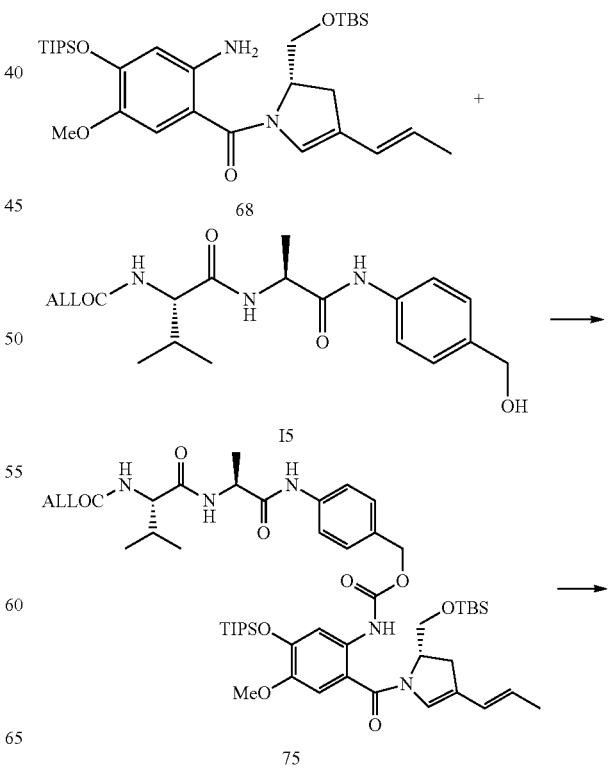

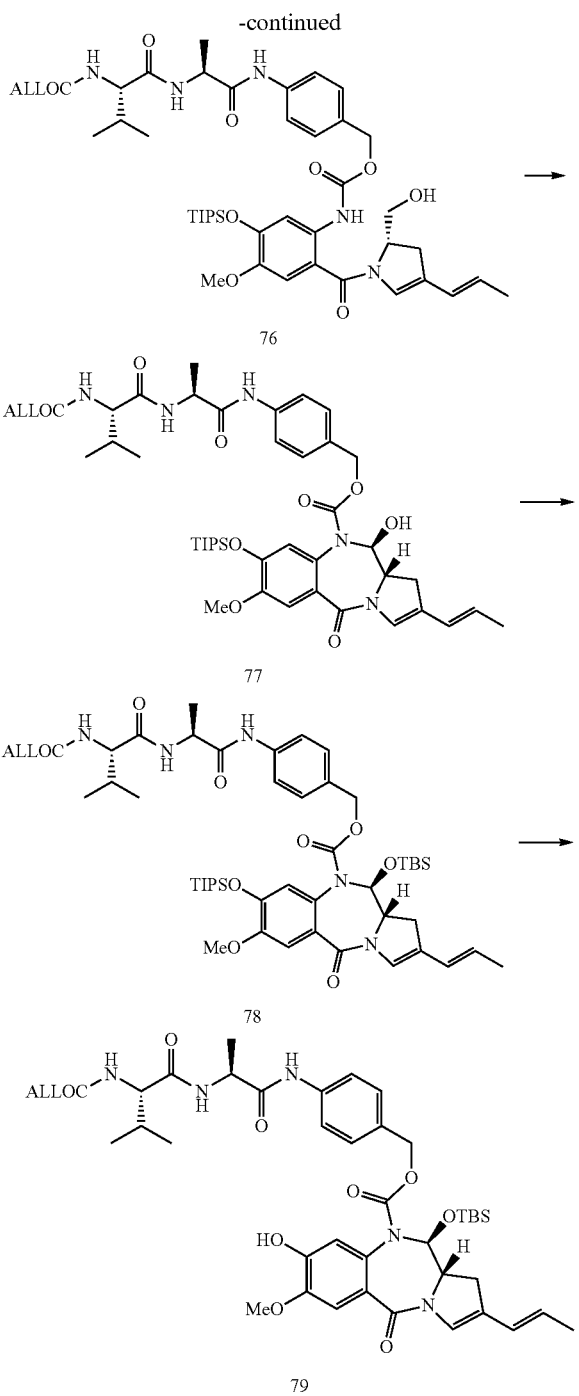

(a) Allyl ((S)-1-(((S)-1-((4-(((((2-((S)-2-(((tert-butyldimethylsilyl)oxy)methyl)-4-((E)-prop-1-en-1-yl)-2,3-dihydro-1H-pyrrole-1-carbonyl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl)carbamate (75)

Triethylamine (0.256 mL, 1.84 mmol, 2.2 eq) was added to a stirred solution of the amine 68 (0.480 g, 0.835 mmol, 1.0 eq) and triphosgene (0.089 g, 0.301 mmol, 0.36 eq) in dry THF (15 mL) at 5° C. (ice bath). The progress of the isocyanate reaction was monitored by periodically removing aliquots from the reaction mixture and quenching with methanol and performing LCMS analysis. Once the isocyanate reaction was complete a solution of Alloc-Val-Ala-PABOH 15 (0.473 g, 1.25 mmol, 1.5 eq) and triethylamine (0.174 mL, 1.25 mmol, 1.5 eq) in dry THF (10 mL) was rapidly added by injection to the freshly prepared isocyanate. The reaction was allowed to stir at 40° C. for 4 hours followed by stirring at room temperature overnight. The mixture was concentrated under reduced pressure, and purified by flash chromatography (silica gel, 20/80 v/v n-hexane/EtOAc to 50/50 v/v n-hexane/EtOAc, then 1/99 v/v DCM/MeOH to 5/95 v/v DCM/MeOH) to afford the product as a yellow solid (0.579 g, 71%). LC/MS (4.468 min (ES$^+$)), m/z: 978.55 [M+H]$^+$. $^1$H NMR (400 MHz, CDCl$_3$) δ 8.63 (br s, 1H), 8.42 (s, 1H), 7.78 (br s, 1H), 7.53 (d, 2H, J=8.1 Hz), 7.31 (d, 2H, J=8.6 Hz), 6.76 (s, 1H), 6.59 (d, 1H, J=7.6 Hz), 6.36 (br s, 1H), 6.04 (d, 1H, J=15.9 Hz), 5.90 (m, 1H), 5.55 (m, 1H), 5.33-5.21 (m, 3H), 5.10 (s, 2H), 4.66 (m, 2H), 4.57 (dd, 2H, J=5.6, 1.0 Hz), 3.98 (dd, 1H, J=7.3, 6.8 Hz), 3.90 (m, 1H), 3.81 (m, 1H), 3.78 (s, 3H), 2.82 (dd, 1H, J=15.4, 9.6 Hz), 2.72 (dd, 1H, J=15.9, 3.5 Hz), 2.17 (m, 1H), 1.78 (dd, 3H, J=6.5, 0.8 Hz), 1.46 (d, 3H, J=7.1 Hz), 1.29 (m, 3H), 1.11 (d, 18H, J=7.1 Hz), 0.97 (d, 3H, J=6.8 Hz), 0.92 (d, 3H, J=6.8 Hz), 0.83 (s, 9H), 0.04 (s, 3H), 0.01 (s, 3H).

(b) Allyl ((S)-1-(((S)-1-((4-((((2-((S)-2-(hydroxymethyl)-4-((E)-prop-1-en-1-yl)-2,3-dihydro-1H-pyrrole-1-carbon yl)-4-methoxy-5-((triisopropylsilyl)oxy)phenyl)carbamoyl)oxy)methyl)phenyl)amino)-1-oxopropan-2-yl)amino)-3-methyl-1-oxobutan-2-yl) carbamate (76)

The silyl ether 75 (1.49 g, 1.52 mmol, 1.0 eq) was dissolved in a 7:1:1:2 mixture of acetic acid/methanol/tetrahydrofuran/water (14:2:2:4 mL) and allowed to stir at room temperature. After 2 hours the reaction was diluted with EtOAc (100 mL), washed sequentially with water, aq. sodium bicarbonate then brine. The organic phase was then dried over MgSO$_4$, filtered and concentrated under reduced pressure. The residue was purified by flash chromatography (silica gel, 100/0 then 99/1 to 92/8 v/v DCM/MeOH) to afford the product as an orange solid (1.2 g, 92%). LC/MS (3.649 min (ES$^+$)), m/z: 865.44 [M+H]$^+$. $^1$H NMR (400 MHz, CDCl$_3$) δ 8.44 (s, 1H), 8.35 (s, 1H), 7.69 (br s, 1H), 7.53 (d, 2H, J=8.7 Hz), 7.32 (d, 2H, J=8.3 Hz), 6.78 (s, 1H), 6.56 (m, 2H), 6.32 (br s, 1H), 6.05 (d, 1H, J=14.9 Hz), 5.90 (m, 1H), 5.56 (m, 1H), 5.30 (m, 2H), 5.22 (m, 1H), 5.10 (d, 2H, J=3.1 Hz), 4.73 (m, 1H), 4.64 (m, 1H), 4.57 (d, 2H, J=5.8 Hz), 4.01 (m, 1H), 3.79 (m, 2H), 3.76 (s, 3H), 2.98 (dd, 1H, J=16.3, 10.2 Hz), 2.38 (dd, 1H, J=16.6, 4.1 Hz), 2.16 (m, 1H), 1.78 (dd, 3H, J=6.8, 0.9 Hz), 1.46 (d, 3H, J=7.1 Hz), 1.29 (m, 3H), 1.11 (d, 18H, J=7.4 Hz), 0.97 (d, 3H, J=6.7 Hz), 0.92 (d, 3H, J=6.8 Hz).

(c) (11S,11aS)-4-((S)-2-((S)-2-(allyloxycarbonylamino)-3-methylbutanamido)propanamido)benzyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (77)

Dry dimethyl sulfoxide (0.180 g, 2.3 mmol, 3.0 eq) was added dropwise to a solution of oxalyl chloride (0.147 g, 1.1 mmol, 1.5 eq) in DCM (10 mL) at −78° C. under an atmosphere of nitrogen. Maintaining the temperature at −78° C., after 20 minutes, a solution of the primary alcohol 76 (0.666 g, 0.77 mmol, 1.0 eq) in DCM (10 mL) was added dropwise. After a further 15 minutes, dry triethylamine (0.390 g, 3.85 mmol, 5.0 eq) was added, and the reaction mixture allowed to warm to room temperature. The reaction mixture was washed successively with cold 0.1N HCl (10 mL), saturated sodium hydrogen carbonate (10 mL) and brine (5 mL). The organic layer was then dried over MgSO$_4$, filtered and concentrated under reduced pressure. The residue was then purified by flash chromatography (silica gel, 50/50 v/v n-hexane/EtOAc to 25/75 v/v n-hexane/EtOAc) to afford the product as a white solid (0.356 g, 54%). LC/MS (3.487 min (ES$^+$)), m/z: 862.2 [M+H]$^+$. $^1$H NMR (400 MHz, CDCl$_3$) 8.34 (br s, 1H), 7.47 (d, 2H, J=7.6 Hz), 7.17 (s, 1H), 7.14 (d, 2H, J=7.5 Hz), 6.86 (br s, 1H), 6.65 (br s, 1H), 6.42 (d, 1H, J=7.6 Hz), 6.22 (d, 1H, J=14.4 Hz), 5.80 (m, 1H), 5.40 (m, 1H), 5.53 (m, 1H), 5.32 (m, 1H), 5.21 (d, 2H, J=9.6 Hz), 5.06 (d, 1H, J=12.3 Hz), 4.90 (m, 1H), 4.58 (m, 3H), 3.98 (m, 1H), 3.84 (m, 1H), 3.81 (s, 3H), 3.50 (m, 1H), 3.05 (dd, 1H, J=16.0, 10.3 Hz), 2.76 (m, 1H), 2.15 (m, 1H), 1.80 (dd, 3H, J=6.7, 0.8 Hz), 1.44 (d, 3H, J=7.1 Hz), 1.16 (m, 3H), 1.01 (d, 18H, J=6.6 Hz), 0.96 (d, 3H, J=6.8 Hz), 0.92 (d, 3H, J=6.8 Hz).

(d) (11S,11aS)-4-((S)-2-((S)-2-(allyloxycarbonylamino)-3-methylbutanamido)propanamido)benzyl 11-(tert-butyldimethylsilyloxy)-7-methoxy-5-OXO-2-((E)-prop-1-enyl)-8-(triisopropylsilyloxy)-11,11a-dihydro-1H-benzo[e]pyrrolo[1,2-a][1,4]diazepine-10(5H)-carboxylate (78)

Tert-butyldimethylsilyltrifluoromethane sulfonate (0.46 g, 1.74 mmol, 3.0 eq) was added to a solution of secondary alcohol 77 (0.5 g, 0.58 mmol, 1.0 eq) and 2,6-lutidine (0.25 g, 2.32 mmol, 4.0 eq) in dry DCM (10 mL) at 0° C. under an atmosphere of nitrogen. After 10 minutes, the reaction mixture was allowed to warm to room temperature and stirred for a further 120 mins. The organic phase was then washed successively with water (10 mL), saturated sodium bicarbonate (10 mL) and brine (5 mL), dried over MgSO$_4$, filtered and concentrated under reduced pressure. The residue was purified by flash chromatography (silica gel, 50/50 v/v n-hexane/EtOAc) to afford the product as a white solid (0.320 g, 57%). LC/MS (4.415 min (ES$^+$)), m/z: 976.52 [M+H]$^+$. $^1$H NMR (400 MHz, CDCl$_3$) δ 8.31 (br s, 1H), 7.48 (d, 2H, J=8.0 Hz), 7.21 (s, 1H), 7.14 (d, 2H, J=8.3 Hz), 6.89 (s, 1H), 6.65 (s, 1H), 6.38 (d, 1H, J=7.3 Hz), 6.25 (d, 1H, J=14.6 Hz), 5.93 (m, 1H), 5.85 (d, 1H, J=8.8 Hz), 5.50 (m, 1H), 5.34 (m, 1H), 5.24 (m, 2H), 5.15 (d, 1H, J=12.5 Hz), 4.86 (d, 1H, J=12.2 Hz), 4.62 (m, 3H), 4.01 (m, 1H), 3.86 (s, 3H), 3.78 (m, 1H), 3.04 (m, 1H), 2.56 (m, 1H), 2.20 (m, 1H), 1.84 (dd, 3H, J=6.6, 0.7 Hz), 1.48 (d, 3H, J=6.8 Hz), 1.20 (m, 3H), 1.05 (d, 9H, J=2.9 Hz), 1.03 (d, 9H, J=2.9 Hz), 0.99 (d, 3H, J=6.8 Hz), 0.95 (d, 3H, J=6.8 Hz), 0.88 (s, 9H), 0.27 (s, 3H), 0.14 (s, 3H).

(e) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (79)

Lithium acetate dihydrate (0.010 g, 0.10 mmol, 1.0 eq) was added to a solution of the silyl ether 78 (0.100 g, 0.10 mmol, 1.0 eq) in wet DMF (2 mL) at 25° C. for 3 hours. The reaction mixture was then diluted with ethyl acetate (20 mL) and washed successively with 0.1M citric acid (20 mL, pH 3), water (20 mL) and brine (5 mL), dried over MgSO$_4$, filtered and concentrated under reduced pressure. The residue was purified by flash chromatography (silica gel, 5/95 v/v methanol/DCM) to afford the product as a pale yellow oil (0.070 g, 83%). LC/MS (3.362 min (ES$^+$)), m/z: 820.2 [M+H]$^+$. $^1$H NMR (400 MHz, CDCl$_3$) δ 8.39 (s, 1H), 7.48 (d, 2H, J=8.2 Hz), 7.25 (s, 1H), 7.12 (d, 2H, J=8.1 Hz), 6.88 (s, 1H), 6.68 (s, 1H), 6.47 (d, 1H, J=7.6 Hz), 6.24 (d, 1H, J=15.2 Hz), 6.03 (s, 1H), 5.92 (m, 1H), 5.84 (d, 1H, J=8.9 Hz), 5.50 (m, 1H), 5.34 (m, 1H), 5.26 (m, 2H), 5.18 (d, 1H, J=12.3 Hz), 4.80 (d, 1H, J=12.4 Hz), 4.66-4.60 (m, 3H), 4.02 (m, 1H), 3.95 (s, 3H), 3.81 (m, 1H), 3.03 (m, 1H), 2.57 (m, 1H), 2.19 (m, 1H), 1.84 (dd, 3H, J=6.8, 0.8 Hz), 1.48 (d, 3H, J=7.1 Hz), 1.00 (d, 3H, J=6.8 Hz), 0.95 (d, 3H, J=6.8 Hz), 0.87 (s, 9H), 0.26 (s, 3H), 0.12 (s, 3H).

(iv) (11S,11aS)-4-((20S 23S)-1-iodo-20-isopropyl-23-methyl-2,18,21-trioxo-6,9,12,15-tetraoxa-3,19,22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (66, D)

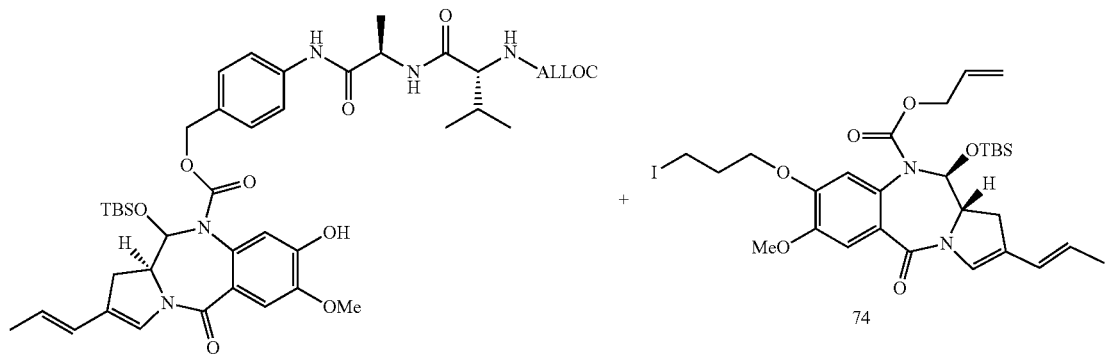

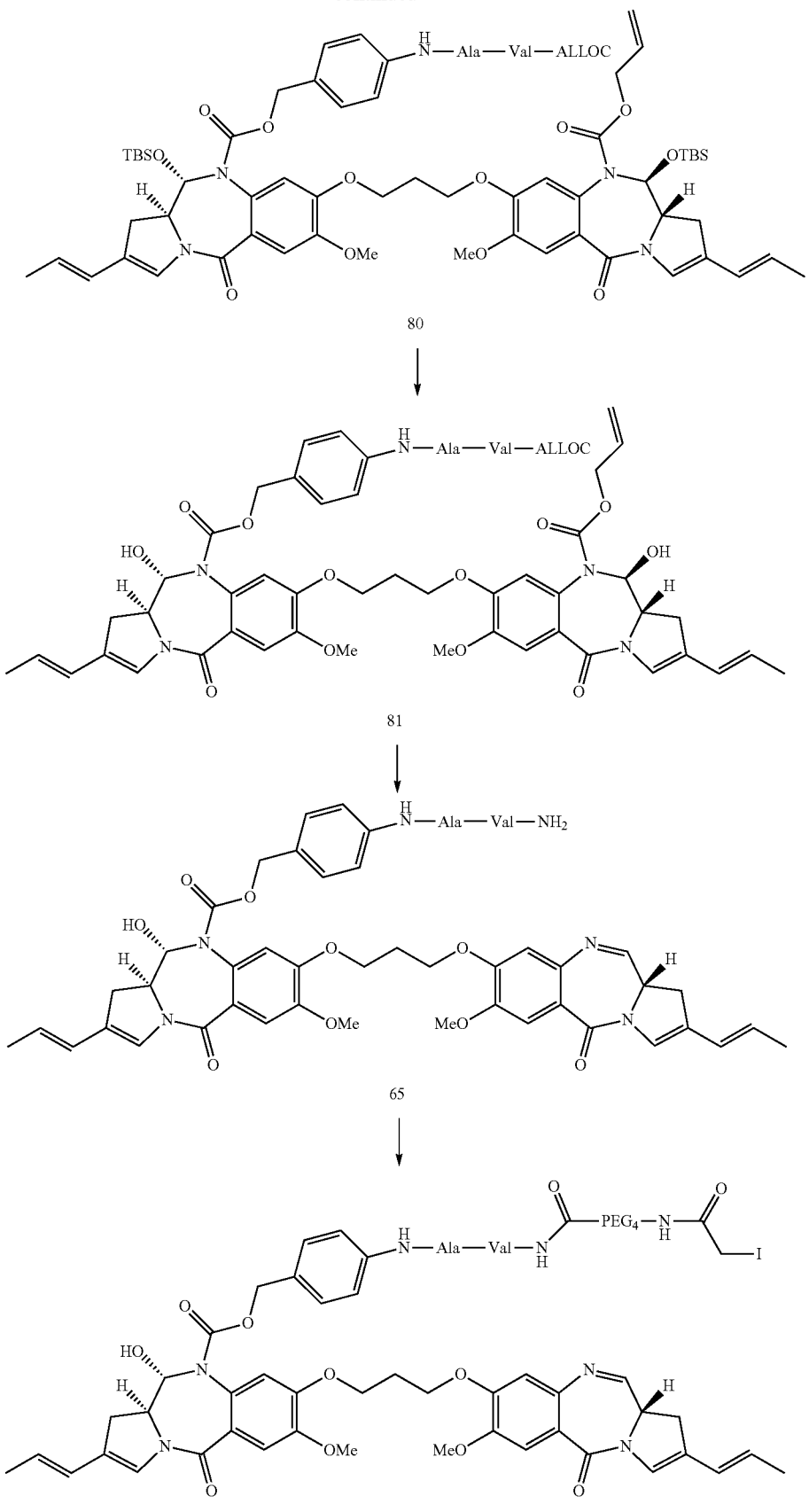

(a) (11S,11aS)-allyl 8-(3-((11S,11aS)-10-((4-((R)-2-((R)-2-(allyloxycarbonylamino)-3-methylbutanamido)propanamido)benzyloxy)carbonyl)-11-(tert-butyldimethylsilyloxy)-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-(tert-butyldimethylsilyloxy)-7-methoxy-5-oxo-2-((E)-prop-1-enyl)-11,11a-dihydro-1H-benzo[e]pyrrolo[1,2-a][1,4]diazepine-10(5H)-carboxylate (80)

Potassium carbonate (0.030 g, 0.21 mmol, 1.0 eq) was added to a solution of the phenol 79 (0.175 g, 0.21 mmol, 1.0 eq) and the iodo linker 74 (0.214 g, 0.32 mmol, 1.5 eq) in acetone (10 mL). The reaction mixture was heated under a nitrogen atmosphere at 75° C. in a sealed flask for 17 hours. The reaction mixture was concentrated to dryness under reduced pressure and purified by flash chromatography (silica gel, 2/98 v/v methanol/DCM to 5/95 v/v methanol/DCM) to afford the product as a pale yellow solid (0.100 g, 35%). LC/MS (4.293 min (ES$^+$)), m/z: 1359.13 [M]$^+$.

(b) (11S,11aS)-allyl 8-(3-((11S,11aS)-10-((4-((R)-2-((R)-2-(allyloxycarbonylamino)-3-methylbutanamido)propanamido)benzyloxy)carbonyl)-11-hydroxy-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-hydroxy-7-methoxy-5-oxo-2-((E)-prop-1-enyl)-11,11a-dihydro-1H-benzo[e]pyrrolo[1,2-a][1,4]diazepine-10(5H)-carboxylate (81)

Tetra-n-butylammonium fluoride (1M, 0.22 mL, 0.22 mmol, 2.0 eq) was added to a solution of silyl ether 80 (0.150 g, 0.11 mmol, 1.0 eq) in dry THF (2 mL). The reaction mixture was stirred at room temperature for 20 minutes, after which LC/MS indicated complete reaction. The reaction mixture was diluted with ethyl acetate (10 mL) and washed sequentially with water (5 mL) and brine (5 mL). The organic phase was dried over MgSO$_4$, filtered and concentrated under reduced pressure to leave a yellow solid. Purification by flash chromatography (silica gel, 6/94 v/v methanol/DCM to 10/90 v/v methanol/DCM) afforded the product as a pale yellow solid (0.090 g, 73%). LC/MS (2.947 min (ES$^+$)), m/z: 1154.0 [M+Na]$^+$. $^1$H NMR (400 MHz, CDCl$_3$) δ 8.39 (br s, 1H), 7.39 (d, 2H, J=7.6 Hz), 7.18 (d, 2H, J=10.6 Hz), 7.10 (m, 3H), 6.86 (d, 2H, J=10.0 Hz), 6.74 (s, 1H), 6.55 (s, 1H), 6.22 (dd, 2H, J=15.3, 6.6 Hz), 5.85 (m, 2H), 5.74 (m, 3H), 5.52 (m, 2H), 5.22 (m, 1H), 5.00 (m, 2H), 4.57 (m, 6H), 4.41 (m, 2H), 4.09 (m, 4H), 3.85 (m, 11H), 3.06 (m, 2H), 2.76 (m, 2H), 2.20 (m, 2H), 2.08 (m, 1H), 1.79 (d, 6H, J=6.4 Hz), 1.40 (d, 3H, J=6.1 Hz), 0.90 (m, 6H).

(c) (11S,11aS)-4-((R)-2-((R)-2-amino-3-methylbutanamido)propanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10 (5H)-carboxylate (65)

Tetrakis(triphenylphospene)palladium(0) (0.005 g, 0.005 mmol, 0.06 eq) was added to a solution of the bis-carbinolamine 81 (0.090 g, 0.08 mmol, 1.0 eq) and pyrrolidine (16 μL, 0.20 mmol, 2.5 eq) in dry DCM (5 mL). After 20 minutes, the reaction mixture was diluted with DCM (10 mL) and washed sequentially with saturated ammonium chloride (5 mL) and brine (5 mL), dried over MgSO$_4$, filtered and the solvent was removed under reduced pressure to leave the crude product as a pale yellow solid which was used in the next step without further purification (0.075 g, assumed 100% yield). LC/MS (2.060 min (ES$^+$)), m/z: 947.2 [M+H]$^+$.

(d) (11S,11aS)-4-((20S,23S)-1-iodo-20-isopropyl-23-methyl-2,18,21-trioxo-6,9,12,15-tetraoxa-3,19,22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10 (5H)-carboxylate (66, D)

EDCl (0.015 g, 0.08 mmol, 1.0 eq) was added to a solution of amine 65 (assumed 100% yield 0.075 g, 0.08 mmol, 1.0 eq) and iodoacetamide-PEG$_4$-acid 17 (0.034 g, 0.08 mmol, 1.0 eq) in dry dichloromethane (5 mL) and the reaction was stirred in the dark. After 50 minutes, a further amount of iodoacetamide-PEG$_4$-acid 17 (0.007 g, 0.016 mmol, 0.2 eq) was added along with a further amount of EDCl (0.003 g, 0.016 mmol, 0.2 eq). After a total of 2.5 hours, the reaction mixture was diluted with dichloromethane (15 mL) and washed sequentially with water (10 mL) and brine (10 mL). The organic phase was dried over MgSO$_4$, filtered and concentrated under reduced pressure. The resulting residue was purified by flash chromatography (silica gel, Chloroform 100% to 90:10 v/v Chloroform:Methanol). Pure fractions were combined to afford the product (0.0254 g, 23%, 2 steps). The crude fractions were collected and purified by preparative TLC (silica gel, 90:10 v/v Chloroform:Methanol) to afford a second batch of product (0.0036 g, 3%, 2 steps). LC/MS (2.689 min (ES$^+$)), m/z: 681.0 1/2[M+2H]$^+$.

Example 10: Activity of Released Compounds

K562 Assay

K562 human chronic myeloid leukaemia cells were maintained in RPM1 1640 medium supplemented with 10% fetal calf serum and 2 mM glutamine at 37° C. in a humidified atmosphere containing 5% CO$_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates (10$^4$ cells per well, 8 wells per sample). Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an IC$_{50}$ value was read as the dose required to reduce the final optical density to 50% of the control value.

Compound RelC has an $IC_{50}$ of less than 0.1 μM in this assay.

Compound RelE has an $IC_{50}$ of 0.425 nM in this assay.

Example 11: Formation of Conjugates

General Antibody Conjugation Procedure

Antibodies are diluted to 1-5 mg/mL in a reduction buffer (examples: phosphate buffered saline PBS, histidine buffer, sodium borate buffer, TRIS buffer). A freshly prepared solution of TCEP (tris(2-carboxyethyl)phosphine hydrochloride) is added to selectively reduce cysteine disulfide bridges. The amount of TCEP is proportional to the target level of reduction, within 1 to 4 molar equivalents per antibody, generating 2 to 8 reactive thiols. After reduction for several hours at 37° C., the mixture is cooled down to room temperature and excess drug-linker (A, B, C, D, E) added as a diluted DMSO solution (final DMSO content of up to 10% volume/volume of reaction mixture). The mixture was gently shaken at either 4° C. or room temperature for the appropriate time, generally 1-3 hours. Excess reactive thiols can be reacted with a 'thiol capping reagent' like N-ethyl maleimide (NEM) at the end of the conjugation. Antibody-drug conjugates are concentrated using centrifugal spin-filters with a molecular weight cut-off of 10 kDa or higher, then purified by tangential flow filtration (TFF) or Fast Protein Liquid Chromatography (FPLC). Corresponding antibody-drug conjugates can be determined by analysis by High-Performance Liquid Chromatography (HPLC) or Ultra-High-Performance Liquid Chromatography (UHPLC) to assess drug-per-antibody ratio (DAR) using reverse-phase chromatography (RP) or Hydrophobic-Interaction Chromatography (HIC), coupled with UV-Visible, Fluorescence or Mass-Spectrometer detection; aggregate level and monomer purity can be analysed by HPLC or UHPLC using size-exclusion chromatography coupled with UV-Visible, Fluorescence or Mass-Spectrometer detection. Final conjugate concentration is determined by a combination of spectroscopic (absorbance at 280, 214 and 330 nm) and biochemical assay (bicinchonic acid assay BCA; Smith, P. K., et al. (1985) Anal. Biochem. 150 (1): 76-85; using a known-concentration IgG antibody as reference). Antibody-drug conjugates are generally sterile filtered using 0.2 μm filters under aseptic conditions, and stored at +4° C., −20° C. or −80° C.

DAR Determination

Antibody or ADC (ca. 35 μg in 35 μL) was reduced by addition of 10 μL borate buffer (100 mM, pH 8.4) and 5 μL DTT (0.5 M in water), and heated at 37° C. for 15 minutes. The sample was diluted with 1 volume of acetonitrile: water: formic acid (49%: 49%: 2% v/v), and injected onto a Widepore 3.6μ XB-C18 150×2.1 mm (P/N 00F-4482-AN) column (Phenomenex Aeris) at 80° C., in a UPLC system (Shimadzu Nexera) with a flow rate of 1 ml/min equilibrated in 75% Buffer A (Water, Trifluoroacetic acid (0.1% v/v) (TFA), 25% buffer B (Acetonitrile:water:TFA 90%:10%: 0.1% v/v). Bound material was eluted using a gradient from 25% to 55% buffer B in 10 min. Peaks of UV absorption at 214 nm were integrated. The following peaks were identified for each ADC or antibody: native antibody light chain (L0), native antibody heavy chain (H0), and each of these chains with added drug-linkers (labelled L1 for light chain with one drug and H1, H2, H3 for heavy chain with 1, 2 or 3 attached drug-linkers). The UV chromatogram at 330 nm was used for identification of fragments containing drug-linkers (i.e., L1, H1, H2, H3).

A PBD/protein molar ratio was calculated for both light chains and heavy chains:

$$\frac{Drug}{Protein} \text{ ratio on light chain} = \frac{\% \text{ Area at 214 nm for } L1}{\% \text{ Area at 214 nm for } LD \text{ and } L1}$$

$$\frac{Drug}{Protein} \text{ ratio on heavy chain} = \frac{\sum_{n=0}^{B} n \times (\% \text{ area at 214 for } Hn)}{\sum_{n=0}^{B} \% \text{ area at 214 for } Hn}$$

Final DAR is calculated as:

$$DAR = 2 \times \left(\frac{Drug}{Protein} \text{ ratio on light chain} + \frac{Drug}{Protein} \text{ ratio on heavy chain}\right)$$

DAR measurement is carried out at 214 nm because it minimises interference from drug-linker absorbance.

Generation of ADCs

Antibody A (comprising a variable domain which is SEQ ID NO. 1 paired with SEQ ID NO. 7) was conjugated with drug linker A to give Conj A-A, and the DAR was measured to be 2.35.

Antibody B (comprising a variable domain which is SEQ ID NO. 2 paired with SEQ ID NO. 8) was conjugated with drug linker A to give Conj B-A, and the DAR was measured to be 2.2 (see table below).

Antibody C (comprising a variable domain which is SEQ ID NO. 6 paired with SEQ ID NO. 12) was conjugated with drug linker A to give Conj C-A, and the DAR was measured to be 1.97.

Antibody D (comprising a variable domain which is SEQ ID NO. 4 paired with SEQ ID NO. 10) was conjugated with drug linker A to give Conj D-A, and the DAR was measured to be 1.99.

Antibody E (comprising a variable domain which is SEQ ID NO. 5 paired with SEQ ID NO. 11) was conjugated with drug linker A to give Conj E-A, and the DAR was measured to be 1.89.

Antibody B (comprising a variable domain which is SEQ ID NO. 2 paired with SEQ ID NO. 8) was conjugated with drug linker D to give Conj B-D, and the DAR was measured to be 2.18 (see table below).

Antibody B (comprising a variable domain which is SEQ ID NO. 2 paired with SEQ ID NO. 8) was conjugated with drug linker E to give Conj B-E, and the DAR was measured to be 1.93 (see table below).

RB4v1.2 is an anti-CD19 antibody comprising a VH domain having the sequence according to SEQ ID NO. 2 and a VK domain having the sequence according to SEQ ID NO. 8.

As described above, ADCs targeted to CD19 were generated by conjugating RB4v1.2 antibodies to the drug linker A, E, or D. The resulting ADCs are listed in the table below, alongside the measured DAR. B12 anti-HIV gp120 antibody was used to generate control non-CD19 targeted ADCs.

| ADC | DAR | Concentration [mg/ml] | Yield [%] |
|---|---|---|---|
| RB4v1.2-A | 2.2 | 0.683 | 56 |
| RB4v1.2-E | 1.93 | 0.636 | 66 |
| RB4v1.2-D | 2.18 | 0.859 | 57 |

| ADC | DAR | Concentration [mg/ml] | Yield [%] |
|---|---|---|---|
| B12-A | 2.03 | 0.98 | 71 |
| B12-E | 1.84 | 0.515 | 70 |
| RB4v1.2-DM4 | 3.27 | 2.62 | 81 |

Example 12: In Vitro Cytotoxicity of ADCs

Cell Culture

WSU-DLCL2 and SU-DHL-1 cells were from the Leibniz Institute DSMZ-German Collection of Microorganisms and Cell Cultures. Ramos and Daudi cells were from the American Type Culture Collection. Cell culture medium was RPMI 1640 supplemented with L-Glutamine and 10% FBS. Cells were grown at 37° C., 5% $CO_2$, in a humidified incubator.

Cytotoxicity Assay

The concentration and viability of cultures of suspended cells (at up to $1 \times 10^6$/ml) were determined by mixing 1:1 with Trypan blue and counting clear (live)/blue (dead) cells with a haemocytometer. The cell suspension was diluted to the required seeding density (generally $10^5$/ml) and dispensed into 96-well flat bottomed plates. For Alamar blue assay, 100 µl/well was dispensed in black-well plates. For MTS assay, 50 µl/well was dispensed in clear-well plates. A stock solution (1 ml) of ADC (20 µg/ml) was made by dilution of filter-sterile ADC into cell culture medium. A set of 8×10-fold dilutions of stock ADC were made in a 24 well plate by serial transfer of 100 µl onto 900 µl of cell culture medium. Each ADC dilution (100 µl/well for Alamar blue, 50 µl/well for MTS) was dispensed into 4 replicate wells of the 96-well plate, containing cell suspension. Control wells received the same volume of culture medium only. After incubation for 4 days, cell viability was measured by either Alamar blue or MTS assay.

AlamarBlue® (Invitrogen, catalogue number DAL1025) was dispensed (20 µl per well) into each well and incubated for 4 hours at 37° C. in the $CO_2$-gassed incubator. Well fluorescence was measured at excitation 570 nm, emission 585 nm. Cell survival (%) was calculated from the ratio of mean fluorescence in the 4 ADC-treated wells compared to the mean fluorescence in the 4 control wells (100%).

MTS (Promega, catalogue number G5421) was dispensed (20 µl per well) into each well and incubated for 4 hours at 37° C. in the $CO_2$-gassed incubator. Absorbance was measured at 490 nm. Cell survival (%) was calculated from the mean absorbance in the 4 ADC-treated wells compared to the mean absorbance in the 4 control wells (100%). Dose response curves were generated from the mean data of 3 replicate experiments and the $EC_{50}$ was determined by fitting data to a sigmoidal dose-response curve with variable slope using Prism (GraphPad, San Diego, Calif.).

In Vitro Cytotoxicity

The efficacy of RB4v1.2-A was tested against CD19+ve cell lines, Daudi, Ramos and WSU-DLCL2. As a CD19-ve control, SU-DHL-1 cells were used.

FIG. 1 shows in vitro efficacy of RB4v1.2-A. Serial 10-fold dilutions (µg/mL) of RB4v1.2-A were incubated with Daudi, Ramos, WSU-DLCL2 or SU-DHL-1 cells. The Alamar Blue assay was performed at the end of the incubation period and cell survival calculated. Graphs represent the average of three replicate experiments.

RB4v1.2-A showed significant cytotoxicity against Daudi and Ramos cell, with slightly lower cytotoxicity against WSU-DLCL2 cells (FIG. 1).

| RB4v1.2-A | SUDHL1 | Daudi | Ramos | WSU-DLCL2 |
|---|---|---|---|---|
| EC50 (µg/mL) | ~6.706 | 0.001115 | 0.001021 | 0.1171 |

Figure 2:
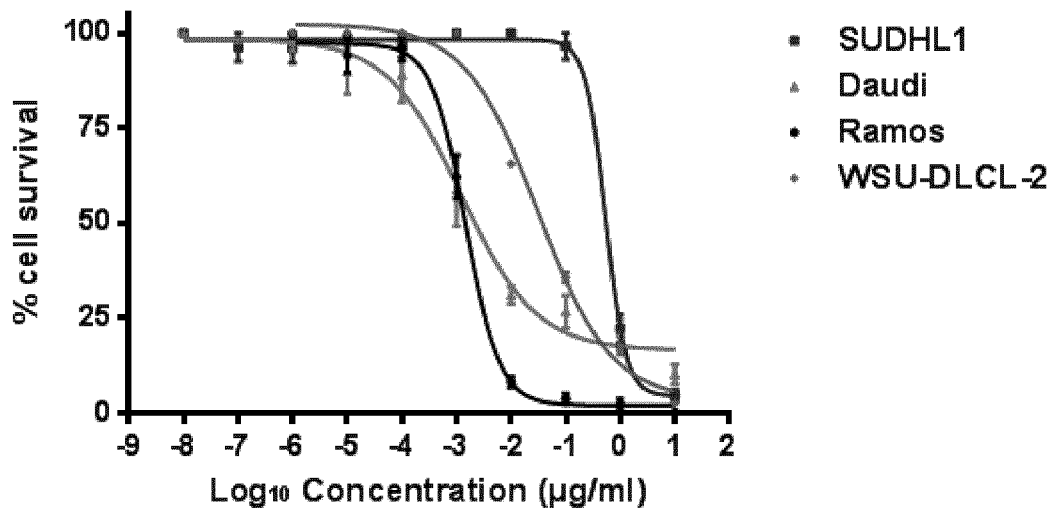
FIG. 2 shows the in vitro efficacy of another conjugate of the invention against Daudi, Ramos and WSU-DLCL2 cells.

FIG. 2 shows in vitro efficacy of RB4v1.2-E. Serial 10-fold dilutions (µg/mL) of RB4v1.2-E were incubated with Daudi, Ramos, WSU-DLCL2 or SU-DHL-1 cells. The Alamar Blue assay was performed at the end of the incubation period and cell survival calculated. Graphs represent the average of three replicate experiments.

RB4v1.2-E showed significant cytotoxicity against Daudi and Ramos cell, with slightly lower cytotoxicity against WSU-DLCL2 cells (FIG. 2).

| RB4v1.2-E | SUDHL1 | Daudi | Ramos | WSU-DLCL2 |
|---|---|---|---|---|
| EC50 (µg/mL) | 0.5390 | 0.001216 | 0.001467 | 0.03099 |

Figure 3:
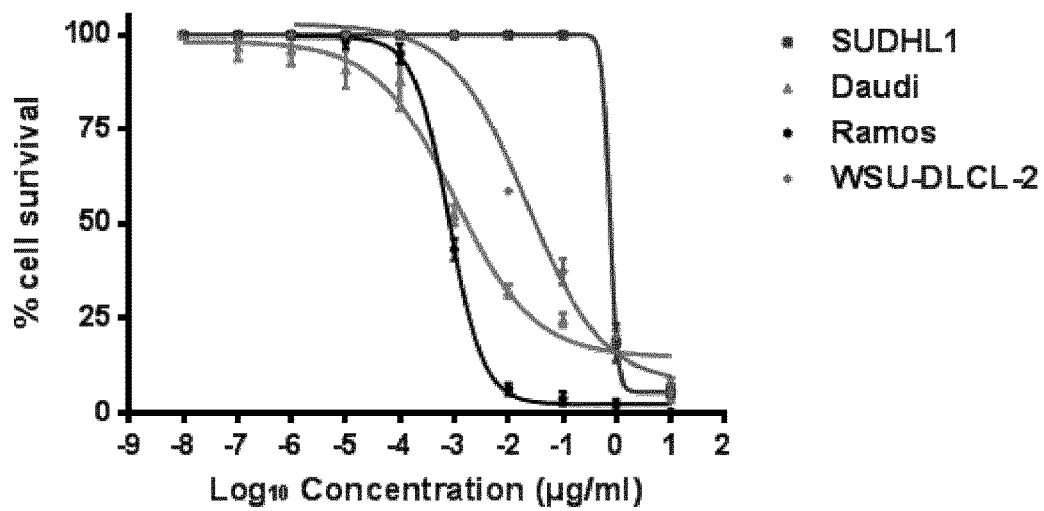
FIG. 3 shows the in vitro efficacy of another conjugate of the invention against Daudi, Ramos and WSU-DLCL2 cells.

FIG. 3 shows in vitro efficacy of RB4v1.2-D. Serial 10-fold dilutions (µg/mL) of RB4v1.2-D were incubated with Daudi, Ramos, WSU-DLCL2 or SU-DHL-1 cells. The Alamar Blue assay was performed at the end of the incubation period and cell survival calculated. Graphs represent the average of three replicate experiments.

RB4v1.2-D showed significant cytotoxicity against Daudi and Ramos cell, with slightly lower cytotoxicity against WSU-DLCL2 cells (FIG. 3).

| RB4v1.2-D | SUDHL1 | Daudi | Ramos | WSU-DLCL2 |
|---|---|---|---|---|
| EC50 (µg/mL) | ~0.7540 | 0.001022 | 0.0007979 | 0.02190 |

Example 13—In Vivo Anti-Tumour Activity of ADCs

The CD19+(ve) human Burkitt's lymphoma-derived cell line Ramos was used to determine the most potent PBD drug linker for RB4v1.2 in vivo. The antibody was conjugated to A, E, or D drug linkers as described above and tested in the Ramos xenograft model. As non-CD19-binding controls, the anti-HIV gp120 antibody, B12, linked to A or E was used. At the same time, to investigate any potential anti-tumor activity observed with the RB4v1.2 without a PBD warhead, RB4v1.2 was tested in vivo conjugated to DM4, a maytansinoid derivative which acts as a tubulin inhibitor.

Study Design

Drugs and Treatment:

| Group No | Animals per group | ADC | Dose level (mg/kg) | Dose volume (ml/kg) |
|---|---|---|---|---|
| 1 | 10 | [no treatment] | — | — |
| 2 | 10 | [vehicle only] | — | — |
| 3 | 10 | RB4v1.2 [no PBD] | 1.0 | 10 |
| 4 | 10 | RB4v1.2-A | 0.3 | 10 |
| 5 | 10 | RB4v1.2-A | 1.0 | 10 |
| 6 | 10 | RB4v1.2-E | 0.3 | 10 |
| 7 | 10 | RB4v1.2-E | 1.0 | 10 |
| 8 | 10 | RB4v1.2-D | 0.3 | 10 |
| 9 | 10 | RB4v1.2-D | 1.0 | 10 |

-continued

| Group No | Animals per group | ADC | Dose level (mg/kg) | Dose volume (ml/kg) |
|---|---|---|---|---|
| 10 | 10 | B12-E | 1.0 | 10 |
| 11 | 10 | B12-A | 1.0 | 10 |

Procedures:

Set up CR female NCr nu/nu mice with I×Ramos-SPN tumor cells in 0% Matrigel sc in flank.

Cell Injection Volume is 0.1 mL/mouse.

Age at Start Date: 8 to 12 weeks.

Perform a pair match when tumors reach an average size of 100-150 mm$^3$ and begin treatment.

Body Weight: qd×5 then bi-wk to end

Caliper Measurement: bi-wk to end

Report any adverse reactions or death immediately.

Any individual animal with a single observation of >30% body weight loss or three consecutive measurements of >25% body weight loss will be euthanized.

Any group with two measurements of mean body weight loss of >20% or >10% mortality will stop dosing. The group is not euthanized and recovery is allowed. Within a group with >20% weight loss, individuals hitting the individual body weight endpoint will be euthanized. If the group treatment related body weight loss is recovered to within 10% of the original weights, dosing may resume at a lower dose or less frequent dosing schedule. Exceptions to non-treatment body weight % recovery may be allowed on a case-by-case basis.

Endpoint TGD. Animals are to be monitored individually. The endpoint of the experiment is a tumor volume of 2000 mm$^3$ or 60 days, whichever comes first. Responders can be followed longer. When the endpoint is reached, the animals are to be euthanized.

General Methodological Approach

For the calculation of group mean tumor volumes the following rule was applied: when an animal exited the study due to tumor size, the final tumor volume recorded for the animal was included with the data used to calculate the mean volume at subsequent time points. Error bars indicate standard error of the mean (SEM). Tumor volumes values were not used to calculate group mean tumor volumes when fewer than 50% of the animals in a group remained in the study. Prism (GraphPad, San Diego, Calif.) was used for graphical presentations and statistical analyses.

Results

Figure 4:
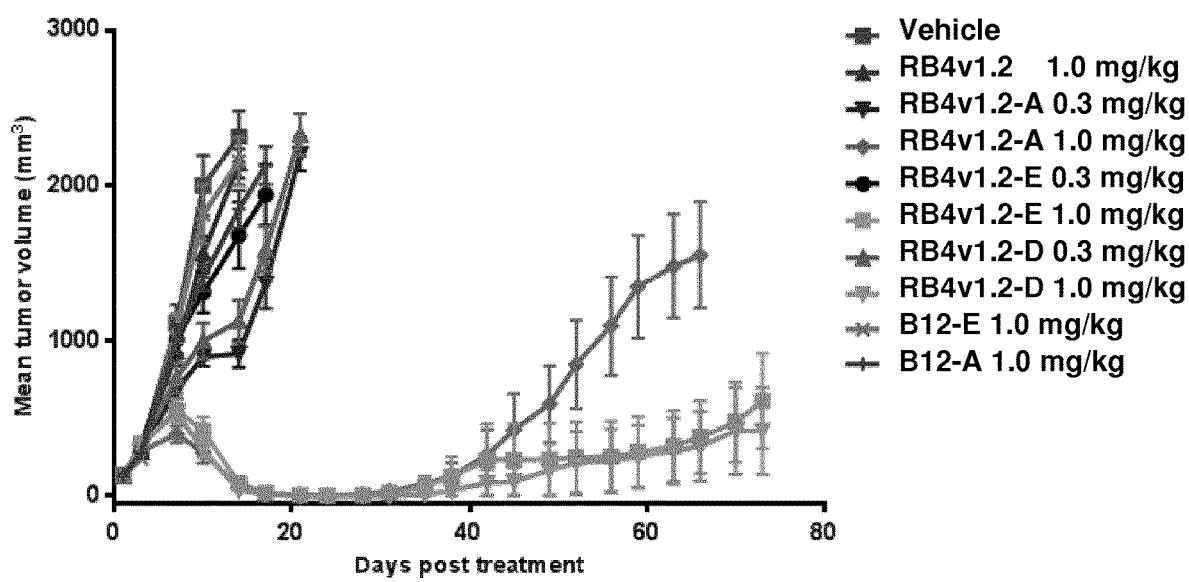
FIG. 4 shows the anti-tumour activity of conjugates of the invention and conjugates not of the invention in a Ramos xenograft model.

FIG. 4 shows drug linker selection for RB4v1.2-ADCs. Mice were dosed when the mean tumor volume per experimental group reached 0.1 cm$^3$ and they were treated with a single dose of the ADCs at 0.3 and 1 mg/kg (for binding ADCs) and 1 mg/kg (for non-binding-ADCs) via IV in the tail vein. Data represent the mean tumour volume (+/−SEM) from ten mice in each group.

RB4v1.2-A, -E and -D all exhibited anti-tumor activity, with RB4v1.2-E and -D appearing more potent than RB4v1.2-A (see FIG. 4). Neither non-binding ADC controls (B12-A and B12-E) showed a significant anti-tumor activity.

Abbreviations

Ac acetyl
Acm acetamidomethyl
Alloc allyloxycarbonyl
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl respectively
DMF N,N-dimethylformamide
Dnp dinitrophenyl
DTT dithiothreitol
Fmoc 9H-fluoren-9-ylmethoxycarbonyl
imp N—10 imine protecting group: 3-(2-methoxyethoxy)propanoate-Val-Ala-PAB
MC-OSu maleimidocaproyl-O—N-succinimide
Moc methoxycarbonyl
MP maleimidopropanamide
Mtr 4-methoxy-2,3,6-trimethtylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
TBDMS tert-butyldimethylsilyl
TBDPS tert-butyldiphenylsilyl
Teoc 2-(trimethylsilyl)ethoxycarbonyl
Tos tosyl
Troc 2,2,2-trichlorethoxycarbonyl chloride
Trt trityl
Xan xanthyl Sequences SEQ ID NO. 1 (RB4v1.0 VH):
QVQLVQPGAEWKPGASVKLSCKTSGYTFTSNWMH-WVKQRPGQGLEWIGEIDPSDSYTN YNQNFKGKAK-LTVDKSTSTAYMEVSSLRSDDTAVYYCARGSN-PYYYAMDYWGQGTSVTV S SEQ ID NO. 2 (RB4v1.2 VH):
QVQLVQPGAEWKPGASVKLSCKTSGYTFTSNWMH-WVKQAPGQGLEWIGEIDPSDSYTN YNQNFQGKAK-LTVDKSTSTAYMEVSSLRSDDTAVYYCARGSN-PYYYAMDYWGQGTSVTV S SEQ ID NO. 3 (B43 VH):
QVQLLESGAELVRPGSSVKISCKASGYAFSSYWMN-WVKQRPGQGLEWIGQIWPGDGDTN YNGKFKG-KATLTADESSSTAYMQLSSLRSEDSAVYSCARRETTT-VGRYYYAMDYWGQGT TVT SEQ ID NO. 4 (HD37 VH):
QVQLQQSGAELVRPGSSVKISCKASGYAFSSYWMN-WVKQRPGQGLEWIGQIWPGDGDT NYNGKFKG-KATLTADESSSTAYMQLSSLASEDSAVYFCARRETTT-VGRYYYAMDYWGQG TSVTVS SEQ ID NO. 5 (4G7 VH):
EVQLQQSGPELIKPGASVKMSCKASGYTFTSYVMH-WVKQKPGQGLEWIGYINPYNDGTKY NEKFKG-KATLTSDKSSSTAYMELSSLTSEDSAVYYCARG-TYYYGSRVFDYWGQGTTLTVS SEQ ID NO. 6 (FMC63 VH):
EVKLQESGPGLVAPSQSLSVTCTVSGVSLP-DYGVSWIRQPPRKGLEWLGVIWGSETTYYN SALK-SRLTIIKDNSKSQVFLKMNSLQTDDTAIYY-CAKHYYYGGSYAMDYWGQGTSVTVS SEQ ID NO. 7 (RB4v1.0 VK):
EIVLTQSPAIMSASPGERVTMTCSASSGVNYMHWY-QQKPGTSPRRWIYDTSKLASGVPAR FSGSGSGTSYS-LTISSMEPEDAATYYCHQRGSYTFGGGTKLEIK SEQ ID NO. 8 (RB4v1.2 VK):
EIVLTQSPAIMSASPGERVTMTCSASSGVNYMHWY-QQKPGTSPRRWIYDTSKLASGVPAR FSGSGSGTSYS-LTISSMEPEDAATYYCHQRGSYTFGGGTKLEIK

SEQ ID NO. 9 (B43 VK):

ELVLTQSPASLAVSLGQRATISCKASQSVDYDGDSYL-NWYQQIPGQPPKLLIYDASNLVSGI PPRFSGSGSGTD-FTLNIHPVEKVDAATYHCQQSTEDPWTFGGGT-KLEIK

SEQ ID NO. 10 (HD37 VK):
DILLTQTPASLAVSLGQRATISCKASQSVDYDGDSYL-NWYQQIPGQPPKLLIYDASNLVSGI P PRFSGSGS-GTDFTLNIHPVEKVDAATYHCQQSTEDPWTFGGGT-KLEIK

SEQ ID NO. 11 (4G7 VK):
DIVMTQAAPSIPVTPGESVSISCRSSKSLLNSNGNTY-LYWFLQRPGQSPQLLIYRMSNLASG VPDRFSGSGSG-TAFTLRISRVEAEDVGVYYCMQHLEYPFTFGAGT-KLELK

SEQ ID NO. 12 (FMC63 VK):
DIQMTQTTSSLSASLGDRVTISCRASQDISKYLNWY-QQKPDGTVKLLIYHTSRLHSGVPSRF SGSGSGTDYS-LTISNLEQEDIATYFCQQGNTLPYTFGGGTKLEIT

The invention claimed is:
1. A conjugate of formula ConjA:

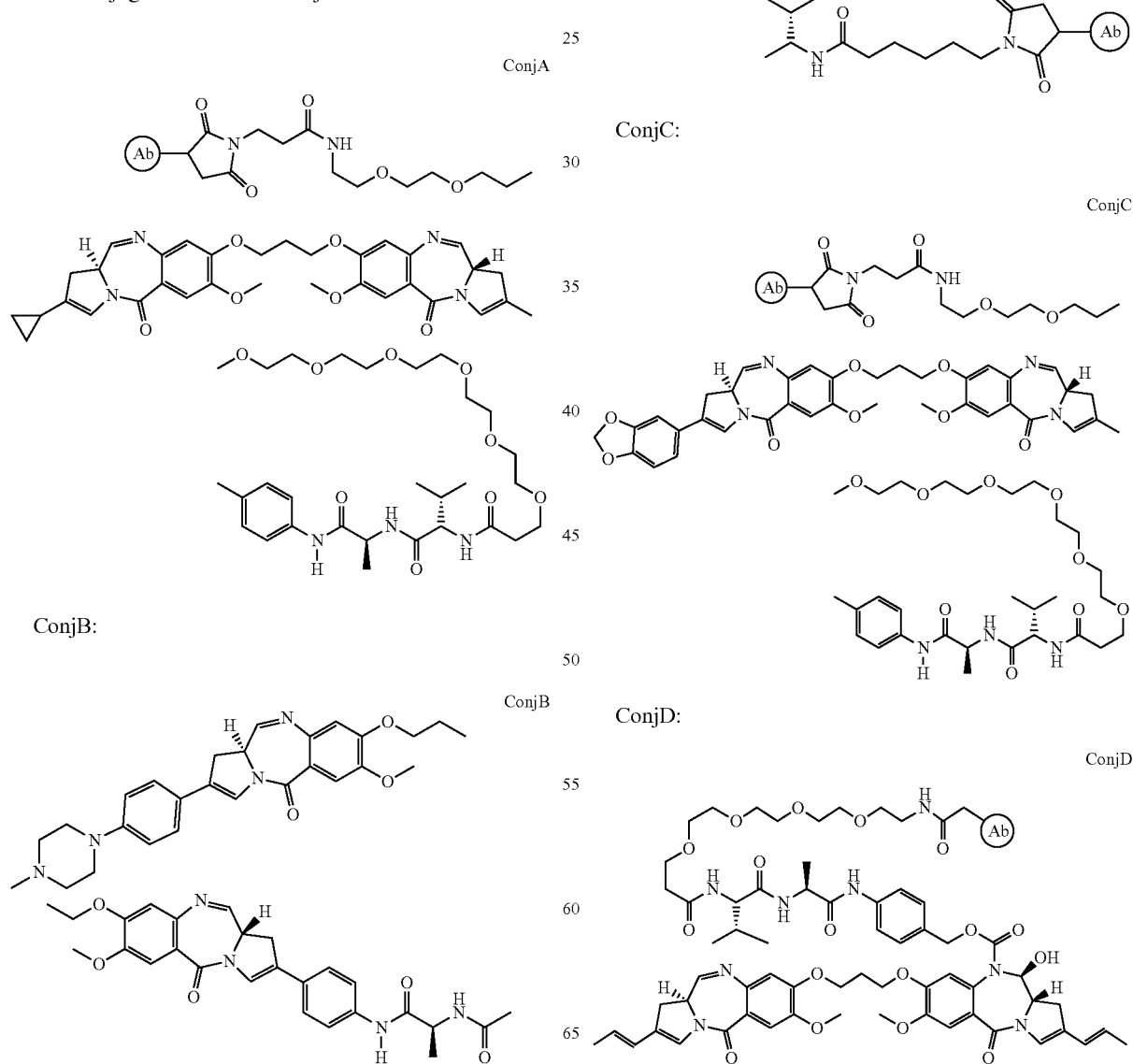

or ConjE:

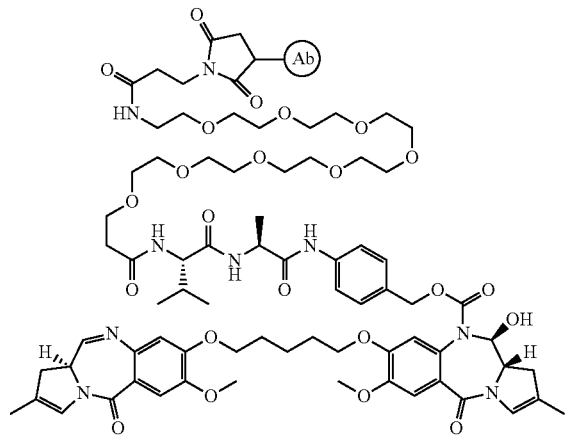

where Ab is an antibody that binds to CD19, the antibody comprising a VH domain having the amino acid sequence of SEQ ID NO. 1 and a VL domain having the amino acid sequence of SEQ ID NO. 7; and wherein the drug loading is from 1 to 8.

2. The conjugate of claim 1, wherein the antibody is an intact antibody.

3. The conjugate of claim 1, wherein the antibody is humanised, deimmunised or resurfaced.

4. The conjugate of claim 1, wherein the drug loading is 1, 2, 3, or 4.

5. A mixture of the conjugates of claim 1, wherein the average value of drug loading is about 2 to about 5.

6. The conjugate of claim 1, wherein said conjugate is ConjE.

7. A pharmaceutical composition comprising the conjugate of claim 1, and a pharmaceutically acceptable diluent, carrier or excipient.

8. The pharmaceutical composition of claim 7, further comprising a therapeutically effective amount of a chemotherapeutic agent.

9. A method of treating a CD19 overexpressing cancer comprising administering to a patient the pharmaceutical composition of claim 7, wherein said conjugate is ConjE.

10. The method of claim 9, wherein the patient is administered a chemotherapeutic agent; in combination with the conjugate.

11. The method of claim 10, wherein the chemotherapeutic agent is rituximab.

* * * * *

SEQUENCE LISTING

```
<160> NUMBER OF SEQ ID NOS: 15

<210> SEQ ID NO 1
<211> LENGTH: 119
<212> TYPE: PRT
<213> ORGANISM: Artificial sequence
<220> FEATURE:
<223> OTHER INFORMATION: Synthetic sequence: Antibody sequence RB4v1.0
      VH of PCT/EP2013/071346

<400> SEQUENCE: 1

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Lys Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser
        115

<210> SEQ ID NO 2
<211> LENGTH: 119
<212> TYPE: PRT
<213> ORGANISM: Artificial sequence
<220> FEATURE:
<223> OTHER INFORMATION: Synthetic sequence: Antibody sequence RB4v1.2
      VH of PCT/EP2013/071346

<400> SEQUENCE: 2

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95
```

```
Ala Arg Gly Ser Asn Pro Tyr Tyr Tyr Ala Met Asp Tyr Trp Gly Gln
            100                 105                 110

Gly Thr Ser Val Thr Val Ser
        115

<210> SEQ ID NO 3
<211> LENGTH: 121
<212> TYPE: PRT
<213> ORGANISM: Artificial sequence
<220> FEATURE:
<223> OTHER INFORMATION: Synthetic sequence: Antibody sequence B43 VH of
      PCT/EP2013/071346

<400> SEQUENCE: 3

Gln Val Gln Leu Leu Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr
        115                 120

<210> SEQ ID NO 4
<211> LENGTH: 123
<212> TYPE: PRT
<213> ORGANISM: Artificial sequence
<220> FEATURE:
<223> OTHER INFORMATION: Synthetic sequence: Antibody sequence HD37 VH
      of PCT/EP2013/071346

<400> SEQUENCE: 4

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Ser Val Thr Val Ser
        115                 120
```

```
<210> SEQ ID NO 5
<211> LENGTH: 120
<212> TYPE: PRT
<213> ORGANISM: Artificial sequence
<220> FEATURE:
<223> OTHER INFORMATION: Synthetic sequence: Antibody sequence 4G7 VH of
      PCT/EP2013/071346

<400> SEQUENCE: 5

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser
        115                 120

<210> SEQ ID NO 6
<211> LENGTH: 119
<212> TYPE: PRT
<213> ORGANISM: Artificial sequence
<220> FEATURE:
<223> OTHER INFORMATION: Synthetic sequence: Antibody sequence FMC63 VH
      of PCT/EP2013/071346

<400> SEQUENCE: 6

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser
        115

<210> SEQ ID NO 7
<211> LENGTH: 104
<212> TYPE: PRT
<213> ORGANISM: Artificial sequence
<220> FEATURE:
<223> OTHER INFORMATION: Synthetic sequence: Antibody sequence RB4v1.0
      VK of PCT/EP2013/071346
```

```
<400> SEQUENCE: 7

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
                20                  25                  30

His Trp Tyr Gln Gln Lys Pro Gly Thr Ser Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 8
<211> LENGTH: 104
<212> TYPE: PRT
<213> ORGANISM: Artificial sequence
<220> FEATURE:
<223> OTHER INFORMATION: Synthetic sequence: Antibody sequence RB4v1.2
      VK of PCT/EP2013/071346

<400> SEQUENCE: 8

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
                20                  25                  30

His Trp Tyr Gln Gln Lys Pro Gly Thr Ser Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 9
<211> LENGTH: 111
<212> TYPE: PRT
<213> ORGANISM: Artificial sequence
<220> FEATURE:
<223> OTHER INFORMATION: Synthetic sequence: Antibody sequence B43 VK of
      PCT/EP2013/071346

<400> SEQUENCE: 9

Glu Leu Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60
```

```
Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110

<210> SEQ ID NO 10
<211> LENGTH: 111
<212> TYPE: PRT
<213> ORGANISM: Artificial sequence
<220> FEATURE:
<223> OTHER INFORMATION: Synthetic sequence: Antibody sequence HD37 VK
      of PCT/EP2013/071346

<400> SEQUENCE: 10

Asp Ile Leu Leu Thr Gln Thr Pro Ala Ser Leu Ala Val Ser Leu Gly
 1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110

<210> SEQ ID NO 11
<211> LENGTH: 112
<212> TYPE: PRT
<213> ORGANISM: Artificial sequence
<220> FEATURE:
<223> OTHER INFORMATION: Synthetic sequence: Antibody sequence 4G7 VK of
      PCT/EP2013/071346

<400> SEQUENCE: 11

Asp Ile Val Met Thr Gln Ala Ala Pro Ser Ile Pro Val Thr Pro Gly
 1               5                  10                  15

Glu Ser Val Ser Ile Ser Cys Arg Ser Ser Lys Ser Leu Leu Asn Ser
             20                  25                  30

Asn Gly Asn Thr Tyr Leu Tyr Trp Phe Leu Gln Arg Pro Gly Gln Ser
         35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ala Gly Thr Lys Leu Glu Leu Lys
            100                 105                 110

<210> SEQ ID NO 12
<211> LENGTH: 107
<212> TYPE: PRT
<213> ORGANISM: Artificial sequence
```

```
<220> FEATURE:
<223> OTHER INFORMATION: Synthetic sequence: Antibody sequence FMC63 VK
      of PCT/EP2013/071346

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 13
<211> LENGTH: 607
<212> TYPE: PRT
<213> ORGANISM: Bos taurus

<400> SEQUENCE: 13

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Thr Ser Ser Ala Arg Gln Arg Leu Arg Cys Ala
210                 215                 220
```

```
Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
        435                 440                 445

Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 14
<211> LENGTH: 557
<212> TYPE: PRT
<213> ORGANISM: Homo sapiens
```

<400> SEQUENCE: 14

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415
```

Asp Ser Glu Phe Tyr Glu Asn Asp Ser Asn Leu Gly Gln Asp Gln Leu
              420                 425                 430

Ser Gln Asp Gly Ser Gly Tyr Glu Asn Pro Glu Asp Glu Pro Leu Gly
              435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
              485                 490                 495

Gly Ser Gln Ser Tyr Glu Asp Met Arg Gly Ile Leu Tyr Ala Ala Pro
              500                 505                 510

Gln Leu Arg Ser Ile Arg Gly Gln Pro Gly Pro Asn His Glu Glu Asp
              515                 520                 525

Ala Asp Ser Tyr Glu Asn Met Asp Asn Pro Asp Gly Pro Asp Pro Ala
              530                 535                 540

Trp Gly Gly Gly Gly Arg Met Gly Thr Trp Ser Thr Arg
545                 550                 555

<210> SEQ ID NO 15
<211> LENGTH: 1968
<212> TYPE: DNA
<213> ORGANISM: Homo sapiens

<400> SEQUENCE: 15

| | | | | |
|---|---|---|---|---|
| aggcccctgc | ctgccccagc | atccctgcg | cgaagctggg | tgccccggag agtctgacca | 60 |
| ccatgccacc | tcctcgcctc | ctcttcttcc | tcctcttcct | caccccatg gaagtcaggc | 120 |
| ccgaggaacc | tctagtggtg | aaggtggaag | agggagataa | cgctgtgctg cagtgcctca | 180 |
| aggggaccctc | agatggcccc | actcagcagc | tgacctggtc | tcgggagtcc ccgcttaaac | 240 |
| ccttcttaaa | actcagcctg | gggctgccag | gcctggaat | ccacatgagg cccctggcca | 300 |
| tctggctttt | catcttcaac | gtctctcaac | agatgggggg | cttctacctg tgccagccgg | 360 |
| ggcccccctc | tgagaaggcc | tggcagcctg | ctggacagt | caatgtggag gcagcggg | 420 |
| agctgttccg | gtggaatgtt | tcggacctag | gtggcctggg | ctgtgggcctg aagaacaggt | 480 |
| cctcagaggg | ccccagctcc | ccttccggga | agctcatgag | ccccaagctg tatgtgtggg | 540 |
| ccaaagaccg | ccctgagatc | tgggaggag | agcctccgtg | tctcccaccg agggacagcc | 600 |
| tgaaccagag | cctcagccag | gacctcacca | tggccctgg | ctccacactc tggctgtcct | 660 |
| gtgggtacc | ccctgactct | gtgtccaggg | gcccctctc | ctggacccat gtgcaccca | 720 |
| aggggcctaa | gtcattgctg | agcctagagc | tgaaggacga | tcgccccggcc agagatatgt | 780 |
| gggtaatgga | gacgggtctg | ttgttgcccc | gggccacagc | tcaagacgct ggaaagtatt | 840 |
| attgtcaccg | tggcaacctg | accatgtcat | tccacctgga | gatcactgct cggccagtac | 900 |
| tatggcactg | gctgctgagg | actggtggct | ggaaggtctc | agctgtgact ttggcttatc | 960 |
| tgatcttctg | cctgtgttcc | cttgtgggca | ttcttcatct | tcaaagagcc ctggtcctga | 1020 |
| ggaggaaaag | aaagcgaatg | actgacccca | ccaggagatt | cttcaaagtg acgcctcccc | 1080 |
| caggaagcgg | gccccagaac | cagtacggga | acgtgctgtc | tctccccaca cccacctcag | 1140 |
| gcctcggacg | cgcccagcgt | tgggccgcag | gctgggggg | cactgccccg tcttatggaa | 1200 |
| acccgagcag | cgacgtccag | gcggatggag | ccttggggtc | ccggagcccg ccggagtgg | 1260 |
| gcccagaaga | agaggaaggg | gagggctatg | aggaacctga | cagtgaggag gactccgagt | 1320 |

-continued

| | |
|---|---|
| tctatgagaa cgactccaac cttgggcagg accagctctc ccaggatggc agcggctacg | 1380 |
| agaaccctga ggatgagccc ctgggtcctg aggatgaaga ctccttctcc aacgctgagt | 1440 |
| cttatgagaa cgaggatgaa gagctgaccc agccggtcgc caggacaatg gacttcctga | 1500 |
| gccctcatgg gtcagcctgg gaccccagcc gggaagcaac ctccctggca gggtcccagt | 1560 |
| cctatgagga tatgagagga atcctgtatg cagccccca gctccgctcc attcggggcc | 1620 |
| agcctggacc caatcatgag gaagatgcag actcttatga gaacatggat aatcccgatg | 1680 |
| ggccagaccc agcctgggga ggaggggcc gcatgggcac ctggagcacc aggtgatcct | 1740 |
| caggtggcca gcctggatct cctcaagtcc ccaagattca cacctgactc tgaaatctga | 1800 |
| agacctcgag cagatgatgc caacctctgg agcaatgttg cttaggatgt gtgcatgtgt | 1860 |
| gtaagtgtgt gtgtgtgtgt gtgtgtgtat acatgccagt gacacttcca gtcccctttg | 1920 |
| tattccttaa ataaactcaa tgagctcttc caatcctaaa aaaaaaa | 1968 |